United States Patent [19]

Levin et al.

[11] Patent Number: 5,358,951
[45] Date of Patent: Oct. 25, 1994

[54] ANGIOTENSIN II RECEPTOR BLOCKING 2, 3, 6 SUBSTITUTED QUINAZOLINONES

[75] Inventors: Jeremy I. Levin, Nanuet; Aranapakam M. Venkatesan, Elmhurst, both of N.Y.

[73] Assignee: American Cyanamid Company, Wayne, N.J.

[21] Appl. No.: 52,945

[22] Filed: Apr. 23, 1993

[51] Int. Cl.$^5$ .................. A61K 31/55; A61K 31/505; C07D 498/04; C07D 498/08
[52] U.S. Cl. ..................................... 514/259; 544/284; 544/287
[58] Field of Search .................. 544/284, 287; 514/259

[56] References Cited

U.S. PATENT DOCUMENTS

| | | | |
|---|---|---|---|
| 5,284,853 | 2/1994 | Levin et al. | 514/259 |
| 5,288,720 | 2/1994 | Albright | 514/259 |

*Primary Examiner*—Nicholas Rizzo
*Assistant Examiner*—Matthew V. Grumbling
*Attorney, Agent, or Firm*—Thomas S. Szatkowski

[57] ABSTRACT

This disclosure describes novel 2,3,6, substituted quinazolinones of the formula:

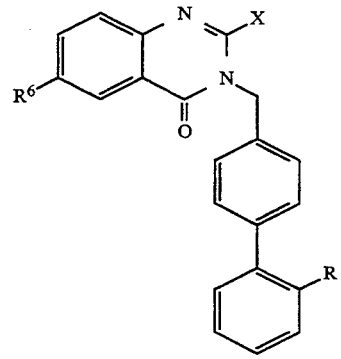

FORMULA I wherein $R_1$, $R^6$ and X are described in the specification which have activity as angiotensin II (AII) antagonistis.

56 Claims, 9 Drawing Sheets

ANGIOTENSIN II RECEPTOR BLOCKING 2, 3, 6 SUBSTITUTED QUINAZOLINONES

BACKGROUND OF THE INVENTION

1. Field of the Invention

This invention relates to certain 6-(polycyclic heterocyclic)-2-(lower alkyl)-3-(substituted) quinazolinone compounds which have demonstrated activity as angiotensin II (AII) antagonists and are therefore useful in alleviating angiotensin induced hypertension and for treating congestive heart failure.

SUMMARY OF THE INVENTION

According to the present invention, there are provided novel 6-(polycyclic heterocyclic)-2-(lower alkyl)-3-(substituted) quinazolinone compounds of Formula I which have angiotensin II antagonizing properties and are useful as anti-hypertensives:

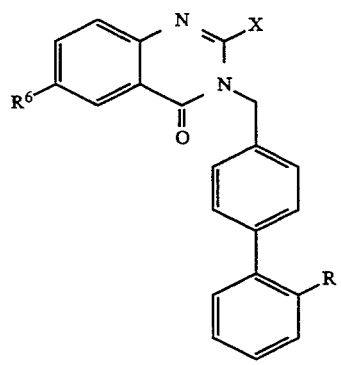

FORMULA I wherein:
R is

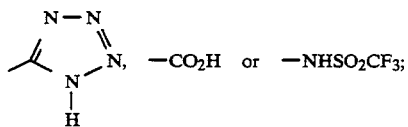

X is lower alkyl of 3 to 5 carbon atoms;
$R^6$ is:

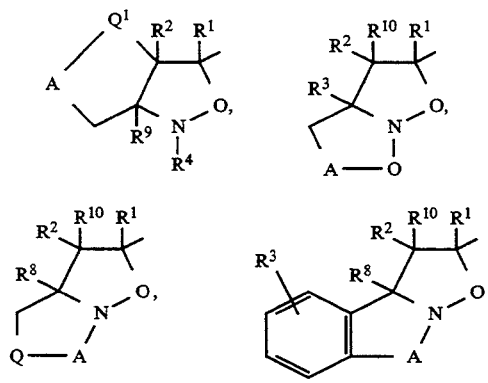

$R^1$ is H, lower alkyl of 1 to 4 carbon atoms (optionally substituted with —$OR^7$, —$CO_2R^7$, —CN, —$N(R^7)(R^{13})$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl , or Br) , pyridine, thiophene, furan, —$OR^7$, —$CO_2R^7$, —CN, —$CON(R^7)(R^{13})$ —$CF_3$, —SPh, —$N(R^7)(R^{13})$ or

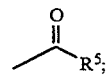

$R^2$ is H, lower alkyl of 1 to 4 carbon atoms (optionally substituted with —$OR^7$, —$CO_2R^7$, —CN, —$N(R^7)(R^{13})$ , phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br) , pyridine, thiophene, furan, —$CO_2R^7$, —CN, —$CON(R^7)(R^{13})$, or

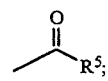

$R^3$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene or furan, —$CO_2R^7$, —$CON(R^7)(R^{13})$, —CN, —$NO_2$, or

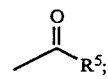

$R^4$ is H, —$CO_2R^{12}$, —$SO_2R^{12}$, lower alkyl of 1 to 4 carbon atoms, benzyl, substituted benzyl (substitution selected from mono-lower alkyl of 1 to 3 carbon atoms, trifluoromethyl, nitro, O-alkyl of 1 to 3 carbon atoms, F, Cl, or Br), phenyl, substituted phenyl (substitution selected from mono-lower alkyl of 1 to 3 carbon atoms, trifluoromethyl, nitro, O-alkyl of 1 to 3 carbon atoms, F, Cl, or Br), —$CON(R^7)(R^{13})$, or

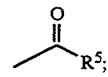

$R^{12}$ is phenyl, substituted phenyl (substitution selected from mono-lower alkyl of 1 to 3 carbon atoms, trifluoromethyl, nitro, O-alkyl of 1 to 3 carbon atoms, F, Cl, or Br);
$R^5$ is H, lower alkyl of 1 to 4 carbon atoms;
$R^7$ is H, lower alkyl of 1 to 4 carbon atoms;
$R^8$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), —$CO_2R^7$, —$CH_2OH$, —CN, —$CON(R^7)(R^{13})$, or

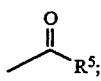

$R^9$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br);

$R^{10}$ is H, lower alkyl of 1 to 4 carbon atoms (optionally substituted with —$OR^7$, —$CO_2R^7$, —CN, —$N(R^7)(R^{13})$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —$OR^7$, —$CO_2R^7$, —CN, —$CON(R^7)(R^{13})$, —$CF_3$, or

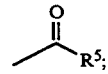

$R^{13}$ is H, lower alkyl of 1 to 4 carbon atoms;
Q is —O—, —$(CR^{11}R^{14})_n$—, or a single bond,
$Q^1$ is —O—, —$(CR^{11}R^{14})_n$—, or a single bond;
n is 1 to 5;
A is —$(CR^{11}R^{14})_m$—;
m is 2 to 5, provided that n+m is not greater than 6;
$R^{11}$ is H, lower alkyl of 1 to 4 carbon atoms (optionally substituted with —$OR^7$, —$CO_2R^7$, —CN, —$N(R^7)(R^{13})$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —$OR^7$, —$CO_2R^7$, —CN, —$CON(R^7)(R^{13})$, —$CF_3$, or

$R^{14}$ is H, lower alkyl of 1 to 4 carbon atoms (optionally substituted with —$OR^7$, —$CO_2R^7$, —CN, —$N(R^7)(R^{13})$, phenyl, substituted phenyl (substitution selected from mono-lower alkyl of 1 to 3 carbon atoms, trifluoromethyl, nitro, O-alkyl of 1 to 3 carbon atoms, F, Cl, or Br), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —$OR^7$, —$CO_2R^7$, —CN, —$CON(R^7)(R^{13})$, —$CF_3$, or

and the pharmaceutically acceptable salts thereof.

The present invention also provides novel intermediate compounds, methods for making the novel 2,3,6 substituted quinazolinone angiotensin II antagonizing compounds, methods for making the novel intermediates, methods of using the novel quinazolinone angiotensin II antagonizing compounds to treat hypertension, congestive heart failure and to antagonize the effects of angiotensin II.

DETAILED DESCRIPTION OF THE INVENTION

Figure 1:
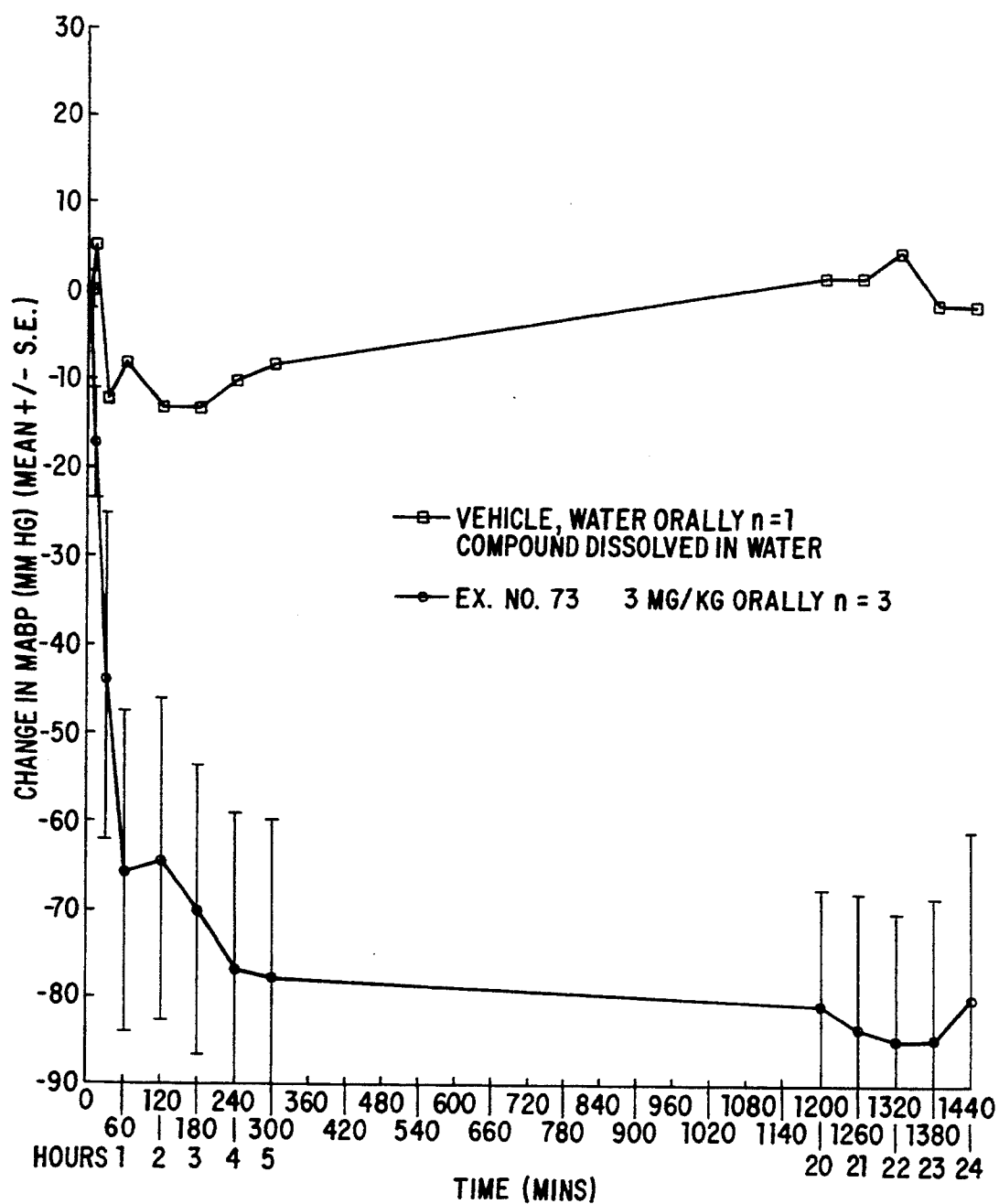
FIGS. 1 to 9 depict mean average blood pressure response data in aorta coarcted hypertensive rats.

The novel compounds of the present invention are prepared according to the following reaction schemes.

Referring to Scheme I, the corresponding anthranilic acid 2 where $R^{20}$ is I, Br or $CH_3$, is heated to reflux in alkyl acid anhydride 3 wherein X is lower alkyl of 3 to 5 carbon atoms to provide the 4H-3,1-benzoxazin-4-ones 4 which are isolated by concentrating the reaction mixtures and used without further purification. When the 4H-3,1-benzoxazin-4-ones 4 are refluxed in ethyl alcohol containing ammonia, or ammonium hydroxide solution, the quinazolinone intermediates 5 are obtained.

Scheme I

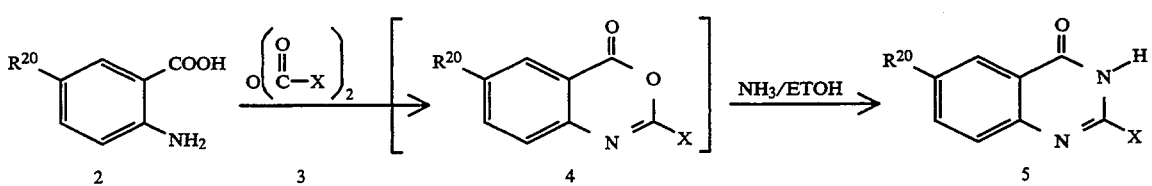

The quinazolinone intermediates 5 are modified according to the following reaction schemes to obtain the novel quinazolinone Angiotensin II antagonist compounds of the present invention.

In Scheme II, 6-methyl-2-lower alkylquinazolinone 6, as prepared by Scheme I, is brominated with N-bromosuccinimide to give the bromomethyl compound 7. Hydrolysis of the bromide with aqueous potassium carbonate in dimethylsulfoxide yields the primary alcohol 8. The alcohol 8 is oxidized with pyridinium dichromate in N,N-dimethylformamide to afford aldehyde 9. The aldehyde 9 is reacted with a variety of Grignard Reagents $R^1MgBr$ or lithium reagents $R^1Li$ in tetrahydrofuran where $R^1$ is hereinbefore defined provided however that for this reaction scheme $R^1$ cannot contain —$CO_2R^7$, —$CON(R^7)(R^{13})$, or

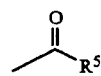

nor can it be H, —$OR^7$, —CN, —$CF_3$, —Sph, or —$N(R^7)(R^{13})$ to give the desired secondary alcohol 10. Alcohol 10 is oxidized with pyridinium dichromate in N,N-dimethylformamide to afford ketone 11.

alcohol 8. Alcohol 8 is oxidized with pyridinium dichromate to yield aldehyde 9.

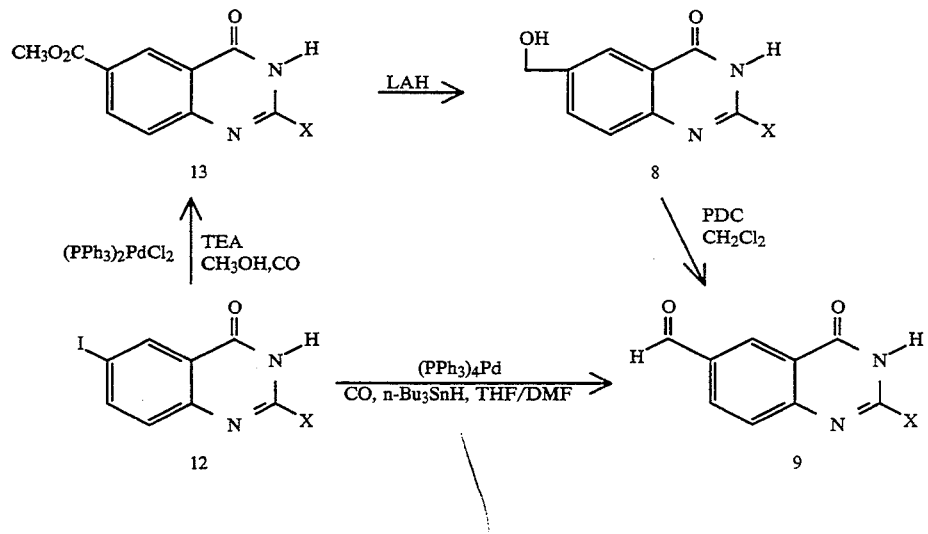

As shown in Scheme IV, the palladium (II) catalyzed coupling of (trimethylsilyl)acetylene with 2-alkylsubstituted-6-iodo-4(1H)-quinazolinone 12 yields the acetylenic quinazolinone 14. Desilylation of the acetylene with sodium hydroxide in water-methanol gives the terminal acetylene 15. Hydration of acetylene 15 with catalytic mercuric sulfate-sulfuric acid in acetic acid affords methyl ketone 16. The palladium (II) catalyzed

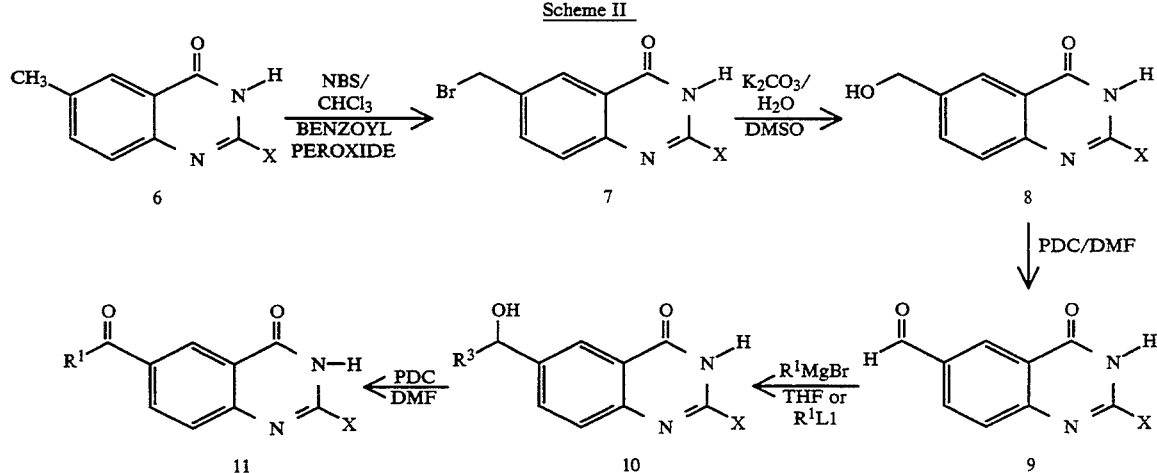

In an alternate route to 9, as shown in Scheme III, 2-alkylsubstituted-6-iodo-4(1H)-quinazolinone 12, prepared by Scheme I is reacted via a palladium catalyzed formylation. Additionally, 12 is converted to ester 13 by palladium (II) catalyzed coupling in the presence of carbon monoxide and methanol. Reduction of 13 with lithium aluminum hydride in tetrahydrofuran gives coupling of substituted acetylenes where $R^2$ is as defined hereinabove with 2-alkylsubstituted-6-iodo-4(1H)-quinazolinone 12 yields the acetylenic quinazolinone 17. Hydration of 17 with catalytic mercuric sulfate-sulfuric acid in acetic acid gives a mixture of ketones 18 and 35. The ketones are separated by chromatography.

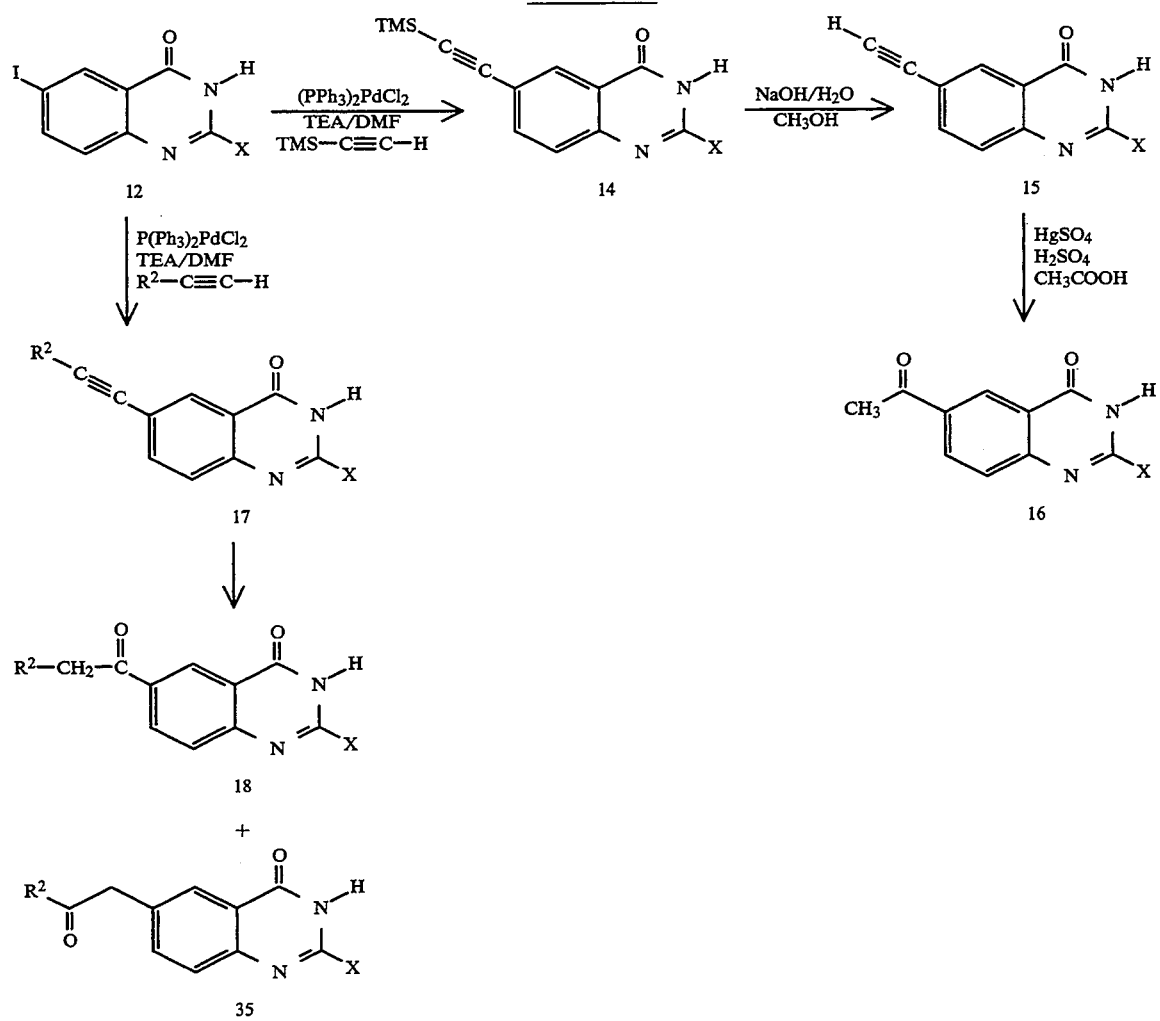

In addition as shown in Scheme V, acetylene 15 is hydrogenated over 5% palladium-barium sulfate in pyridine to give either the terminal olefin 21 or the ethyl substituted quinazolinone 22. Olefin 21 is separated from 22 by chromatography. Also, acetylene 17 is hydrogenated over 5% palladium-barium sulfate in pyridine to give olefin 23 and alkyl substituted quinazolinone 24. Olefin 23 is separated from 24 by chromatography. Additionally, 12 is converted to 21 by reaction with vinyltin in the presence of tetrakis(triphenylphosphine)palladium. Terminal olefin 21 is reacted with osmium tetroxide and sodium periodate to give aldehyde 9.

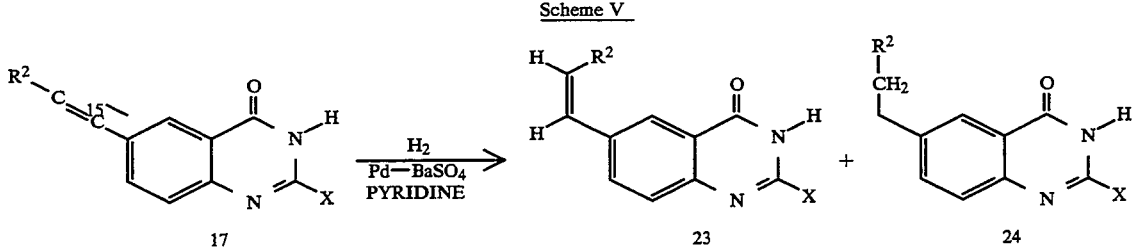

-continued
Scheme V

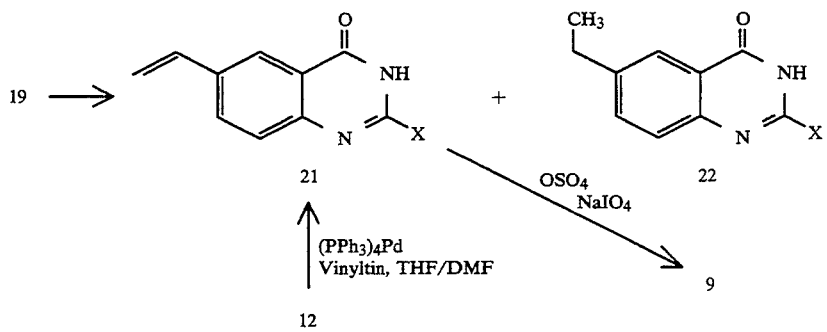

As shown in Scheme VI, olefinated quinazolinones 28 are obtained through Wittig olefination or Wadsworth-Emmons olefination of the aldehyde or ketone 11, wherein $R^1$ is hereinbefore defined provided however that for this reaction scheme $R^1$ cannot be —$OR^7$, —Sph, or —$N(R^7)(R^{13})$, by reaction with 26 or 27 in the presence of base wherein $R^2$ and $R^{10}$ are as defined hereinabove.

As described in EP0497150, biphenyl 37 is attached to quinazolinone intermediate 28 by initially alkylating the quinazolinone with a para-substituted benzyl bromide and subsequently attaching a second phenyl moiety containing a trityl protected tetrazole or a cyano via a transition metal catalyzed coupling at the para positions at the first phenyl ring. Quinazolinone intermediates 21 and 23 are similarly reacted. Alternatively, the coupling of quinazolinone intermediate 28 where X, $R^1$, $R^2$ and $R^{10}$ are hereinbefore defined with biphenyl 37 where $R^{18}$ is a trityl protected tetrazole prepared by the methods of N. B. Mantlo, J. Med. Chem., 34, 2919-2922 (1991), or cyano prepared by the methods outlined in D. J. Carini, J. Med. Chem. 34, 2525-2547 (1991) is illustrated in Scheme VI and gives coupled product 59 by dissolving 28 and 37 in acetone or another suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA), or lithium hexamethyldisilazide for 2–48 hours, at 20°-60° C. The obtained alkylated quinazolinone 59 may be purified by chromatography or used as is in further transformations and/or deprotection. Quinazolinone intermediates 21 and 23 are similarly reacted.

Scheme VI

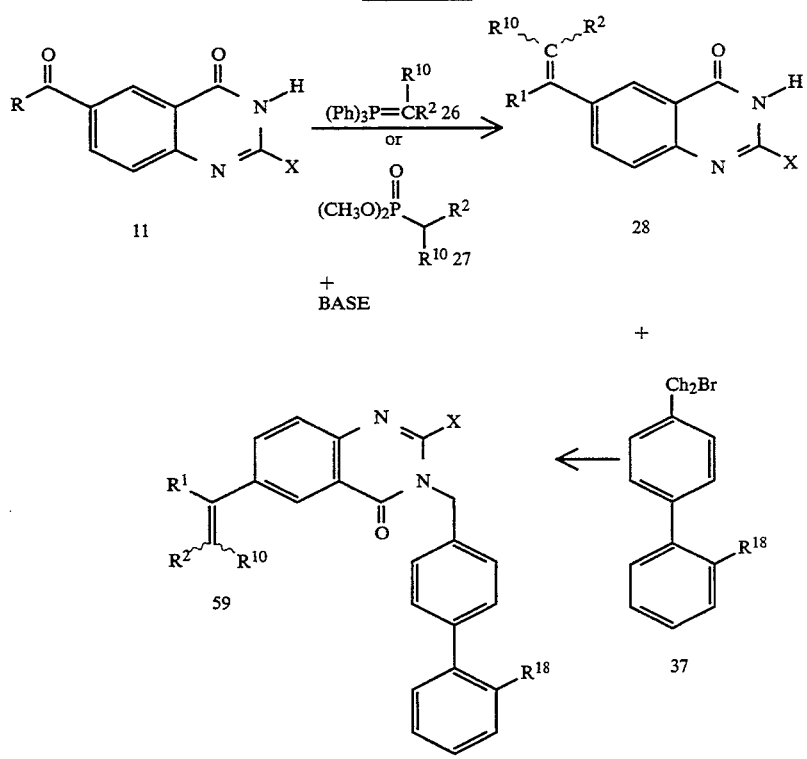

Scheme VII

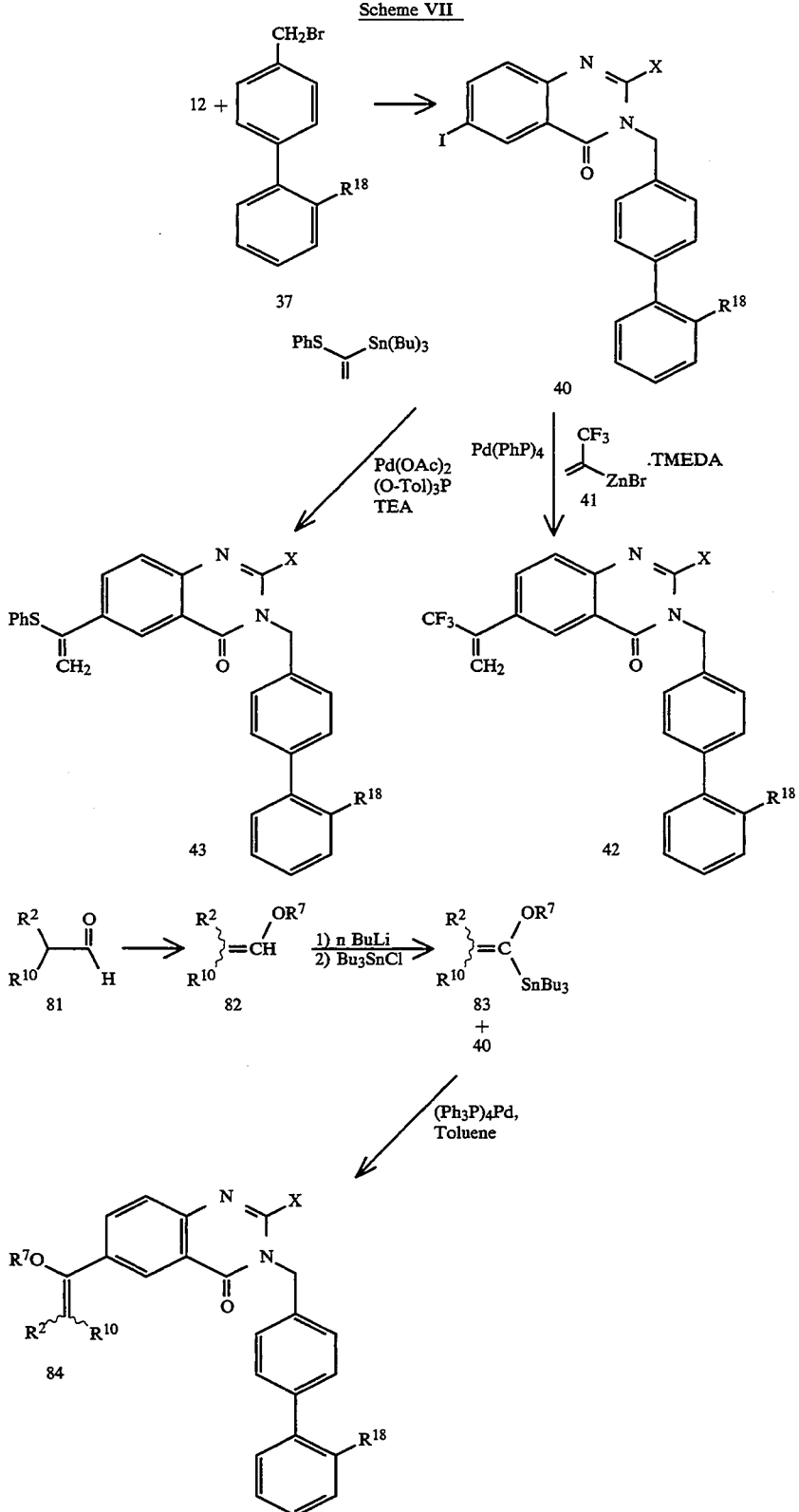

Referring to Scheme VII, alkylated quinazolinone 40 wherein X and R[18] are as defined hereinabove, is formed from intermediate 12 via the methods described for Scheme VI. Alkylated quinazolinone 40 is converted to the trifluoromethyl olefin 42 through palladium catalyzed coupling with trifluoroisopropenylzinc reagent 41 (Jiang, B.; Xu, Y.; *J. Org. Chem.* 56, 7336 (1991)). Additionally, reaction of alkylated quinazolinone 40 with thiophenyl vinyltin using the method of Magnus in *J. Chem. Soc. Chem. Comm.* 522(1977) in the presence of a palladium catalyst as described by Quayle in *Tet. Lett.* 33(3) 413, (1992) gives the vinyl sulfide substituted quinazolinone 43. Alkylated quinazolinone 40 wherein X and $R^{18}$ are as defined hereinabove is converted to 84 by reaction of 40 with 83 wherein $R^2$, $R^7$ and $R^{10}$ are as defined hereinabove provided however that for this reaction scheme $R^7$ cannot be H in the presence of tetra-bis-triphenylphosphinepalladium(o) and toluene. Reagent 83 is formed from 82 wherein $R^2$, $R^7$ and $R^{10}$ are as defined hereinabove provided however that for this reaction scheme $R^7$ cannot be H by reaction with n-BuLi followed by $Bu_3SnCl$. Intermediate 82 wherein $R^2$, $R^7$ and $R^{10}$ are as defined hereinabove provided however that for this reaction scheme $R^7$ cannot be H is obtained from 81 by the methods described in "Advanced Organic Chemistry", March, pp 346, 789, 925.

Scheme VIII describes an alternative route to trifluoromethyl olefin 42. Quinazolinone 9 where X is hereinbefore defined is coupled with biphenyl 37 where $R^{18}$ is hereinbefore defined, using the coupling methods shown in Scheme VII, to give alkylated quinazolinone 44. Reaction of alkylated quinazolinone 44 with trifluoromethyl iodide and zinc in N,N-dimethylformamide gives alcohol 45. Alcohol 45 is oxidized with 1,1,1-triacetoxy-1,1-dihydro-1,2-benziodoxol-3(1H)-one 46 using the method of R. J. Linderman and D. M. Graves, Tet. Lett., 28(37) 4259(1987) to afford ketone 47, Olefin 42 is formed by a Wittig reaction on ketone 47 with Wittig reagent $Ph_3P=CH_2$.

Referring to Scheme IX, quinazolinone 16 where X is hereinbefore defined is coupled with biphenyl 37 where $R^{18}$ is hereinbefore defined, using the coupling methods shown in Scheme VII, to give alkylated quinazolinone 48. Reaction of alkylated quinazolinone 48 with trimethylsilyl cyanide in the presence of zinc iodide (Oda, M.; Yamamuro, A.; Watabe, T., Chem. Lett, 1427 (1979)) gives the trimethylsilylcyanohydrin 49 where $R^{18}$ is the free tetrazole which is further reacted with phosphorous oxychloride or other suitable dehydrating agent, such as $KHSO_4$, $H_2SO_4$, $BF_3$—$OEt_2$, acetic anhydride and the like in pyridine to give the cyano substituted olefin 50. Alkylated quinazolinone 48 where X and $R^{18}$ are hereinbefore defined is reacted with amine $HN(R^7)(R^{13})$, where $R^7$ and $R^{13}$ are as defined hereinabove provided however that for this reaction scheme neither $R^7$ nor $R^{13}$ may be H, with removal of water to give 80.

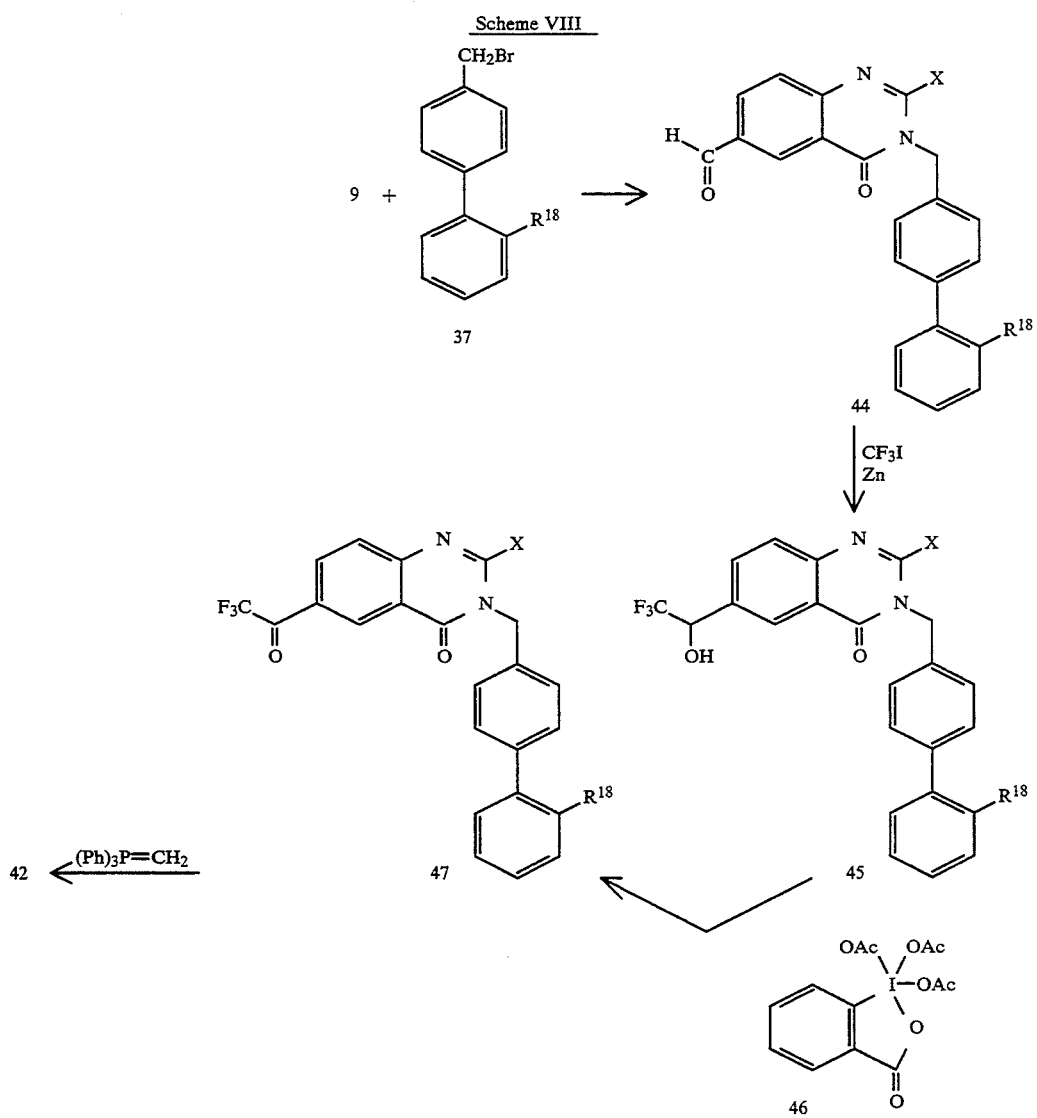

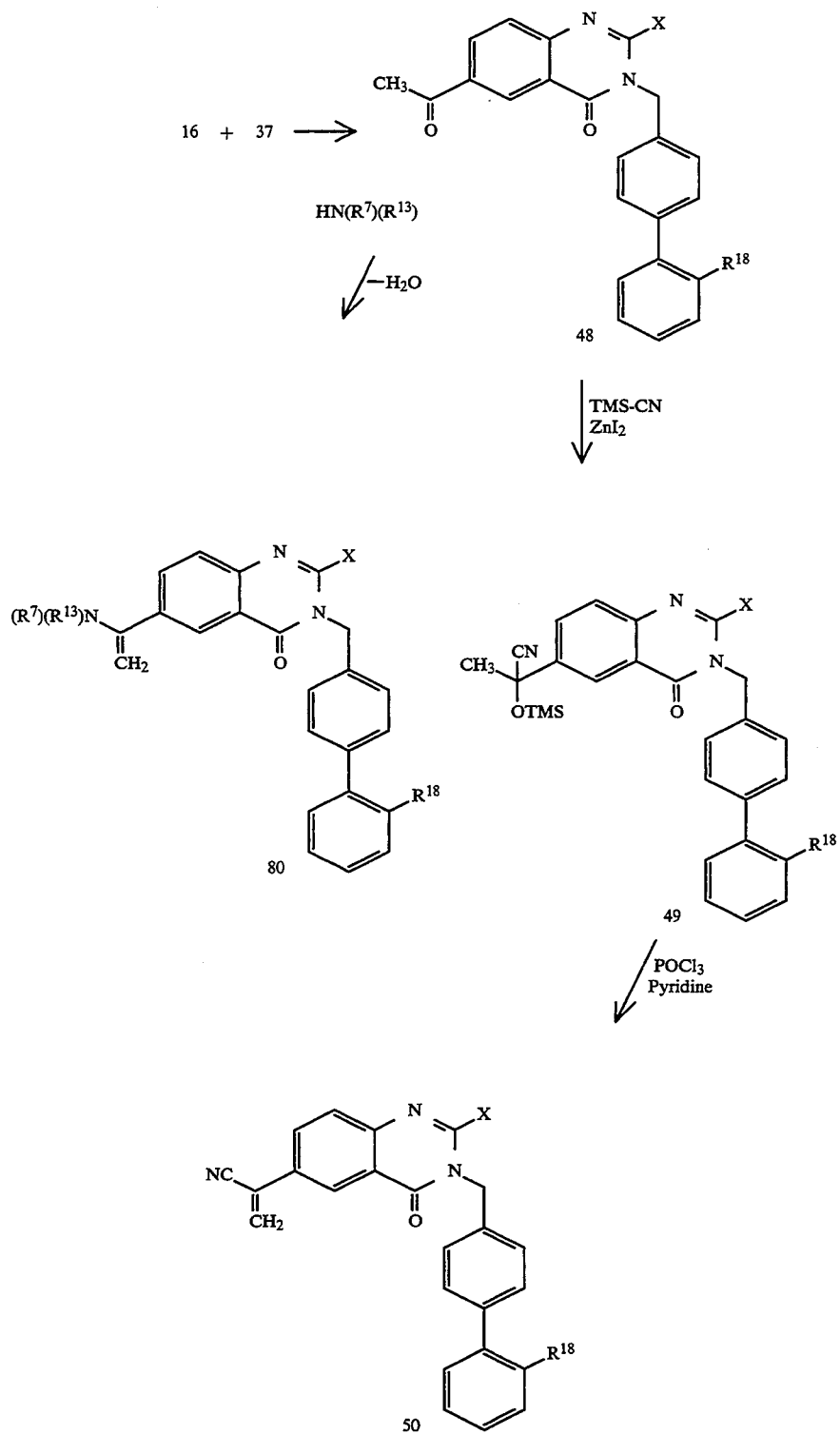

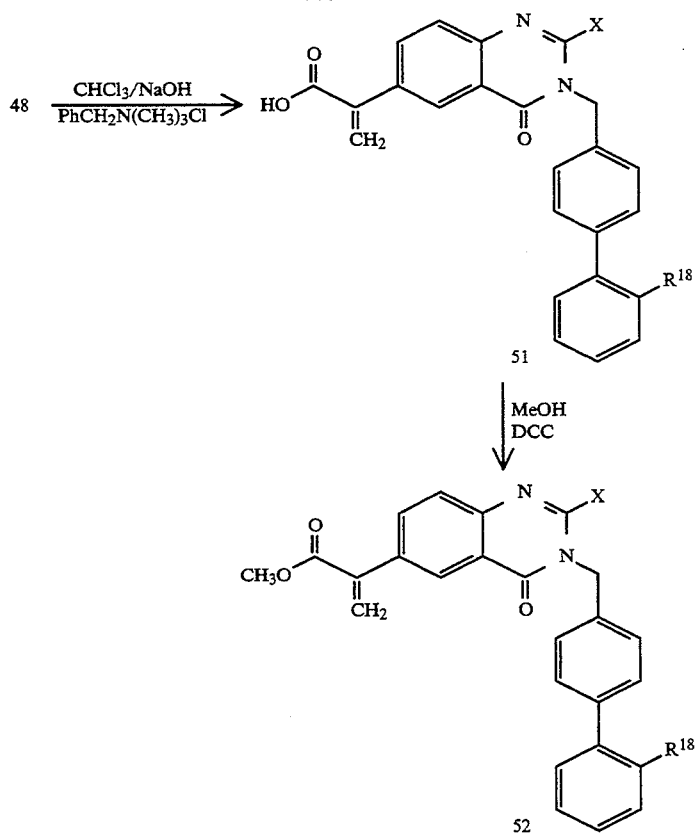

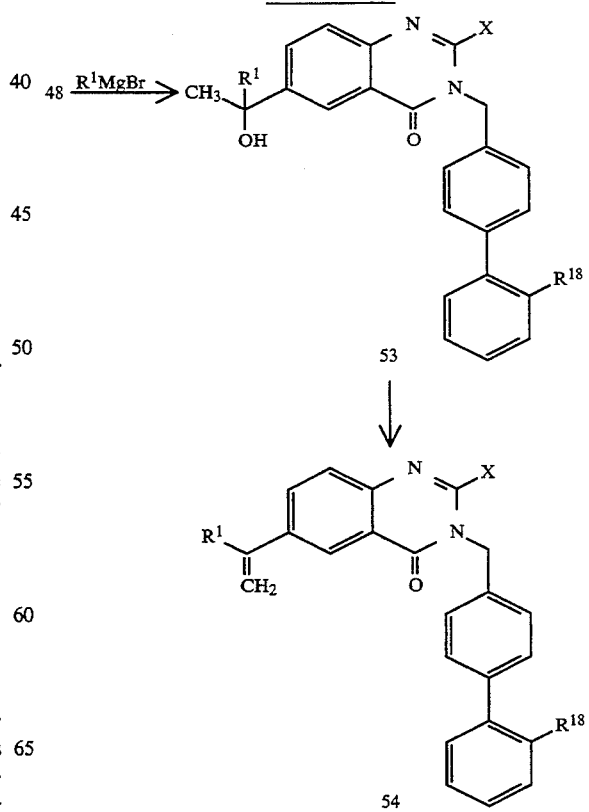

As shown in Scheme X, alkylated quinazolinone 48 is reacted with aqueous sodium hydroxide in the presence of chloroform and benzyltrimethylammonium chloride to give carboxylic acid 51. Additionally, carboxylic acid 51 is reacted with methyl alcohol in the presence of 4-dimethylaminopyridine and dicyclohexylcarbodiimide to afford methyl ester 52.

As shown in Scheme XI, olefin 54 is prepared by the addition of a Grignard reagent $R^1MgBr$, to 48 where $R^1$ is hereinbefore defined provided however that for this reaction scheme $R^1$ cannot contain —$CO_2R^7$, —$CON(R^7)(R^{13})$ or

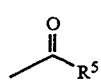

nor can it be H, —$OR^7$, —CN, —$CF_3$, —SPh or —$N(R^7)(R^{13})$ to provide alcohol 53. The alcohol is dehydrated with bis[α,α-bis(trifluoromethyl)benzenemethanolato]diphenylsulfur or with sulfuric, hydrochloric, or p-toluenesulfonic acid to give olefin 54.

The synthesis of α,β-unsaturated esters and amides is illustrated in Scheme XII. Quinazolinone 48 is reacted with enol triflates (Scott, W. J., McMurry, J. E., *Accounts of Chemical Research* 21(2), 47(1988)) to afford 55. Palladium catalyzed coupling of 55 (Cacchi, S.; Morera, E.; Ortar, G., *Tet. Letters*, 26(8), 1109(1985)) with alcohol $R^5OH$, where $R^5$ is hereinabove defined provided however that for this reaction scheme $R^5$ cannot be H, gives ester 56. Palladium catalyzed coupling of 55 with amine $H-N(R^7)(R^{13})$, where $R^7$ and $R^{13}$ are hereinbefore defined, gives amide 57.

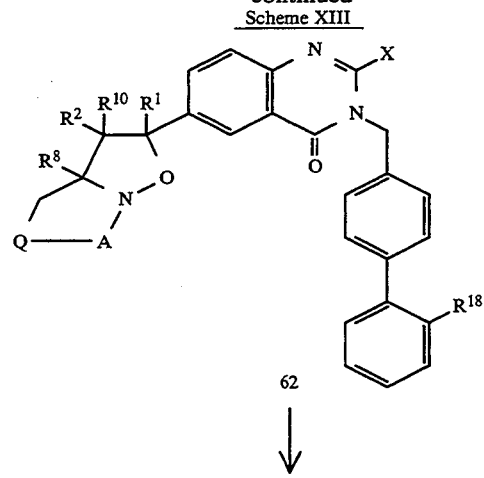

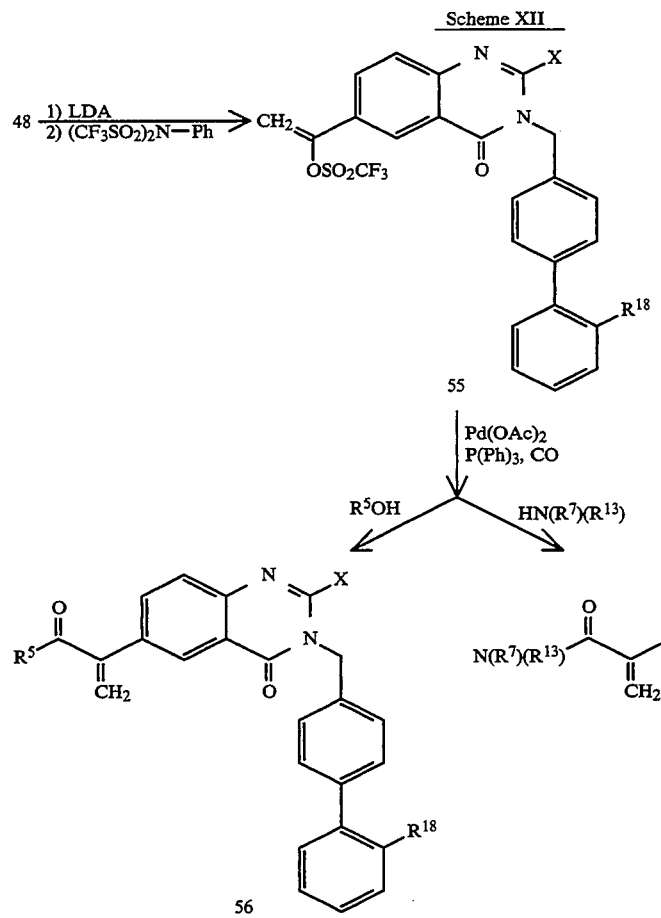

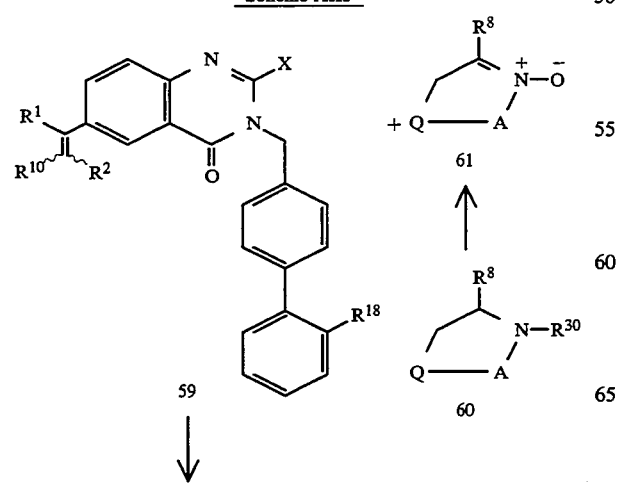

Scheme XIII (-continued)

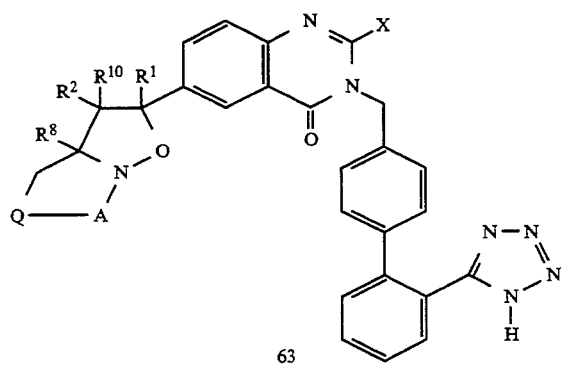

As outlined in Scheme XIII, alkylated quinazolinone 59, where $R^1$, $R^2$, $R^{10}$, $R^{18}$ and X are hereinbefore defined are reacted with nitrone 61 prepared from 60 wherein $R^8$ Q and A are hereinbefore defined and $R^{30}$ is H, by using the hydrogen peroxide-selenium dioxide method of S-I. Murahashi and T. Shiota, *Tet. Letters*, 28(21) 2383(1987), or by oxidation with mercuric oxide in chloroform when $R^{30}$ is OH to give bicyclic derivatives 62. Quinazolinones 42, 43, 50, 52, 54, 56, 57, 80 and 84 are similarly reacted.

Deprotection of the trityl group is accomplished by refluxing an aqueous acetone solution of the alkylated quinazolinone 62 with a catalytic amount of hydrochloric acid or other suitable acid such as sulfuric, trifluoroacetic or hydrogen chloride for 2–24 hours. Additionally, heating 62 in tetrahydrofuran-methanol removes the trityl protecting group and affords 63. Reaction of 62 where $R^{18}$ is cyano with sodium azide in the presence of tri-n-butyltin chloride in refluxing xylene affords the desired tetrazole 63. Contemplated equivalents to tri-n-butyltin chloride include tri-(lower alkyl $C_1$-$C_4$)Tin chlorides and bromides. Contemplated equivalents to sodium azide include potassium azide and lithium azide.

Scheme XIV (-continued)

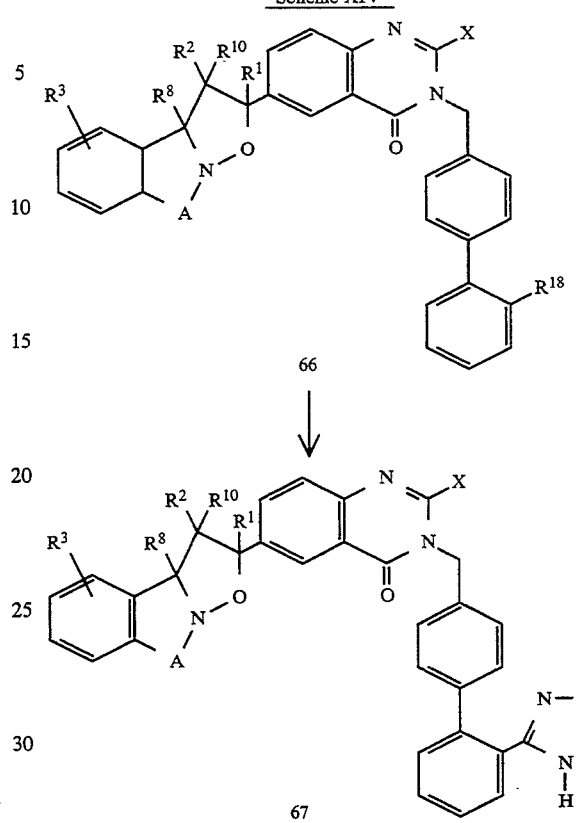

As shown in Scheme XIV, alkylated quinazolinone 59, where $R^1$, $R^2$, $R^{10}$, $R^{18}$ and X are hereinbefore defined is reacted with nitrone 64, prepared from 65 where $R^3$ and $R^8$ are hereinbefore defined and $R^{30}$ is H, by using the hydrogen peroxide-selenium dioxide method of S-I. Murahashi and T. Shiota, *Tet. Letters*, 28(21) 2383(1987) to give tricyclic derivative 66. Quinazolinones 42, 43, 50, 52, 54, 56, 57, 80 and 84 are similarly reacted. Deprotection of the trityl group is accomplished by refluxing an aqueous acetone solution of the alkylated quinazolinone 66 with a catalytic amount of hydrochloric acid or other suitable acid such as sulfuric, trifluoroacetic or hydrogen chloride for 2–24 hours. Additionally, heating 66 in tetrahydrofuran-methanol removes the trityl protecting group and affords 67. Reaction of 66 where $R^{18}$ is cyano with sodium azide in the presence of tri-n-butyltin chloride in refluxing xylene affords the desired tetrazole 67. Contemplated equivalents to tri-n-butyltin chloride include tri-(lower alkyl $C_1$-$C_4$) tin chlorides and bromides. Contemplated equivalents to sodium azide include potassium azide and lithium azide.

Scheme XIV

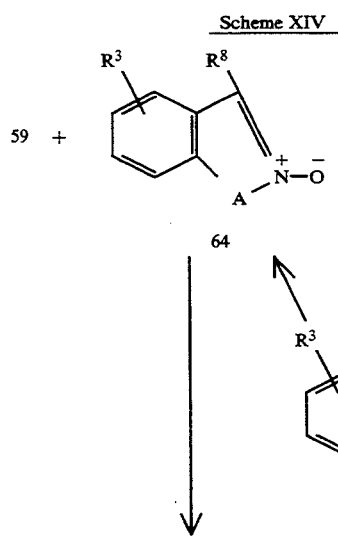

Scheme XV

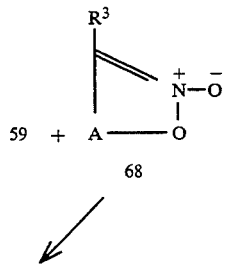

-continued
Scheme XV

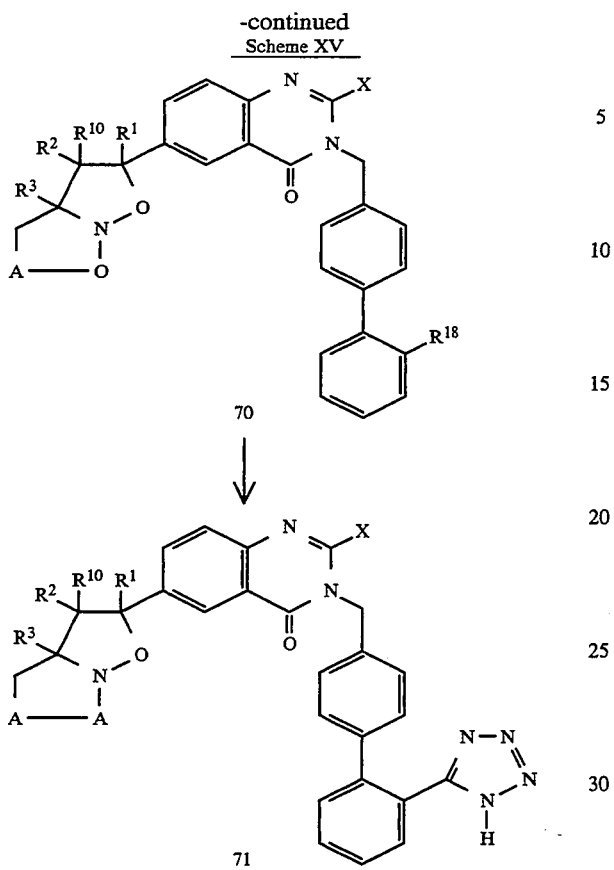

As shown in Scheme XV, alkylated quinazolinone 59, where $R^1$, $R^2$, $R^{10}$, $R^{18}$ and X are hereinbefore defined is reacted with nitronate 68 prepared as described in "Nitrones, Nitronates and Nitroxides", E. Breuer, H. G. Avrich and A. Nielsen, Wiley & Sons, 1989, chapter 1, wherein $R^3$ and A are as hereinbefore defined to give 70. Quinazolinones 42, 43, 50, 52, 54, 56, 57, 80 and 84 are similarly reacted.

Deprotection of the trityl group is accomplished by refluxing an aqueous acetone solution of the alkylated quinazolinone 70 with a catalytic amount of hydrochloric acid or other suitable acid such as sulfuric, trifluoroacetic or hydrogen chloride for 2-24 hours. Additionally, heating 70 in tetrahydrofuran methanol removes the trityl protecting group and affords 71. Reaction of 70 where $R^{18}$ is cyano with sodium azide in the presence of tri-n-butyltin chloride in refluxing xylene affords the desired tetrazole 71. Contemplated equivalents to tri-n-butyltin chloride include tri-(lower alkyl $C_1$-$C_4$)tin chlorides and bromides. Contemplated equivalents to sodium azide include potassium azide and lithium azide.

Scheme XVI

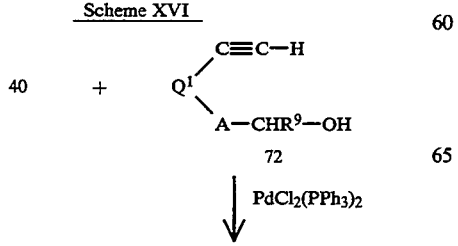

-continued
Scheme XVI

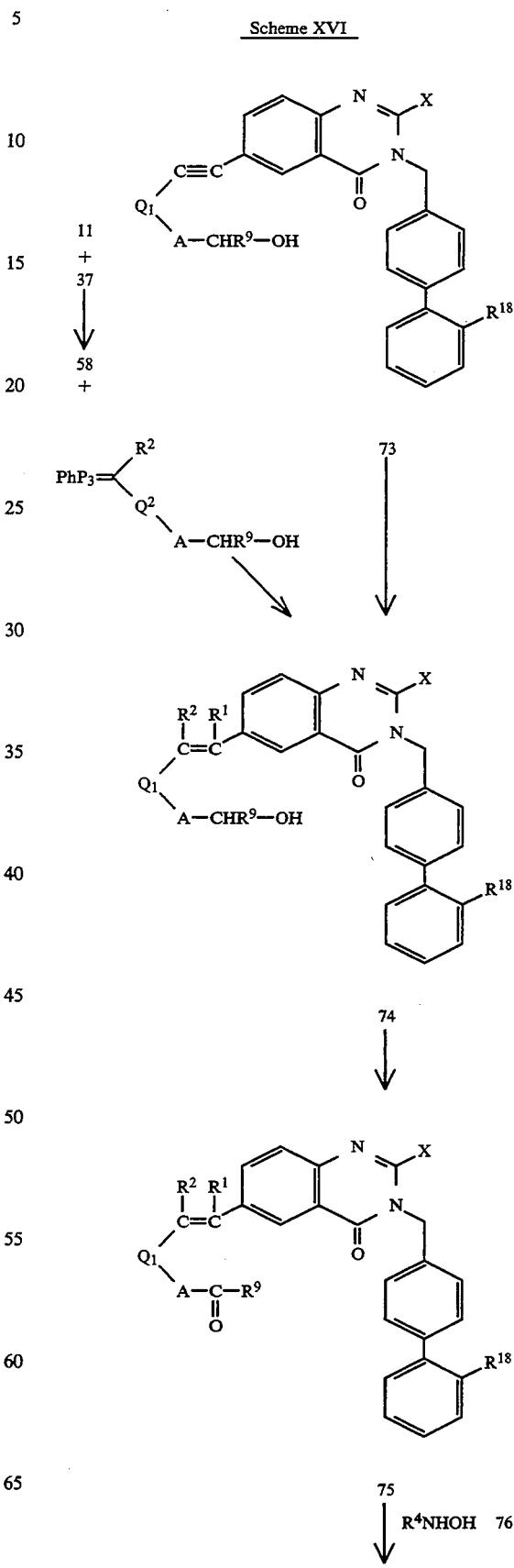

-continued
Scheme XVI

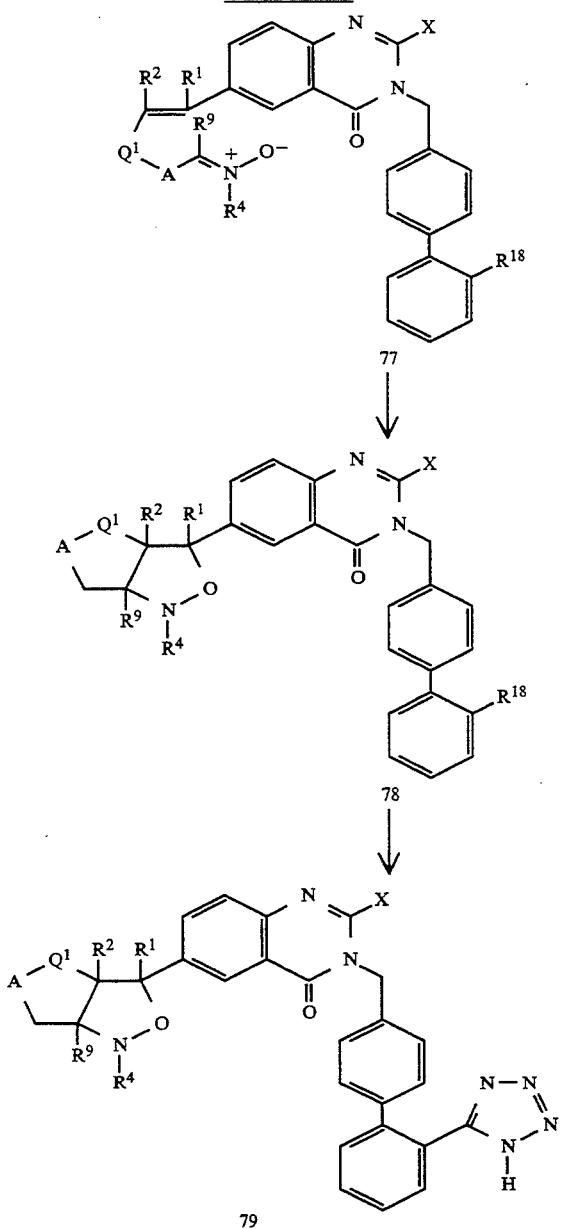

Referring to Scheme XVI, ketone 11 wherein $R^1$ and X are hereinbefore defined is coupled to biphenyl 37 where $R^{18}$ is hereinbefore defined, using the coupling method shown in Scheme VII to give alkylated quinazolinone 58. Quinazolinones 9, 16 and 18 are similarly reacted. Olefin 74 wherein $R^1$, and $R^2$ are as defined hereinbefore may be prepared from ketone 58 via a Wittig reaction with a substituted phosphorane which is prepared by known methods. Olefin 74 is oxidized with pyridinium dichromate to give carbonyl 75 wherein $R^1$, $R^2$, $R^9$, A and $Q^1$ are as defined hereinbefore. Alternatively, alkylated quinazolinone 40, where X and $R^{18}$ are hereinbefore defined, is reacted with acetylene 72, where $Q^1$ and A are hereinbefore defined, in the presence of a palladium(II) catalyst to give alcohol 73. Hydrogenation of 73 gives olefin 74 wherein $R^1$, and $R^2$ are H which is oxidized with pyridinium dichromate to give carbonyl 75 wherein $R^1$ and $R^2$ are H. Reaction of carbonyl 75 with oxime $R^4$NHOH 76 where $R^4$ is hereinbefore defined affords the nitrone 77 which upon heating cyclizes to give bicyclic derivative 78.

Deprotection of the trityl group is accomplished by refluxing an aqueous acetone solution of the alkylated quinazolinone 78 with a catalytic amount of hydrochloric acid or other suitable acid such as sulfuric, trifluoroacetic or hydrogen chloride for 2–24 hours. Additionally, heating 78 in tetrahydrofuran-methanol removes the trityl protecting group and affords 79. Reaction of 78 where $R^{18}$ is cyano with sodium azide in the presence of tri-n-butyltin chloride in refluxing xylene affords the desired tetrazole 79. Contemplated equivalents to tri-n-butyltin chloride include tri-(lower alkyl $C_1$–$C_4$)Tin chlorides and bromides. Contemplated equivalents to sodium azide include potassium azide and lithium azide.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium, magnesium and ammonium salts.

Some of the compounds of the hereinbefore described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation are illustrated by the following non-limiting examples.

EXAMPLE 1

2-Butyl-6-(methyl)-4(1H)-quinazolinone

To 20.0 g of 2-amino-5-methylbenzoic acid is added 60 ml of valeric anhydride. The mixture is heated at reflux for 18 hours and then concentrated under reduced pressure. The resulting brown solid residue is dissolved in a mixture of 200 ml of 30% of ammonium hydroxide solution and 300 ml of ethyl alcohol. This mixture is heated at reflux for 5 hours and then allowed to cool to room temperature. After cooling, the precipitate is collected by filtration. The cake is washed with ethanol and water, then dried under vacuum to give 8.92 g of the quinazolinone as a white solid. CI MASS SPEC MH+=217.

EXAMPLE 2

2-Butyl-6-iodo-4(1H)-quinazolinone

The method of Example 1 is used with 2-amino-5-iodobenzoic acid to prepare the desired product, m.p. 257°–258° C.

EXAMPLE 3

2-Butyl-6-(bromomethyl)-4(1H)-quinazolinone

To a suspension of 3.50 g of 6-methylquinazolone in 100 ml of chloroform is added 3.39 g of N-bromosuccinimide and 0.25 g of benzoyl peroxide. The reaction mixture is heated at reflux for 18 hours and then filtered hot. A precipitate of 2.21 g of an inseparable mixture of the desired bromide and starting 6-methyl-quinazolinone is obtained and used in Example 4 without further purification.

EXAMPLE 4

2-Butyl-6-(hydroxymethyl)-4(1H)-quinazolinone

To a suspension of 2.0 g of impure 2-butyl-6-(bromomethyl)-4(1H)-quinazolinone (from Example 3) in 35 ml of dimethylsulfoxide and 20 ml of water is added 1.0 g of potassium carbonate. The reaction mixture is heated at reflux for 6 hours, resulting in a complete solution. Upon cooling slowly to room temperature a white precipitate forms and is collected by filtration. The filter cake is purified by flash chromatography on silica gel, eluting with 9:1 chloroform-methanol to give 0.67 g of the desired product as a white solid. CI MASS SPEC 233(M+H).

EXAMPLE 5

2-Butyl-1,4-dihydro-4-oxo-6-quinazolinecarboxaldehyde

To a solution of 0.3 g of 2-butyl-6-(hydroxymethyl)-4(1H)-quinazolinone in 3.5 ml of dry N,N-dimethylformamide is added 1.7 g of pyridinium dichromate. The reaction mixture is stirred at room temperature for 16 hours and then poured into 125 ml of water. The resulting precipitate is removed by filtration and the filtrate extracted with 9:1 chloroform-methanol. The combined organic extracts are dried over magnesium sulfate, filtered and concentrated in vacuo and combined with the precipitate above. The combined solids are purified by flash chromatography on silica gel by eluting with 1:1 ethyl acetate-hexanes to give 0.27 g of the desired product. CI MASS SPEC 231(M+H).

EXAMPLE 6

2-Butyl-6-(1-hydroxyethyl)-4(1H)-quinazolinone

To a solution of 0.60 g of 2-butyl-1,4-dihydro-4-oxo-6-quinazolinecarboxaldehyde in 30 ml of dry tetrahydrofuran, cooled to 0° C. is added dropwise, 2.61 ml of a 3.0M solution of methylmagnesium bromide in diethyl ether. The reaction is stirred at 0° C. for 30 minutes and then quenched with 10 ml of aqueous ammonium chloride. After diluting with 10 ml of water, the reaction mixture is extracted with 9:1 chloroform-methanol. The combined extracts are dried with magnesium sulfate, filtered and concentrated to yield 0.64 g of the desired product. CI MASS SPEC 247(MH+).

EXAMPLE 7

2-Butyl-6-(1-hydroxypropyl)-4(1H)-quinazolinone

To a solution of 0.25 g of 2-butyl-1,4-dihydro-4-oxo-6-quinazolinecarboxaldehyde in 10 ml of dry tetrahydrofuran, cooled to 0° C., is added 1.63 ml of 2.0M ethyl magnesium bromide in tetrahydrofuran. The reaction mixture is stirred for 30 minutes at 0° C. and quenched with 20 ml of saturated ammonium chloride solution and 20 ml of water. The reaction mixture is extracted with 9:1 chloroform-methanol, dried over magnesium sulfate, filtered and evaporated in vacuo to give 0.26 g of the desired product. CI MASS SPEC 261(MH+).

EXAMPLE 7

2-Butyl-6-(1-hydroxypropyl)-4(1H)-quinazolinone

To a solution of 0.25 g of 2-butyl-1,4-dihydro-4-oxo-6-quinazolinecarboxaldehyde in 10 ml of dry tetrahydrofuran, cooled to 0° C., is added 1.63 ml of 2.0M ethyl magnesium bromide in tetrahydrofuran. The reaction mixture is stirred for 30 minutes at 0° C. and quenched with 20 ml of saturated ammonium chloride solution and 20 ml of water. The reaction mixture is extracted with 9:1 chloroform-methanol, dried over magnesium sulfate, filtered and evaporated in vacuo to give 0.26 g of the desired product. CI MASS SPEC 261(MH+).

EXAMPLE 8

2-Butyl-1,4-dihydro-4-oxo-6-quinazoline-carboxaldehyde

To a solution of 1.0 g of 2-butyl-6-iodo-4(1H)-quinazolinone and 0.355 g of tetrakis(triphenylphosphine)palladium in 15 ml of tetrahydrofuran and 5 ml of N,N-dimethylformamide, heated to 55° C. under an atmosphere of carbon monoxide is added a solution of 1.40 g of tri-n-butyltin hydride in 2.5 ml of toluene over 6 hours via a syringe pump. After the addition is complete the reaction is allowed to cool to room temperature, diluted with brine and extracted with chloroform. The combined organics are concentrated in vacuo and the resulting residue triturated with ether. The precipitate is collected by filtration and purified by flash chromatography on silica gel, eluting with 1:1 ethyl acetate-hexanes to give 0.35 g of the desired product, m.p. 242°–244° C.

EXAMPLE 9

2-Butyl-6-[(trimethylsilyl)ethylnyl]-4(1H)-quinazolinone

To a solution of 1.0 g of 2-butyl-6-iodo-4(1H)-quinazolinone 0,043 g of bis(triphenylphosphine) palladium (II) chloride and 5.8 mg of copper (I) iodide in 5.0 ml of N,N-dimethylformamide and 5.0 ml of triethylamine is added 0.36 g of (trimethylsilyl)acetylene. The resulting reaction mixture is heated at 45° C. for 1 hour and then 65° C. for 5 hours. Upon cooling, the reaction mixture is concentrated in vacuo and the residue purified by flash chromatography on silica gel, eluting with 1:3 ethyl acetate-hexane to yield 0.75 g of the desired product as a white solid. CI MASS SPEC 299(MH+).

EXAMPLE 10

2-Butyl-6-ethylnyl-4(1H)-quinazolinone

To a solution of 0.70 g of 2-butyl-6-[(trimethylsilyl)ethynyl]-4(1H)-quinazolinone in 20 ml of methanol and 20 ml of tetrahydrofuran is added 10.0 ml of 1.0N sodium hydroxide solution. The reaction is stirred at room temperature for 2 hours and then diluted with 5% hydrochloric acid solution until the pH is 2. The resulting tan precipitate is collected by filtration and dried in vacuo to yield 0.50 g of the desired product. CI MASS SPEC 227(MH+).

EXAMPLE 11

6-Acetyl-2-butyl-4(1H)-quinazolinone

To a solution of 1.20 g of 2-butyl-6-ethynyl-4(1H)-quinazolinone in 90 ml of acetic acid is added 0.45 g of mercuric sulfate, 0.9 ml of water and 0.3 ml of sulfuric acid. The reaction mixture is heated at reflux for 5 hours, cooled to room temperature and quenched with 150 ml of water. The resulting mixture is concentrated in vacuo, diluted with 150 ml of water and extracted with 6:1 chloroform-methanol. The combined organics are dried over magnesium sulfate, filtered and concentrated in vacuo. The residue is purified by flash chromatography on silica gel, eluting with 1:1 ethyl acetate-hexanes to give 0.67 g of the desired product as a white solid. CI MASS SPEC 245(MH+).

EXAMPLE 12

2-Butyl-6-(1-hydroxy-1-methylethyl)4(1H)-quinazolinone

To a solution of 4.00 g of 6-acetyl-2-butyl-4-(1H)-quinazolinone in 250 ml of dry tetrahydrofuran, cooled to 0° C., is added dropwise 16.4 ml of 3.0M methylmagnesium bromide in diethyl ether. The reaction is stirred at 0° C. for 0.5 hours and then allowed to warm to room temperature followed by quenching with 100 ml of saturated ammonium chloride solution. The mixture is diluted with 50 ml of water and extracted with ethyl acetate. The combined organic layers are washed with brine, dried over anhydrous magnesium sulfate, filtered and concentrated in vacuo. The residue is purified by flash chromatography on silica gel, eluting with 100:0.25 chloroform-methanol to give 2.75 g of the desired product as a white solid. CI MASS SPEC 261(MH+).

Example 13

2-Butyl-6-(1-hydroxyethyl)-4(1H)-quinazolinone

To a suspension of 0.102 g of 6-acetyl-2-butyl-4(1H)-quinazolinone in 10.0 ml of ethanol is added 0,015 g of sodium borohydride. The reaction mixture is stirred for 1.5 hours at room temperature and then diluted with 50 ml of water. The aqueous layer is extracted with 5:1 chloroform-methanol and the combined organics dried over magnesium sulfate, filtered and concentrated in vacuo to yield 0.103 g of the desired product. CI MASS SPEC 247(MH+).

EXAMPLE 14

Methyl 2-butyl-1,4-dihydro-4-oxo-6-quinazolinecarboxylate

To a solution of 1.00 g of 2-butyl-6-iodo-4(1H)-quinazolinone and 6.0 ml of triethylamine in 25 ml of methanol and 5 ml of N,N-dimethylformamide is added 0.275 g of bis-(triphenylphosphine)palladium (II) chloride. The reaction mixture is heated at reflux under an atmosphere of carbon monoxide for 16 hours, then allowed to cool and concentrated in vacuo. The residue is purified by flash chromatography on silica gel, eluting with 1:1 ethyl acetate-hexanes to give 0.389 g of the desired product as a white solid. CI MASS SPEC 261(MH+).

EXAMPLE 15

2-Butyl-6-(1-hydroxy-1-methylethyl)-4(1H)-quinazolinone

To a solution of 0,075 g of methyl 2-butyl-1,4-dihydro-4-oxo-6-quinazolinecarboxylate in 5 ml of dry tetrahydrofuran, cooled to 0° C., is added dropwise 0.51 ml of a solution of 3.0M methylmagnesium bromide in diethyl ether. The reaction is stirred at 0° C. for 0.5 hours and then at room temperature for 1 hour followed by quenching with 10 ml of saturated ammonium chloride solution. The resulting reaction mixture is diluted with 10 ml of water and extracted with ethyl acetate. The combined organics are dried over magnesium sulfate, filtered and concentrated in vacuo. The residue is purified by flash chromatography on silica gel, eluting with 100:0.25 chloroform-methanol to yield 0.055 g of the desired product as a white solid, m.p. 190°–192° C.

EXAMPLE 16

2-Butyl-6-(1-methylethenyl)-4(1H)-quinazolinone

To a suspension of 3.66 g of methyltriphenylphosphonium bromide in 30 ml of dry tetrahydrofuran, cooled to −78° C., is added dropwise 5.9 ml of a 1.73M solution of n-butyllithium in hexanes. Following complete addition, the reaction mixture is allowed to warm to room temperature and stirred for 15 minutes, until all the phosphonium bromide is dissolved. The reaction mixture is then recooled to −78° C. and a suspension of 6-acetyl-2-butyl-4(1H)-quinazolinone in 15 ml of dry tetrahydrofuran is added. The reaction is allowed to warm to room temperature and stirred for 24 hours followed by quenching with saturated ammonium chloride solution. After diluting with 10 ml of water, the aqueous layer is extracted with chloroform and the combined organics dried over magnesium sulfate, filtered and concentrated in vacuo. The residue is purified by flash chromatography on silica gel, eluting with 1:2 ethyl acetate-hexanes to give 0.23 g of the desired product as a white solid. CI MASS SPEC 243 (MH+).

EXAMPLE 17

2-Butyl-6-(hydroxyphenylmethyl)-4(1H)-quinazolinone

To a stirred solution of 2.00 g of 2-butyl-1,4-dihydro-4-oxo-6-quinazolinecarboxaldehyde in 100 ml of tetrahydrofuran, cooled at 0° C., is added 13.0 ml of 2.0M phenyllithium and stirring continued for 1 hour. The cooling is removed and the reaction allowed to reach room temperature followed by an additional 30 minutes at room temperature. The reaction is diluted with saturated ammonium chloride solution and extracted with ethyl acetate. The organic layer is dried, evaporated to a residue, which is purified by chromatography on silica gel by elution with 0.25:100 methanol-chloroform to give 0.932 g of the desired product. CI MASS SPEC 309(MH+).

EXAMPLE 18

2-Butyl-6-ethenyl-4(1H)-quinazolinone

A mixture of 2.00 g of 2-butyl-6-ethylnyl-4(1H)-quinazolinone and 0.200 g of 5% palladium-barium sulfate in 100 ml of pyridine is treated with 1 atmosphere of hydrogen at room temperature until 225 ml of hydrogen is used. The reaction mixture is filtered through diatomaceous earth and the cake washed with 100 ml of pyridine and 100 ml of methanol. The combined filtrates are evaporated to a residue which is purified by chromatography on silica gel using 1:2 ethyl acetate-hexanes to afford 0.786 g of the desired product. CI MASS SPEC 229 (MH+).

EXAMPLE 19

2-Butyl-6-ethenyl-4(1H)-quinazolinone

A mixture of 12.28 g of 2-butyl-6-iodo-4(1H)-quinazolinone 0.866 g of tetrakis (triphenylphosphine)-palladium, 0.015 g of 2,6-di-t-butyl-4-methylphenol in 75 ml of toluene and 20 ml of N,N-dimethylformamide is treated with 13.06 g of tri-n-butyl vinyltin followed by heating at reflux for 4 hours. The reaction mixture is cooled and concentrated in vacuo. The residue is diluted with hexanes and filtered. The filter cake is washed with hexanes and the remaining tacky solid dissolved in 100 ml of chloroform-methanol (8:2) and purified by chromato- graphy on silica gel with 1:3 ethyl acetate-hexanes to afford 4.55 g of the desired product as a yellow solid. CI MASS SPEC 229(MH+).

EXAMPLE 20

2-Butyl-6-iodo-3-[[2'-[1-(triphenylmethyl)-1H-tetrazol-5-yl][1,1'-biphenyl]-4-yl]methyl]-4(3H)-quinazolinone A mixture of 5.00 g of 2-butyl-6-iodo-4(1H)-quinazolinone, 16.98 g of 5-[4'-(bromomethyl)[1,1'-biphenyl]-2-yl]-1-(triphenylmethyl)-1H-tetrazole and 0.695 g of lithium methoxide in 60 ml of tetrahydrofuran is heated at reflux for 40 hours. The reaction mixture is cooled, filtered and concentrated in vacuo to a residue which is purified by column chromatography on silica gel by elution with 1:9 ethyl acetate-hexanes to 1:5 ethyl acetate-hexanes to give 6.638 g of the desired product as a solid. FAB mass spec. 805 (M+H).

EXAMPLE 21

6-Acetyl-2-butyl-3-[[2'-[1-(triphenylmethyl)-1H-tetrazol-5-yl][1,1'-biphenyl[-4-yl]methyl]-4(3H)-quinazolinone A suspension of 0.250 g of 6-acetyl-2-butyl-4(1H)-quinazolinone, 0.685 g of 5-[4'-(bromomethyl)-[1,1'-biphenyl]-2-yl]-1-(triphenylmethyl)-1H-tetrazole and 0.424 g of anhydrous potassium carbonate in 25.0 ml of dry acetone is heated at reflux for 16 hours. The reaction mixture is allowed to cool to room temperature, filtered and the filtrate evaporated in vacuo to a residue. The residue is purified by column chromatography on silica gel using 1:3 ethyl acetate-hexanes to give 0.43 g of the desired product as a solid, m.p. 104°-105° C.

EXAMPLE 22

2-Butyl-6-ethenyl-4(1H)-quinazolinone

To a suspension of 15.14 g of methyltriphenylphosphonium bromide in tetrahydrofuran, cooled to −78° C., is slowly added 21.73 ml of 1.95M n-butyllithium in hexanes. The reaction mixture is allowed to warm to room temperature and stirred until all of the phosphonium salt dissolves. This takes approximately 30 minutes. The reaction mixture is cooled to −78° C. and 1.95 g of 2-butyl-1,4-dihydro-4-oxo-6-quinazolinecarboxaldehyde added in one portion as a solid. The reaction mixture is allowed to warm to room temperature and stirred for 18 hours. The reaction mixture is quenched with saturated ammonium chloride, diluted with water and extracted with ethyl acetate. The organic layer is separated, washed with brine, dried with $MgSO_4$ and concentrated in vacuo to a residue which is purified by chromatography on silica gel using 1:3 ethyl acetate-hexanes to give 2.48 g of the desired product as a solid. CI mass spec 229 (M+H).

EXAMPLE 23

2-Butyl-6-(1-hydroxy-1-phenylethyl)-4(1H)-quinazolinone

To a solution of 2.08 g of 6-acetyl-2-butyl-4(1H)-quinazolinone in 80 ml of tetrahydrofuran is added dropwise at room temperature 14.2 ml of 3.0M phenylmagnesium bromide. The reaction mixture is stirred at room temperature overnight then diluted with aqueous ammonium chloride and extracted with chloroform. The organic layer is dried and evaporated in vacuo to a residue which is purified by column chromatography on silica gel by elution with 1:1 ethyl acetate-hexanes to give 0.535 g of the desired product as a solid. CI mass spec (MH+) 323.

EXAMPLE 24

Ethyl 3-(2-butyl-1,4-dihydro-4-oxo-6-quinazolinyl)-2-propenoate

A mixture of 3.202 g of 2-butyl-1,4-dihydro-4-oxo-6-quinazolinecarboxaldehyde and 5.093 g of (carbethoxymethylene)triphenylphosphorane in 50 ml of acetonitrile is heated at reflux for 18 hours. The reaction mixture is cooled and the resulting solid washed with ether and dried to give 1.94 g of the desired product. CI mass spec 301 (MH+)

EXAMPLE 25

2-Butyl-6-ethenyl-3-[[2'-[1-(triphenylmethyl)-1H-tetrazol-5-yl][1,1'-biphenyl]-4-yl]methyl]-4(3H)-quinazolinone To a suspension of 4.49 g of 2-Butyl-6-ethenyl-4(1H)-quinazolinone in 70 ml of dry tetrahydrofuran at room temperature is rapidly added 23.63 g of a 1.0M solution of lithium bis(trimethyl- silyl)amide in tetrahydrofuran. After stirring for 20 minutes at room temperature 21.94 g of 5-(4'-(bromomethyl)-[1,1'-biphenyl]-2-yl]-1-(triphenylmethyl)-1H-tetrazole is rapidly added in one portion and the reaction mixture heated at reflux for 48 hours. After cooling to room temperature, the reaction mixture is concentrated in vacuo to a residue which is purified by chromatography on silica gel by eluting with 1:3 ethyl acetate-hexanes to give 9.58 g of the desired product as a yellow solid. FAB mass spec 705 (M+H).

EXAMPLE 26

2-Butyl-6-(1-hydroxy-1-phenylethyl)-3-[[-2'-[1-(triphenylmethyl)-1H-tetrazol-5-yl][1,1'-biphenyl]-4-yl]methyl-4(3H)-quinazolinone To a suspension of 0.535 g of 2-Butyl-6-(-1-hydroxy-1-phenylethyl)-4(1H)-quinazolinone in 6.5 ml of dry tetrahydrofuran at room temperature is rapidly added 1.99 ml of a 1.0M solution of lithium bis(trimethylsilyl)amide in tetrahydrofuran. After stirring for 20 minutes at room temperature 1.851 g of 5-(4'-(bromomethyl)-[1,1'-biphenyl]-2-yl]-1-(triphenylmethyl)-1H-tetrazole is rapidly added in one portion and the reaction mixture heated at reflux for 48 hours. After cooling to room temperature, the reaction mixture is concentrated in vacuo to a residue which is purified by chromatography on silica gel by eluting with 1:3 ethyl acetate-hexanes to give 0.790 g of the desired product as a solid. FAB mass spec 821 (M+Na).

EXAMPLE 27

2-Butyl-6-(1-methylethenyl)-3-[[2'-[1-(triphenylmethyl)-1H-tetrazol-5-yl][1,1'-biphenyl]-4-yl]methyl-4(3H)-quinazolinone A mixture of 0.207 g of 2-butyl-6-(1-methylethenyl)-4(1H)-quinazolinone, 0.571 g of 5-(4'-(bromomethyl)-[1,1'-biphenyl]-2-yl]-1-(triphenylmethyl)-1H-tetrazole and 0.354 g of potassium carbonate in 20.0 ml of acetone is heated at reflux for 16 hours. The reaction mixture is cooled, filtered and the filtrate concentrated in vacuo to a residue which is purified by column chromatography on silica gel with 1:6 ethyl acetate-hexanes to give 0.220 g of the desired product as a solid. FAB mass spec 719 (M+H).

EXAMPLE 28

2-Butyl-6-(1-phenylethenyl-3-[[2'-[1-(triphenylmethyl)-1H-tetrazol-5-yl][1,1'-biphenyl]-4-yl]methyl]-4(3H)-quinazolinone A mixture of 0.760 g of 2-Butyl-6-(1-hydroxy-1-phenylethyl)-3-[[-2'-[1-(triphenylmethyl)-1H-tetrazol-5-yl][1,1-biphenyl]-4-yl]methyl-4(3H)-quinazolinone and 0.850 g of {bis[alpha,alpha-bis(trifluoromethyl)benzenemethanolato]diphenylsulfur} in 5.0 ml of chloroform is stirred at room temperature for 3 hours. The reaction mixture is diluted with chloroform and washed with 1N sodium hydroxide and water. The organic layer is dried and evaporated in vacuo to a residue which is purified by column chromatography on silica gel by elution with 1:1 ethyl acetate-hexanes to give 0.599 g of the desired product as a solid. FAB mass spec 803 (M+Na).

EXAMPLE 29

Ethyl 3-[2-butyl-3,4-dihydro-4-oxo-3-[[2'-[1-(triphenylmethyl)-1H-tetrazol-5-yl][1,1'-biphenyl]-4-yl]methyl]-6-quinazolinyl]-2-propenoate To a suspension of 1.75 g of ethyl 3-(2-butyl-1,4-dihydro-4-oxo-6-quinazolinyl)-2-propenoate in 25 ml of dry tetrahydrofuran at room temperature is rapidly added 6.70 g of a 1.0M solution of lithium bis(trimethylsilyl)amide in tetrahydrofuran. After stirring for 20 minutes at room temperature 3.899 g of 5-(4'-(bromomethyl)-[1,1'-biphenyl]-2-yl]-1-(triphenylmethyl)-1H-tetrazole is rapidly added in one portion and the reaction mixture heated at reflux for 48 hours. After cooling to room temperature, the reaction mixture is diluted with ethyl acetate and the organic layer washed with 5% HCl, water and brine. The organic layer is dried with MgSO$^4$ and concentrated in vacuo to a residue which is purified by column chromatography on silica gel by eluting with 1:4 ethyl acetate-hexanes to give 1.732 g of the desired product as a solid. FAB mass spec 799 (M+Na).

EXAMPLE 30

2-Butyl-6-(hydroxymethyl)-3-[[2'-[1-(triphenylmethyl)-1H-tetrazol-5-yl][1,1'-biphenyl]-4-yl]methyl-4(3H)-quinazolinone A mixture of 0.198 g of 2-butyl-6-(hydroxymethyl)-4(1H)-quinazolinone, 0.477 g of 5-[4'-(bromomethyl)[1,1'-biphenyl]-2-yl]-1-(triphenylmethyl)-1H-tetrazole and 0.500 g of potassium carbonate in 15.0 ml of dry acetone is heated at reflux for 18 hours. The reaction mixture is allowed to cool to room temperature and evaporated to a residue. The residue is diluted with water and extracted with chloroform. The organic layer is washed with brine, dried with Na$_2$SO$_4$ and evaporated in vacuo to a residue which is purified on thick layer silica gel chromatography plates using 1:1 ethyl acetate-hexanes to give 0.14 g of the desired product. FAB mass spec 709 (M+H).

EXAMPLE 31

2-Butyl-3,4-dihydro-4-oxo-3-[[2'-[1-(triphenylmethyl)-1-tetrazol-5-yl][1,1'-biphenyl]-4-yl]methyl]-6-quinazolinecarboxaldehyde A mixture of 6.48 g of 2-Butyl-6-(hydroxymethyl)-3-[[2'-[1-(triphenylmethyl)-1H-tetrazol-5-yl[]1,1'-biphenyl]-4-yl]methyl-4(3H)-quinazolinone and 5.16 g of pyridinium dichromate in 20 ml of methylene chloride is stirred at room temperature for 18 hours. The reaction mixture is diluted with 100 ml of ether and filtered through a short pad of MgSO$_4$. The filtrate is concentrated in vacuo to give the desired product as a residue. FAB mass spec 729 (M+Na).

EXAMPLE 32

2-Butyl-6-(1-hydroxypropyl)-3-[[2'-[1-(triphenylmethyl)-1H-tetrazol-5-yl][1,1'-biphenyl]-4-yl]methyl]-4(3H)-quinazolinone To a suspension of 1.00 g of 2-Butyl-3,4-dihydro-4-oxo-3-[[2'-[1-(triphenylmethyl)-1H-tetrazol-5yl][1,1'-biphenyl]-4-yl]methyl]-6-quinazolinecarboxaldehyde in 10 ml of tetrahydrofuran, cooled to −78° C. and 2.833 ml of a 1.0M solution of ethylmagnesium bromide rapidly added. The cooling bath is removed and the reaction mixture allowed to warm until a complete solution. The cooling bath is again applied and the reaction mixture cooled to −78° C. and stirred for 0.5 hours. The bath is removed and the reaction mixture allowed to reach room temperature. An aqueous solution of ammonium chloride is added and the reaction mixture extracted with ethyl acetate. The organic layer is dried and concentrated in vacuo to give 0.821 g of the desired product as a solid. FAB mass spec 737 (M+H).

EXAMPLE 33

2-Butyl-6-(1-oxopropyl)-3-[[2'-[1-(triphenylmethyl)-1H-tetrazol-5-yl][1,1'-biphenyl]-4-yl]methyl-4(3H)-quinazolinone A mixture of 0.821 g of 2-Butyl-6-(1-hydroxypropyl)-3-[[2'-[1-(triphenylmethyl)-1H-tetrazol-5-yl][1,1'-biphenyl]-4-yl]methyl-4(3H)quinazolinone and 0.629 g of pyridinium dichromate in 2.5 ml of methylene chloride is stirred at room temperature for 20 hours. The reaction mixture is diluted with ether and filtered through a short pad of MgSO4. The filtrate is concentrated in vacuo to give 0.673 g of the desired product as a solid. FAB mass spec 757 (M+Na).

EXAMPLE 34

2-Butyl-6-(1-methylenepropyl)-3-[[2'-[1-(triphenylmethyl)-1H-tetrazol-5-yl][1,1'-biphenyl]-4-yl]methyl-4(3H)-quinazolinone To a suspension of 1.169 g of methyltriphenylphosphonium bromide in 25 ml of tetrahydrofuran, cooled to −78° C., is slowly added 1.74 ml of 1.88M n-butyllithium in hexanes. The reaction mixture is allowed to warm to room temperature and stirred until all of the phosphonium salt dissolves. This takes approximately 30 minutes. The reaction mixture is cooled to −78° C. and 0.803 g of 2-Butyl-6-(1-oxopropyl)-3-[[2'-[1-(triphenylmethyl)-1H-tetrazol-5-yl][1,1'-biphenyl]-4-yl]methyl-4(3H)-quinazolinone added in one portion as a solid. The reaction mixture is allowed to warm to room temperature and stirred for 18 hours. The reaction mixture is quenched with saturated ammonium chloride, diluted with water and extracted with ethyl acetate. The organic layer is separated, washed with brine, dried with MgSO4 and concentrated in vacuo to a residue which is purified by chromatography on silica gel using 1:3 ethyl acetate-hexanes to give 0.615 g of the desired product as a solid. FAB mass spec 755 (M+Na).

EXAMPLE 35

1-Hydroxy-pyrrolidine

To a stirred solution of 500 ml of ice water and 134 ml of pyrrolidine is added dropwise 230 ml of 30% hydrogen peroxide over 20 minutes with additional ice cooling. When the addition is complete, the external bath is removed and the solution allowed to warm to 35° C. As the solution approaches 35° C. the temperature rapidly reaches 50° C. and external ice bath cooling is necessary. After the exotherm subsides, the cooling bath is removed and the reaction mixture stirred for 18 hours. The aqueous solution is saturated with saturated sodium carbonate and extracted with methylene chloride. The organic layer is dried with NaSO4 and concentrated in vacuo to a residue which is diluted with 50 ml of mineral oil and fractionally distilled to give 36 g of the desired product as a colorless oil which solidifies when refrigerated, B.P. 50°–55°/3 mm.

EXAMPLE 36

3,4-Dihydro-2H-pyrrole 1-oxide

To a solution of 0.300 g of 1-hydroxy-pyrrolidine in 10 ml of chloroform is rapidly added 1.49 g of yellow mercury(II)oxide in one portion as a solid. There is an exotherm. The reaction mixture is stirred for 2 hours at room temperature and an additional 0.39 g of yellow mercury(II)oxide is added. After stirring for an additional 2 hours at room temperature the reaction mixture is filtered, the cake washed with chloroform and the combined filtrates concentrated in vacuo to afford the desired product.

EXAMPLE 37

2,3,4,5-Tetrahydro-pyridine 1-oxide

A mixture of 1.00 g of piperidine, 0.065 g of selenium dioxide and 2.64 ml of 30% hydrogen peroxide in 25.0 ml of acetone is stirred at room temperature for 20 hours. The volatiles are evaporated in vacuo and the residue diluted with water and extracted with chloroform. The organic layer is dried over MgSO4, filtered and evaporated in vacuo to a residue which is purified by column chromatography on silica gel by elution with 9:1 chloroform-methanol to give 0.155 g of the desired product as a solid.

EXAMPLE 38

3,4-Dihydro-isoquinoline 2-oxide

A mixture of 1.00 g of 1,2,3,4-tetrahydroisoquinoline, 0.042 g of selenium dioxide, 2.30 ml of 30% hydrogen peroxide in 20 ml of methanol is stirred at room temperature for 20 hours. The reaction mixture is concentrated in vacuo to a residue which is diluted with water and extracted with chloroform. The organic layer is dried and evaporated in vacuo to a residue which is purified by column chromatography on silica gel by elution with 99:1 methanol-chloroform to give 0.703 g of the desired product as a solid.

EXAMPLE 39

CIS-(+/−)-2-Butyl-6-(hexahydropyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone To a solution of 1.291 g of 2-Butyl-6-ethenyl-3-[[2'-[1-(triphenylmethyl)-1H-tetrazol-5-yl][1,1'-biphenyl]-4-yl]methyl]-4(3H)-quinazolinone in 100 ml of toluene is added 1.5 g of 3,4-Dihydro-2H-pyrrole 1-oxide and the reaction mixture heated at reflux for 6 hours. The reaction mixture is cooled and concentrated in vacuo to a residue which is purified by chromatography on silica gel by elution with 8:1 ethyl acetate-hexanes to give 0.906 g of the desired product as a white foam. FAB mass spec 812 (M+Na).

EXAMPLE 40

Cis-(+/−) 2-Butyl-6-(hexahydro-2-methylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone

EXAMPLE 41

Trans(+/−)-2-Butyl-6-(hexahydro-2-methylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone To a solution of 0.500 g of 2-Butyl-6-(1-methylethenyl)-3-[[2'-[1-(triphenylmethyl)-1H-tetrazol-5yl][1,1'-biphenyl]-4-yl]methyl-4(3H)-quinazolinone in 20 ml of toluene is added 0.600 g of 3,4-Dihydro-2H-pyrrole 1-oxide and the reaction mixture heated at reflux for 7 hours. The reaction mixture is cooled and concentrated in vacuo to a residue which is purified by chromatography on silica gel by elution with 9:1 ethyl acetate-hexanes to give 0.115 g of the first desired product, FAB Mass spec 826 (M+Na), and with further elution 0.248 g of the second desired product. FAB mass spec 826 (M+Na).

EXAMPLE 42

Cis-2-Butyl-6-(hexahydro-2H-isoxazolo[2,3-a]pyridin-2-yl)-3-[[2'-[1-(triphenylmethyl)-1H-tetrazol-5-yl][1,1'-biphenyl]-4-yl]methyl]-4(3H) -quinazolinone

EXAMPLE 43

Trans-2-Butyl-6-(hexahydro-2H-isoxazolo[2,3-a]pyridin-2-yl)-3-[[2'-[1-(triphenylmethyl)-1H-tetrazol-5-yl][1,1'-biphenyl]-4-yl]methyl]-4(3H)-quinazolinone To a solution of 0.500 g of 2-Butyl-6-ethenyl-3-[[2'-[1-(triphenylmethyl)-1H-tetrazol-5-yl[]1,1'-biphenyl]-4-yl]methyl]-4(3H)-quinazolinone in 100 ml of toluene is added 0.291 g of 2,3,4,5-tetrahydropyridine 1-oxide and the reaction mixture heated at reflux for 18 hours. The reaction mixture is cooled and concentrated in vacuo to a residue which is purified by chromatography on silica gel by elution with 1:1 ethyl acetate-hexanes to give 0.160 g of the first desired product as a foam, FAB Mass spec 826 (M+Na), and 0.057 g of the second desired product as a foam. FAB mass spec 826 (M+Na).

EXAMPLE 44

Cis(+/−)-2-Butyl-6-(hexahydro-6,6-dimethylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone To a solution of 0.500 g of 2-Butyl-6-ethenyl-3-[[2'-[1-(triphenylmethyl)-1H-tetrazol-5-yl][1,1'-biphenyl]-4-yl]methyl]-4(3H)-quinazolinone in 25 ml of toluene is added 0.161 g of 5,5-dimethyl-1-pyrroline N-oxide and the reaction mixture heated at reflux for 6 hours. The reaction mixture is cooled and concentrated in vacuo to a residue which is purified by chromatography on silica gel by elution with 2:1 ethyl acetate-hexanes to give 0.332 g of the desired product. FAB mass spec 818 (M+H).

EXAMPLE 45

Ethyl 2-[2-butyl-3,4-dihydro-4-oxo-3-[[2'-[1-(triphenylmethyl)-1H-tetrazol-5-yl][1,1'-biphenyl]-4-yl]methyl]-6-quinazolinyl]hexahydro-pyrrolo[1,2-b]isoxazole-3-carboxylate To a solution of 0.300 g of ethyl 3-[2-butyl-3,4-dihydro-4-oxo-3-[[2'-[1-(triphenylmethyl)-1H-tetrazol-5-yl][1,1'-biphenyl]-4-yl]methyl]-6-quinazolinyl]-2-propenoate in 20 ml of toluene is added 0.293 g of 3,4-dihydro-2H-pyrrole 1-oxide and the reaction mixture heated at reflux for 6 hours. The reaction mixture is cooled and concentrated in vacuo to a residue which is purified by chromatography on silica gel by elution with 1:1 ethyl acetate-hexanes to give 0.177 g of the desired product. FAB mass spec 620 (M+H, -ph3C).

EXAMPLE 46

Cis-2-Butyl-6-(1,5,6,10b-tetrahydro-2H-isoxazolo[3,2-a]isoquinolin-2-yl) -3-[[2'-[1-triphenylmethyl)-1H-tetrazol-5-yl][1,1'-biphenyl]-4-yl]methyl]-4(3H)-quinazolinone To a solution of 0.500 g of ethyl 3-[2-butyl-3,4-dihydro-4-oxo-3-[[2'-[1-(triphenylmethyl)-1H-tetrazol-5-yl][1,1'-biphenyl]-4-yl]methyl]-6-quinazolinyl]-2-propenoate in 25 ml of toluene is added 0.313 g of 3,4-dihydro-isoquinoline 2-oxide and the reaction mixture heated at reflux for 12 hours. The reaction mixture is cooled and concentrated in vacuo to a residue which is purified by chromatography on silica gel by elution with 1:2 ethyl acetate-hexanes to give 0.171 g of the desired product.

FAB mass spec 874(M+H).

EXAMPLE 47

(Cis and Trans) -2-Butyl-6-(1,5,6,10b-tetrahydro-2-methyl-2H-isoxazolo[3,2-a]isoquinolin-2-yl)-3-[[2'-[1-(triphenylmethyl)-1H-tetrazol-5-yl][1,1'-biphenyl]-4-yl]methyl]-4(3H)-quinazolinone To a solution of 0.250 g of 2-Butyl-6-(1-methylethenyl)-3-[[2'-[1-(triphenylmethyl)-1H-tetrazol-5-yl][1,1'-biphenyl]-4-yl]methyl-4(3H)-quinazolinone in 25 ml of toluene is added 0.300 g of 3,4-dihydro-isoquinoline 2-oxide and the reaction mixture heated at reflux for 16 hours. The reaction mixture is cooled and concentrated in vacuo to a residue which is purified by chromatography on silica gel by elution with 1:2 ethyl acetate-hexanes to give 0.201 g of the desired product. FAB mass spec 888 (M+Na).

EXAMPLE 48

2,3,4,5-Tetrahydro-6-methyl-pyridine 1-oxide

A mixture of 1.00 g of methyl piperidine, 0.056 g of selenium dioxide and 2.27 ml of 30% hydrogen peroxide in 20.0 ml of acetone is stirred at room temperature for 20 hours. The volatiles are evaporated in vacuo and the residue diluted with water and extracted with chloroform. The organic layer is dried over MgSO$_4$, filtered and evaporated in vacuo to a residue which is purified by column chromatography on silica gel by elution with 9:1 chloroform-methanol to give 0.201 g of the desired product as a solid.

EXAMPLE 49

Cis-2-Butyl-6-(hexahydro-3a-methyl-2H-isoxazolo[2,3-a]pyridin-2-yl)-3-[[2'-[1-(triphenylmethyl)-1H-tetrazol-5-yl][1,1'-biphenyl]-4-yl]methyl]-4(3H)-quinazolinone To a solution of 0.500 g of 2-Butyl-6-ethenyl-3-[[2'-[1-(triphenylmethyl)-1H-tetrazol-5-yl][1,1'-biphenyl]-4-yl]methyl]-4(3H)-quinazolinone in 25 ml of toluene is added 0.201 g of 2,3,4,5-tetrahydro-6-methyl-pyridine 1-oxide and the reaction mixture heated at reflux for 12 hours. The reaction mixture is cooled and concentrated in vacuo to a residue which is purified by chromatography on silica gel by elution with 1:2 ethyl acetate-hexanes to give 0.108 g of the desired product.

EXAMPLE 50

Cis(+/−)-2-Butyl-6-(hexahydro-2,6,6-trimethylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone

EXAMPLE 51

Trans(+/−)-2-Butyl-6-(hexahydro-2,6,6-trimethylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone To a solution of 0.500 g of 2-Butyl-6-(1-methylethenyl)-3-[[2'-[1-(triphenylmethyl)-1H-tetrazol-5-yl][1,1'-biphenyl]-4-yl]methyl-4(3H)-quinazolinone in 25 ml of toluene is added 0.350 g of 5,5-dimethyl-1-pyrroline N-oxide and the reaction mixture heated at reflux for 7 hours. The reaction mixture is cooled and concentrated in vacuo to a residue which is purified by chromatography on silica gel by elution with 2 ethyl acetate-hexanes to give 0.064 g of the first desired product, FAB Mass spec 854 (M+Na), and with further elution 0.125 g of the second desired product. FAB mass spec 854(M+Na).

EXAMPLE 52

Cis-2-Butyl-6-(hexahydro-2-methyl-2H-isoxazolo[2,3-a]pyridin-2-yl) -3-[[2'-[1-(triphenylmethyl )-1H-tetrazol-5-yl][1,1'-biphenyl]-4-yl]methyl]-4(3H)-quinazolinone

EXAMPLE 53

Trans-2-Butyl-6-(hexahydro-2-methyl-2H-isoxazolo[2,3-a]pyridin-2-yl)-3-[[2'-[1-(triphenylmethyl)-1H-tetrazol-5-yl][1,1'-biphenyl]-4-yl]methyl]-4(3H)-quinazolinone To a solution of 0.500 g of 2-Butyl-6-(1-methylethenyl)-3-[[2'-[1-(triphenylmethyl)-1H-tetrazol-5-yl][1,1'-biphenyl]-4-yl]methyl-4-(3)-quinazolinone in 20 ml of toluene is added 0.350 g of 2,3,4,5-tetrahydropyridine 1-oxide and the reaction mixture heated at reflux for 12 hours. The reaction mixture is cooled and concentrated in vacuo to a residue which is purified by chromatography on silica gel by elution with 1:2 ethyl acetate-hexanes to give 0.141 g of the first desired product, FAB Mass spec 840 (M+Na), and with further elution 0.096 g of the second desired product. FAB mass spec 840 (M+Na).

EXAMPLE 54

Cis-2-butyl-6-(hexahydro-2-phenylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone To a solution of 0.569 g of 2-Butyl-6-(1-phenylethenyl-3-[[2'-[1-(triphenylmethyl)-1H-tetrazol-5-yl][1,1'-biphenyl]-4-yl]methyl]-4(3H)-quinolinone in 25 ml of toluene is added 0.733 g of 3,4-dihydro-2H-pyrrole 1-oxide and the reaction mixture heated at reflux for 17 hours. The reaction mixture is cooled and concentrated in vacuo to a residue which is purified by chromatography on silica gel by elution with 1:1 ethyl acetate-hexanes to give 0.131 g of the desired product. FAB mass spec 866 (M+H).

EXAMPLE 55

Cis-2-butyl-6-(2-ethylhexahydropyrrolo[1,2-b]-isoxazol-2-yl)-3-[[2'-[1-(triphenylmethyl)-1H-tetrazol-5-yl][1,1'-biphenyl]-4-yl]methyl]-4(3H)-quinazolinone

EXAMPLE 56

Trans-2-butyl-6-(2-ethylhexahydropyrrolo[1,2-b]-isoxazol-2-yl)-3-[[2'-[1-(triphenylmethyl)-1H-tetrazol-5-yl][1,1'-biphenyl]-4-yl]methyl]-4(3H)-quinazolinone To a solution of 0.605 g of 2-Butyl-6-(1-methylenepropyl)-3-[[2'-[1-(triphenylmethyl)-1H-tetrazol-5-yl][1,1'-biphenyl]-4-yl]methyl-4(3H)quinazolinone in 30 ml of toluene is added 0.85 g of 3,4-dihydro-2H-pyrrole 1-oxide and the reaction mixture heated at reflux for 16 hours. The reaction mixture is cooled and concentrated in vacuo to a residue which is purified by high pressure liquid chromatography on silica gel by elution with 2:1 ethyl acetate-hexanes to give 0.146 g of the first desired product, FAB Mass spec 840 (M+Na), and 0.284 g of the second desired product. FAB mass spec 840 (M+Na).

EXAMPLE 57

Cis-(+/−)-2-Butyl-6-(hexahydropyrrolo[1,2-b]isoxazol-2-yl)-3-[[2'-(1H-tetrazol-5-yl)[1,1'-biphenyl]-4-yl]methyl]-4(3H)-quinazolinone To a solution of 0.886 g of CIS-(+/−)-2-Butyl-6-(hexahydropyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone dissolved in 2.0 ml of tetrahydrofuran is added 10.0 ml of methanol. The reaction mixture is heated at reflux for 18 hours, cooled and concentrated in vacuo to a residue which is purified by chromatography on silica gel using 9:1 chloroform-methanol to give 0.534 g of the desired product as a white foam. FAB mass spec 548 (M+H).

EXAMPLE 58

Cis-(+/−)-2-Butyl-6-(hexahydro-2-methylpyrrolo[1,2-1,2-b]isoxazol-2-yl) -3-[[2'-(1H-tetrazol-5-yl)[1,1'-biphenyl]-4-yl]methyl]-4(3H)-quinazolinone A solution of 0.082 g of Cis-(+/−)-2-Butyl-6-(hexahydro-2-methylpyrrolo[1,2-b]isoxazol-2-yl)-3-[[2'-[1-(triphenylmethyl)-1H-tetrazol-5-yl][1,1'-biphenyl]4-yl]methyl]-4(3H)-quinazolinone in 2.0 ml of methanol and 0.5 ml of tetrahydrofuran is heated at reflux for 18 hours, cooled, and concentrated in vacuo to a residue which is purified by column chromatography on silica gel by elution with 99:1 to 9:1 chloroform-methanol to give 0.026 g of the desired product as a solid. FAB mass spec 562 (M+N).

EXAMPLE 59

Trans-2-Butyl-6-(hexahydro-2-methylpyrrolo[1,2-b]isoxazol-2-yl)-3-[[2'-(1H-tetrazol-5-yl)[1,1'-biphenyl]-4-yl]methyl]-4(3H)-quinazolinone A solution of 0.248 g of trans-2-butyl-6-(hexahydro-2-methylpyrrolo-[1,2-b]isoxazol-2-yl)-3-[[2'-[1-(triphenylmethyl)-1H-tetrazol-5-yl][1,1'-biphenyl]-4-yl]methyl]-4(3H)-quinazolinone, 5.0 ml of methanol and 1.0 ml of tetrahydrofuran is heated at reflux for 18 hours, cooled, and concentrated in vacuo to a residue which is purified by column chromatography on silica gel by elution with 9:1 chloroform-methanol to give 62 mg of the desired product as a solid. FAB mass spec 562 (M+H).

EXAMPLE 60

(Cis)-2-Butyl-6-(hexahydro-2H-isoxazolo[2,3-a]pyridin-2-yl)-3-[[2'-(1H-tetrazol-5-yl)-[1,1'-biphenyl]-4-yl]methyl]-4(3H)-quinazolinone A solution of 0.148 g of (Cis)-2-butyl-6-(hexahydro-2H-isoxazolo[2,3-a]pyridin-2-yl)-3-[[2'-[1-(triphenylmethyl)-1H-tetrazol-5-yl][1,1'-biphenyl]-4yl]methyl]-4(3H)-quinazolinone in 5.0 ml of methanol and 1.0 ml of tetrahydrofuran is heated at reflux for 4 hours. The volatiles are evaporated in vacuo to a residue which is purified by column chromatography on silica gel by elution with 99:1 to 9:1 chloroform-methanol to give 0.065 g of the desired product as a solid. FAB mass spec 562 (M+H).

EXAMPLE 61

(Cis)-2-Butyl-6-(hexahydro-6,6-dimethylpyrrolo[1,2-b]isoxazol-2-yl)-3-[[2'-(1H-tetrazol-5-yl)[1,1'-biphenyl]-4-yl]methyl]-4(3H)-quinazolinone A solution of 0.320 g of (Cis)-2-butyl-6-(hexahydro-6,6-dimethylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone in 5.0 ml of methanol and 1.0 ml of tetrahydrofuran is heated at reflux for 18 hours. The volatiles are evaporated in vacuo to a residue which is purified by column chromatography on silica gel by elution with 99:1 to 1 chloroform-methanol to give 0.194 g of the desired product as a solid. FAB mass spec 576 (M+H).

EXAMPLE 62

Ethyl 2-[2-butyl-3,4-dihydro-4-oxo-3-[[2'-(1H-tetrazol-5-yl)[1,1'-biphenyl]-4-yl]methyl]-6quinazolinyl]hexahydro-pyrrolo[1,2-b]isoxazole3-carboxylate A solution of 0.174 g of ethyl 2-[2-butyl-3,4-dihydro-4-oxo-3-[[2'-[1-(triphenylmethyl)-1H-tetrazol-5-yl][1,1'-biphenyl]-4-yl]methyl]-6-quinazolinyl]hexahydro-pyrrolo[1,2-b]isoxazole-3-carboxylate in 2.0 ml of ethanol and 1.0 ml of chloroform containing 2.0 ml of 3M HCl in ethyl acetate is stirred at room temperature for 1 hour. The volatiles are evaporated in vacuo to a residue which is purified by column chromatography on silica gel by elution with 9:1 chloroform-methanol to give 0.063 g of the desired product as a solid. FAB Mass spec 620 (M+H).

EXAMPLE 63

Cis-2-Butyl-6-(1,5,6,10b-tetrahydro-2H-isoxazolo[3,2-a]isoquinolin-2-yl)-3-[[2'-(1H-tetrazol5-yl)[1,1'-biphenyl]-4-yl]methyl]-4(3H)-quinazolinone A solution of 0.134 g of Cis-2-butyl-6-(1,5,6,10b-tetrahydro-2H-isoxazolo[3,2-a]isoquinolin-2-yl)-3-[[2'-[1-(triphenylmethyl)-1H-tetrazol-5-yl][1,1'-biphenyl]-4-yl]methyl]-4(3H)-quinazolinone in 2.5 ml of methanol and 0.5 ml of tetrahydrofuran is heated at reflux for 18 hours. The volatiles are evaporated in vacuo to a residue which is purified by column chromatography on silica gel by elution with 99:1 chloroform-methanol to give 0.082 g of the desired product as a solid. FAB mass spec 610 (M+H).

EXAMPLE 64

Cis and Trans-2-Butyl-6-(1,5,6,10b-tetrahydro-2-methyl-2H-isoxazolo[3,2-a]isoquinolin-2-yl)-3-[[2'-(1H-tetrazol-5-yl][1,1'-biphenyl]-4-yl]methyl]-4(3H)-quinazolinone A solution of 0.185 g of Cis and Trans-2-Butyl-6-(1,5,6,10b-tetrahydro-2-methyl-2H-isoxazolo[3,2-a]isoquinolin-2-yl)-3-[[2'-[1-(triphenyl-methyl)-1H-tetrazol-5-yl][1,1'-biphenyl]-4-yl]methyl]-4(3H-quinazolinone in 5.0 ml of methanol and 1.0 ml of tetrahydrofuran is heated at reflux for 18 hours. The volatiles are evaporated in vacuo to a residue which is purified by column chromatography on silica gel by elution with 9:1 chloroform-methanol to give 0.118 g of the desired product as a solid. FAB mass spec 624 (M+H).

EXAMPLE 65

Cis-2-Butyl-6-(hexahydro-3a-methyl]-2H-isoxazolo[2,3-a]pyridin-3-yl)-3-[[2'-(1H-tetrazol-5-yl)[1,1'-biphenyl]-4-yl]methyl]-4(3H)-quinazolinone A solution of 0.089 g of Cis-2-butyl-6-(hexahydro-3a-methyl-2H-isoxazolo[2,3-a]pyridin-2-yl)-3-[[2'-[1-(triphenylmethyl)-(1H-tetrazol-5-yl)[1,1'-biphenyl]-4-yl]methyl]-4(3H)-quinazolinone in 2.5 ml of methanol and 0.5 ml of tetrahydrofuran is heated at reflux for 16 hours. The volatiles are evaporated in vacuo to a residue which is purified by column chromatography on silica gel by elution with 99:1 chloroform-methanol to give 0.046 g of the desired product as a solid. FAB mass spec 576 (M+H).

EXAMPLE 66

Cis-2-Butyl-6-(hexahydro-2,6,6-trimethylpyrrolo[1,2-b]isoxazol-2-yl)-3-[[2'-(1H-tetrazol-5-yl)[1,1'-biphenyl]-4-yl]methyl]-4(3H)-quinazolinone A solution of 0.097 g of Cis-2-butyl-6-(hexahydro-2,6,6-trimethylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone in 2.5 ml of methanol and 0.5 ml of tetrahydrofuran is heated at reflux for 18 hours. The volatiles are evaporated in vacuo to a residue which is purified by column chromatography on silica gel by elution with 99:1 chloroform-methanol to give 0.018 g of the desired product as a solid. FAB mass spec 590 (M+H).

EXAMPLE 67

Cis-2-Butyl-6-(hexahydro-2-methyl-2H-isoxazolo[2,3-a]pyridin-2-yl)-3-[[2'-(1H-tetrazol-5-yl)[1,1'-biphenyl]-4-yl]methyl]-4(3H)-quinazolinone To a solution of 0.131 g of Cis-2-butyl-6-(hexahydro-2-methyl-2H-isoxazolo[2,3-a]pyridin-2-yl)-3-[[2'-[1-(triphenylmethyl)-1H-tetrazol-5-yl][1,1'-biphenyl]-4-yl]methyl]-4(3H)-quinazolinone in 5.0 ml of methanol and 1.0 ml of tetrahydrofuran is heated at reflux for 18 hours. The volatiles are evaporated in vacuo to a residue which is purified by column chromatography on silica gel by elution with 99:1 chloroform-methanol to give 0.083 g of the desired product as a solid. FAB mass spec 576 (M+H).

EXAMPLE 68

Trans-2-Butyl-6-(hexahydro-2-methyl-2H-isoxazolo[2,3-a]pyridin-2-yl)-3-[[2'-(1H-tetrazol-5-yl)[1,1'-biphenyl]-4-yl]methyl]-4(3H)-quinazolinone A solution of 0.087 g of Trans-2-butyl-6-(hexahydro-2-methyl-2H-isoxazolo[2,3-a]pyridin-2-yl)-3-[[2'-[1-(triphenylmethyl)-1H-tetrazol-5-yl][1,1'-biphenyl]-4-yl]methyl]-4(3H)-quinazolinone in 5.0 ml of methanol and 1.0 ml of tetrahydrofuran is heated at reflux for 5 hours. The volatiles are evaporated in vacuo to a residue which is purified by column chromatography on silica gel by elution with 99:1 chloroform-methanol to give 0.057 g of the desired product as a solid. FAB mass spec 576 (M+H).

EXAMPLE 69

Trans-2-Butyl-6-(hexahydro-2,6,6-trimethylpyrrolo[1,2-b]isoxazol-2-yl)-3-[[2'-(1H-tetrazol-5-yl)[1,1'-biphenyl]-4-yl]methyl]-4(3H)-quinazolinone A solution of 0.115 g of Trans-2-butyl-6-(hexahydro-2,6,6-trimethylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone in 5.0 ml of methanol and 1.0 ml of tetrahydrofuran is heated at reflux for 16 hours. The volatiles are evaporated in vacuo to a residue which is purified by column chromatography on silica gel by elution with 99:1 chloroform-methanol to give 0.069 g of the desired product as a solid. FAB mass spec 590 (M+H).

EXAMPLE 70

Cis-2-butyl-6-(hexahydro-2-phenylpyrrolo-[1,2-b]isoxazol-2-yl)-3-[[2'-(1H-tetrazol-5-yl)[1,1'-biphenyl]-4-yl]methyl]-4(3H)-quinazolinone A solution of 0.105 g of Cis-2-butyl-6-(hexahydro-2-phenylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone in 5.0 ml of methanol and 1.0 ml of tetrahydrofuran is heated at reflux for 18 hours. The volatiles are evaporated in vacuo to a residue which is purified by column chromatography on silica gel by elution with 99:1 chloroform-methanol to give 0.047 g of the desired product as a solid. FAB mass spec 624 (M+H).

EXAMPLE 71

Cis-2-butyl-6-(2-ethylhexahydropyrrolo[1,2b]isoxazol-2-yl)-3-[[2'-[1-(1H-tetrazol-5-yl)][1,1'-biphenyl]-4-yl]methyl]-4(3H)-quinazolinone To a solution of 0.073 g of Cis-2-butyl-6-(2-ethylhexahydropyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone in 5.0 ml of methanol and 1.0 ml of tetrahydrofuran is heated at reflux for 16 hours. The volatiles are evaporated in vacuo to a residue which is purified by column chromatography on silica gel by elution with 9:1 chloroform-methanol to give 0.037 g of the desired product as a solid. FAB mass spec 576 (M+H).

EXAMPLE 72

Trans-2-butyl-6-(2-ethylhexahydropyrrolo[1,2-b]isoxazol-2-yl)-3-[[2'-(1H-tetrazol-5-yl)[1,1'-biphenyl]-4-yl]methyl]-4(3H)-quinazolinone To a solution of 0.266 g of Trans-2-butyl-6-(2-ethylhexahydropyrrolo[1,2-b]-isoxazol-2-yl)-3-[[2'-[1-(triphenylmethyl)-1H-tetrazol-5-yl][1,1'-biphenyl]-4-yl]methyl]-4(3H)-quinazolinone in 5.0 ml of methanol and 1.0 ml of tetrahydrofuran is heated at reflux for 16 hours. The volatiles are evaporated in vacuo to a residue which is purified by column chromatography on silica gel by elution with 9:1 chloroform-methanol to give 0.097 g of the desired product as a solid. FAB mass spec 576 (M+H).

EXAMPLE 73

Cis-2-Butyl-6-(hexahydro-2-methylpyrrolo[1,2-b]isoxazol-2-yl)-3-[[2'-(1H-(tetrazol-5-yl)[1,1'-biphenyl-4-yl]methyl]-4(3H)-quinazolinone sodium salt A solution of 0.597 g of Cis-2-butyl-6-(hexahydro-2-methylpyrrolo[1,2-b]isoxazol-2-yl)-3-[[2'-(1H-(tetrazol-5-yl)[1,1'-biphenyl]-4-yl]methyl]-4(3H)-quinazolinone and 1.064 ml of 1N sodium hydroxide in 10 ml of methyl alcohol is stirred at room temperature for 1 hour. The volatiles are evaporated in vacuo to a solid which is dried to give 0.62 g of the desired product. FAB mass spec 584 (M+H).

EXAMPLE 74

Cis-2-Butyl-6-(hexahydro-2-methylpyrrolo[1,2-b]isoxazol-2-yl)-3-[[2'-[1-(triphenylmethyl)-1H-tetrazol-5-yl][1,1'-biphenyl]-4-yl]methyl]-4(3H)quinazolinone To a suspension of 0.050 g of Cis-2-Butyl-6-(hexahydro-2,6,6-trimethylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone sodium salt in 2.5 ml of methylene chloride containing 13 ul of triethylamine is added 0.025 g of triphenylmethyl chloride and the reaction mixture heated at reflux for 2 hours. The cooled reaction mixture is diluted with water and extracted with methylene chloride. The organic extract is dried over MgSO$_4$ and evaporated in vacuo to a residue which is purified by column chromatography on silica gel using ethyl acetate to give 0.053 g of the desired product as a solid. FAB mass spec 826 (M+Na).

EXAMPLE 75

2-Butyl-3,4-dihydro-α-methylene-4-oxo-3-[[2'-[1-(triphenylmethyl)-1H-tetrazol-5-yl][1,1'-biphenyl]-4-yl]methyl-6-quinazolineacetic acid To a stirred mixture of 1.00 g of 6-acetyl-2-butyl-3-[[2'-[1-(triphenylmethyl)-1H-tetrazol-5-yl][1,1'-biphenyl]-4-yl]methyl]-4(3H)-quinazolinone, 0.50 ml of water, 0.345 g of benzyltrimethylammonium chloride, 0.345 g of sodium hydroxide, 3 mg of benzyl alcohol and 4.0 ml of methylene chloride is added 0.414 ml of chloroform via a syringe pump over 6 hours. The reaction mixture is stirred at room temperature. The reaction mixture is diluted with 5% HCl and extracted with chloroform. The organic layer is dried with Na$_2$SO$_4$ and evaporated to a residue which is purified by column chromatography on silica gel by elution with 2:1 ethyl acetatehexanes to give 0.115 g of the desired product. FAB mass spec 771 (M+Na).

EXAMPLE 76

Methyl 2-butyl-α-methylene-3-[[2'-[1-(triphenylmethyl)-1H-tetrazol-5-yl][1,1'-biphenyl]-4-yl]-methyl-6-quinazoline acetate To a solution of 0.100 g of 6-acetyl-2-butyl-3-[[2'-[1-(triphenylmethyl)-1H-tetrazol-5-yl][1,1'-biphenyl]-4-yl]methyl]-4(3H)-quinazolinone, 0.013 g of 4-dimethylaminopyridine in 2.0 ml of methylene chloride and 0.055 ml of methanol, cooled to 0° C. is added 0.030 g of dicyclohexylcarbodiimide as a solid. The reaction mixture is allowed to warm to room temperature and stirred for 18 hours. The reaction mixture is quenched with 5% HCl and extracted with methylene chloride. The organic layer is washed with 5% HCl, water and saturated sodium bicarbonate. The organic layer is dried with Na$_2$SO$_4$ and evaporated to a residue. The residue is purified by column chromatography on silica by elution with 1:4 ethyl acetate-hexanes to give 0.052 g of the desired product. FAB mass spec 785 (M+Na).

EXAMPLE 77

Trans-methyl-2-[2-butyl-3,4-dihydro-4-oxo-[[2'-[1-(triphenylmethyl)-1H-tetrazol-5-yl][1,1'-biphenyl]-4-yl]methyl]-6-quinazolinyl]hexahydropyrrolo-[1,2-b]isoxazole-2-carboxylate A solution of 1,781 g of methyl 2-butyl-α-methylene-3-[[2'-[1-(triphenylmethyl)-1H-tetrazol-5-yl][1,1'-biphenyl]-4-yl]methyl-6-quinazoline acetate, 1.78g of 3,4-dihydro-2H-pyrrole 1-oxide in 150 ml of chloroform is heated at reflux for 1.5 hours. The volatiles are evaporated to a residue which is purified by column chromatography on silica gel by elution with 1:2, 1:1 and 2:1 ethyl acetate-hexanes to give 1.491 g of the desired product. FAB mass spec 848 (M+H).

EXAMPLE 78

Trans(+/−)-Methyl-2-[2-butyl-3,4-dihydro-4-oxo-3-[[2'-(1H-tetrazol-5-yl)[1,1'-biphenyl]-4-yl]methyl-6-quinazolinyl]hexahydropyrrolo[1,2-b]isoxazole-2-carboxylate A mixture of 0.100 g of (trans-methyl-2-[2-butyl-3,4--dihydro-4-oxo-[[2'-[1-(triphenylmethyl)-1H-tetrazol-5-yl][1,1'-biphenyl]-4-yl]methyl]-6-quinazolinyl]hexahydropyrrolo-[1,2-b]isoxazole-2-carboxylate in 2.0 ml of 3M HCl in ethyl acetate and 2.0 ml of ether is stirred at room temperature for 15 minutes. The reaction mixture is diluted with 2 ml of 1:1 ether-hexanes and the resulting solid filtered and dried to give 0.075 g of the desired product as a solid. FAB mass spec 606 (M+H).

EXAMPLE 79

(Trans)-2-butyl6-[hexahydro-2-(hydroxymethyl)-Pyrrolo[1,2-b]isoxazol-2-yl]-3-[[2'-[1-(triphenylmethyl)-1H-tetrazol-5-yl][1,1'-biphenyl]-4-yl]methyl-4(3H)-quinazolinone To a suspension of 0.034 g of lithium aluminum hydride in 3.0 ml of tetrahydrofuran, cooled to −78° C. is added a solution of 0.25 g of transmethyl-2-[2-butyl-3,4--dihydro-4-oxo-[[2'-[1-(triphenylmethyl)-1H-tetrazol-5-yl][1,1'-biphenyl]-4-yl]-methyl]-6-quinazolinyl]hexahydropyrrolo-[1,2-b]isoxazole-2-carboxylate dissolved in 2.0 ml of tetrahydrofuran. The reaction mixture is stirred for 2 hours at −78° C. and then an additional 0.021 g of lithium aluminum hydride is added. The reaction is stirred for an additional four hours at −78° C. and then quenched by the sequential addition of 55 ul of water and 55 UL of 15% sodium hydroxide and 165 UL of water. The resulting mixture is filtered and the precipitate is washed with tetrahydrofuran and chloroform. The filtrate is concentrated in vacuo and the residue is chromatographed on silica gel eluting with 2:1 ethyl acetate-hexanes to give 0.126 g of the desired product as a white form. FAB Mass Spec 842 (M+Na)

EXAMPLE 80

(Trans)-2-butyl-6-[hexahydro-2-(hydroxymethyl)-Pyrrolo[1,2-b]isoxazol-2-yl]-3-[[2'-[1H-tetrazol-5-yl)[1,1'-biphenyl]-4-yl]methyl-4(3H)quinazolinone A solution of 0.112 g of (Trans)-2-butyl-6-hexahydro-2-hydroxymethyl)-pyrrolo[1,2-b]isoxazol-2-yl]-3-[[2'-[1-triphenylmethyl)-1H-tetrazolyl-5-yl][1,1'-biphenyl]-4-yl]methyl-4(3H)-quinazolinone in 1.0 ml of tetrahydrofuran and 5.0 ml of methanol is heated at reflux for 8 hours. The reaction is cooled to room temperature and concentrated in vacuo. The residue is chromatographed on silica gel eluting with 98:2 chloroform-methanol to provide 0.058 g of the desired product as a white solid. FAB Mass Spec 578 (M+H).

EXAMPLE 81-118

The procedure of Example 73 is substantially followed with the following list of starting materials to obtain the desired salt product.

| Example | Starting Material of Example | Starting Base Material | Salt Product |
|---|---|---|---|
| 81 | 57 | Sodium Hydroxide | Sodium |
| 82 | 59 | Sodium Hydroxide | Sodium |
| 83 | 60 | Sodium Hydroxide | Sodium |
| 84 | 61 | Sodium Hydroxide | Sodium |
| 85 | 62 | Sodium Hydroxide | Sodium |
| 86 | 63 | Sodium Hydroxide | Sodium |
| 87 | 64 | Sodium Hydroxide | Sodium |
| 88 | 65 | Sodium Hydroxide | Sodium |
| 89 | 66 | Sodium Hydroxide | Sodium |
| 90 | 67 | Sodium Hydroxide | Sodium |
| 91 | 68 | Sodium Hydroxide | Sodium |
| 92 | 69 | Sodium Hydroxide | Sodium |
| 93 | 70 | Sodium Hydroxide | Sodium |
| 94 | 71 | Sodium Hydroxide | Sodium |
| 95 | 72 | Sodium Hydroxide | Sodium |
| 96 | 78 | Sodium Hydroxide | Sodium |
| 97 | 80 | Sodium Hydroxide | Sodium |
| 98 | 58 | Potassium Hydroxide | Potassium |
| 99 | 58 | Calcium Hydroxide | Calcium |
| 100 | 58 | Magnesium Hydroxide | Magnesium |
| 101 | 58 | Ammonium Hydroxide | Ammonium |
| 102 | 57 | Potassium Hydroxide | Potassium |
| 103 | 59 | Potassium Hydroxide | Potassium |
| 104 | 60 | Potassium Hydroxide | Potassium |
| 105 | 61 | Potassium Hydroxide | Potassium |
| 106 | 62 | Potassium Hydroxide | Potassium |
| 107 | 63 | Potassium Hydroxide | Potassium |
| 108 | 64 | Potassium Hydroxide | Potassium |
| 109 | 65 | Potassium Hydroxide | Potassium |
| 110 | 66 | Potassium Hydroxide | Potassium |
| 111 | 67 | Potassium Hydroxide | Potassium |
| 112 | 68 | Potassium Hydroxide | Potassium |
| 113 | 69 | Potassium Hydroxide | Potassium |
| 114 | 70 | Potassium Hydroxide | Potassium |
| 115 | 71 | Potassium Hydroxide | Potassium |
| 116 | 72 | Potassium Hydroxide | Potassium |
| 117 | 78 | Potassium Hydroxide | Potassium |
| 118 | 80 | Potassium Hydroxide | Potassium |

Angiotensin II Antagonists In Vitro Tests

Materials and Methods:

Beef adrenals are obtained from a local slaughter house (Maxwell-Cohen). [$^{125}$I](Sar$^1$, Ile$^8$)AngII, S. A. 2200 Ci/mmole, is purchased from Dupont (NEN®, Boston, Mass.). All unlabeled AngII analogs, Dimethylsulfoxide (DMSO), nucleotides, bovine serum albumin (BSA) are purchased from Sigma Chemical Co., St. Louis, Mo. U.S.A.

Preparation of Membranes: Approximately sixteen (16) to twenty (20) beef adrenal glands are processed as follows: fresh adrenal glands received on crushed ice are cleaned of fatty tissues and the tough membranes encapsulating the glands are removed and discarded. The brownish tissue forming the adrenal cortex is scraped off and finely minced with scissors before homogenization. Care is taken to avoid contamination with medullary tissue during dissection. The scraped cortices are suspended in twenty volumes of an ice-cold buffer medium consisting of 10 mM Tris.HCl (pH 7.4 at 22° C.) and containing 1.0 mM EDTA and 0.2M sucrose. Unless otherwise indicated, all subsequent operations are done at 4° C. The tissue is homogenized in a glass homogenizer with a motor-driven teflon pestle with a clearance of 1.0 mm. The homogenate is centrifuged first at low speed (3,000×g) for 10 min. The resulting pellet is discarded and the supernatant fluid recentrifuged at 10,000×g for 15 minutes to give a $P_2$ pellet. This $P_2$ pellet is discarded and the liquid phase is carefully decanted off in clean centrifuge tubes and recentrifuged at high speed (100,000×g) for 60 min. The translucent final pellet is harvested and combined in a small volume (20–50.0 ml) of 50.0 mM Tris.HCl buffer, pH 7.2. A 100 ul aliquot is withdrawn and the protein content of the preparation is determined by the Lowry's method (Lowry, O. H., Rosebrough, N. F., Farr, A. L. and Randall, R. J., Protein measurement with Folin phenol reagent. J. Biol. Chem., 48, 265–275, 1951). The pelleted membrane is reconstituted in 50.0 mM Tris.HCl buffer containing 0.1 mM of phenylmethylsulfonyl fluoride (PMSF) to give approximately a protein concentration of 2.5 mg per ml of tissue suspension. The membrane preparation is finally aliquoted in 1.0 ml volumes and stored at −70° C. until use in the binding assays.

Receptor Binding Assay:
Binding of[$^{125}$I](Sar$^1$,Ile$^8$)AngII

The binding of [$^{125}$I](Sar$^1$,Ile$^8$)AngII to microsomal membranes is initiated by the addition of reconstituted membranes (1:10 vols.) in freshly made 50.0 mM Tris.HCl buffer, pH 7.4 containing 0.25% heat inactivated bovine serum albumin (BSA): 80 ul membrane protein (10 to 20 ug/assay) to wells already containing 100 ul of incubation buffer (as described above) and 20 ul [$^{125}$I](Sar$^1$,Ile$^8$)AngII (Specific Activity, 2200 Ci/mmole). Non-specific binding is measured in the presence of 1.0 uM unlabeled (Sar$^1$,Ile$^8$)AngII, added in 20 ul volume. Specific binding for [$^{125}$I](Sar$^1$, Ile$^8$) AngII is greater than 90%. In competition studies, experimental compounds are diluted in dimethylsulfoxide (DMSO) and added in 20 ul to wells before the introduction of tissue membranes. This concentration of DMSO is found to have no negative effects on the binding of [$^{125}$I](Sar$^1$,Ile$^8$) AngII to the membranes. Assays are performed in triplicate. The wells are left undisturbed for 60 min. at room temperature. Following incubation, all wells are harvested at once with a Brandel ® Harvester especially designed for a 96 well plate (Brandel ® Biomedical Research & Development Labs. Inc., Gaithersburg, Md., U.S.A.). The filter discs are washed with 10×1.0 ml of cold 0.9% NaCl to remove unbound ligand. Presoaking the filter sheet in 0.1% polyethyleneimine in normal saline (PEI/Saline) greatly reduces the radioactivity retained by the filter blanks. This method is routinely used. The filters are removed from the filter grid and counted in a Parkard ® Cobra Gamma Counter for 1 min. (Packard Instrument Co., Downers Grove, Ill., U.S.A.). The binding data are analyzed by the non-linear interactive "LUNDON-1" program (LUNDON SOFTWARE Inc., Cleveland, Ohio U.S.A.). Compounds that displace 50% of the labelled angiotensin II at the screening dose of 50 µM are considered active compounds and are then evaluated in concentration-response experiments to determine their $IC_{50}$ values. The results are shown in Table I.

TABLE I

| Ex. No. | R$^6$ | X | Angiotensin II Receptor Binding $IC_{50}(M)$ |
|---|---|---|---|
| 57 | (pyrrolidine N-O with H) | −(CH$_2$)$_3$CH$_3$ | 32.2 × 10$^{-9}$ |
| 58 | (cyclohexane N—O with CH$_3$) | −(CH$_2$)$_3$CH$_3$ | 27 × 10$^{-9}$ |
| 59 | (cyclohexane N—O with CH$_3$) | −(CH$_2$)$_3$CH$_3$ | 55.0 × 10$^{-9}$ |
| 60 | (piperidine N—O) | −(CH$_2$)$_3$CH$_3$ | 38.0 × 10$^{-9}$ |
| 61 | (CH$_3$)$_2$C— N—O | −(CH$_2$)$_3$CH$_3$ | 39.0 × 10$^{-9}$ |
| 62 | (pyrrolidine N—O with CH$_3$-O-C(=O)-O) | −(CH$_2$)$_3$CH$_3$ | 69.0 × 10$^{-9}$ |
| 63 | (tetrahydroisoquinoline N—O) | −(CH$_2$)$_3$CH$_3$ | 54.0 × 10$^{-9}$ |

TABLE I-continued

| Ex. No. | Structure | $R^6$ | Biological Data |
|---|---|---|---|
| 64 | phenyl-fused cyclohexane with N—O, H, CH₃, CH₃ | $-(CH_2)_3CH_3$ | $94.0 \times 10^{-9}$ |
| 65 | cyclohexane with CH₃, N—O, H | $-(CH_2)_3CH_3$ | $65.0 \times 10^{-9}$ |
| 66 | cyclohexane with H, CH₃, CH₃, N—O, CH₃ | $-(CH_2)_3CH_3$ | $65.0 \times 10^{-9}$ |
| 67 | cyclohexane with H, CH₃, N—O | $-(CH_2)_3CH_3$ | $47.0 \times 10^{-9}$ |
| 68 | cyclohexane with H, CH₃, N—O | $-(CH_2)_3CH_3$ | $22.0 \times 10^{-9}$ |
| 69 | open chain with H, CH₃, CH₃, CH₃, N—O | $-(CH_2)_3CH_3$ | $70.0 \times 10^{-9}$ |
| 70 | phenyl, H, N—O | $-(CH_2)_3CH_3$ | $56.0 \times 10^{-9}$ |
| 71 | H, CH₃, N—O | $-(CH_2)_3CH_3$ | $63.0 \times 10^{-9}$ |
| 72 | H, CH₃, N—O | $-(CH_2)_3CH_3$ | $58.0 \times 10^{-9}$ |

BIOLOGICAL DATA

| Ex. No. | $R^6$ | X | Biological Data |
|---|---|---|---|
| 73* | N—O ring with H, CH₃ | $-(CH_2)_3CH_3$ | $3.1 \times 10^{-8}$ |
| 78 | $CH_3O_2C$, H, N—O | $-(CH_2)_3CH_3$ | $14.4 \times 10^{-8}$ |
| 80 | H, HO, N—O | $-(CH_2)_3CH_3$ | $3.5 \times 10^{-8}$ |

*Sodium Salt

As can be seen from the above table, the compounds demonstrate excellent activity.

The enzyme renin acts on a blood plasma $a_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

As can be seen from Table I, the compounds demonstrate excellent Angiotensin II Receptor Binding activity.

The enzyme renin acts on a blood plasma $a_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

The compounds of this invention inhibit the action of AII. By administering a compound of this invention to a rat, and then challenging with angiotensin II, a blockage of the vasopressor response is realized. The results of this test on representative compounds of this invention are shown in Table II.

AII Challenge

Conscious Male Okamoto-Aoki SHR, 16–20 weeks old, weighing approximately 330 g are purchased from Charles River Labs (Wilmington, Mass.). Conscious rats are restrained in a supine position with elastic tape. The area at the base of the tail is locally anesthetized by subcutaneous infiltration with 2% procaine. The ventral caudal artery and vein are isolated, and a cannula made of polyethylene (PE) 10–20 tubing (fused together by heat) is passed into the lower abdominal aorta and vena cava, respectively. The cannula is secured, heparinized (1,000 I.U./ml), sealed and the wound is closed. The animals are placed in plastic restraining cages in an upright position. The cannula is attached to a Statham $P_{23}Db$ pressure transducer, and pulsatile blood pressure is recorded to 10–15 minutes with a Gould Brush recorder. (Chan et al., (Drug Development Res., 18:75–94, 1989). Angiotensin II (human sequence, Sigma Chem. Co., St. Louis, Mo.) of 0.05 and 0.1 ug/kg i.v. is injected into all rats (predosing response). Then a test compound, vehicle or a known angiotensin II antagonist is administered i.v., i.p. or orally to each set of rats. The two doses of angiotensin II are given to each rat again at 30, 60, 90, 120, 180, 240 and 300 minutes post dosing the compound or vehicle. The vasopressor response of angiotensin II is measured for the increase in systolic blood pressure in mmHg. The percentage of antagonism or blockade of the vasopressor response of angiotensin II by a compound is calculated using the vasopressor response (increase in systolic blood pressure) of angiotensin II of each rat predosing the compound as 100%. A compound is considered active if at 30 mg/kg i.v. it antagonized at least 50% of the response.

| Example No. | Dose (mg/kg) | ANGIOTENSIN II (AII) VASOPRESSOR RESPONSE ||||||  |
|---|---|---|---|---|---|---|---|---|
| | | AII Dose mcg/kg IV | Min Post Dose | Control Before AII | Response After AII | Change | Average Change | % Inhibition |
| CONTROL | | 0.05 | 0 | 195 | 235 | 40 | 42.5 | |
| | | | | 200 | 245 | 45 | | |
| | | 0.1 | | 190 | 240 | 50 | 42.5 | |
| | | | | 205 | 240 | 35 | | |
| Ex. No. 57 | 5 P.O. | 0.05 | 30 | 195 | 235 | 40 | 31.5 | 26 |
| | | | | 195 | 218 | 23 | | |
| | | 0.1 | | 200 | 225 | 25 | 22.5 | 47 |
| | | | | 190 | 210 | 20 | | |
| | | 0.05 | 60 | 190 | 230 | 40 | 25 | 41 |
| | | | | 190 | 200 | 10 | | |
| | | 0.1 | | 185 | 220 | 35 | 29 | 32 |
| | | | | 170 | 193 | 23 | | |
| | | 0.05 | 90 | 185 | 205 | 20 | 32.5 | 24 |
| | | | | 175 | 220 | 45 | | |
| | | 0.1 | | 185 | 207 | 22 | 29.5 | 31 |
| | | | | 185 | 222 | 37 | | |
| | | 0.05 | 120 | 185 | 215 | 30 | 20 | 53 |
| | | | | 185 | 195 | 10 | | |
| | | 0.1 | | 185 | 210 | 25 | 25 | 41 |
| | | | | 175 | 200 | 25 | | |
| | | 0.05 | 180 | 185 | 210 | 25 | 20 | 53 |
| | | | | 195 | 210 | 15 | | |
| | | 0.1 | | 190 | 230 | 40 | 41.5 | 2 |
| | | | | 175 | 218 | 43 | | |
| SPONTANEOUSLY HYPERTENSIVE RATS n = 2 Body weight(s): 350, 350 grams ||||||||| |
| | | 0.05 | 240 | 185 | 210 | 25 | 20 | 53 |
| | | | | 185 | 200 | 15 | | |
| | | 0.1 | | 185 | 210 | 25 | 40 | 6 |
| | | | | 175 | 230 | 55 | | |
| | | 0.05 | 300 | 195 | 220 | 25 | 22.5 | 47 |
| | | | | 180 | 200 | 20 | | |
| | | 0.1 | | 180 | 230 | 50 | 42.5 | 0 |
| | | | | 175 | 210 | 35 | | |
| | | 0.05 | 0 | 160 | 200 | 40 | 37.5 | |
| | | | | 175 | 210 | 35 | | |
| | | 0.1 | | 160 | 200 | 40 | 40 | 40 |
| | | | | 180 | 220 | 40 | | |
| Ex. No. 57 | 3 I.V. | 0.05 | 30 | 165 | 165 | 0 | 12.5 | 67 |
| | | | | 200 | 225 | 25 | | |
| | | 0.1 | | 160 | 165 | 5 | 7.5 | 81 |
| | | | | 190 | 200 | 10 | | |
| | | 0.05 | 60 | 150 | 175 | 25 | 22.5 | 40 |
| | | | | 190 | 210 | 20 | | |
| | | 0.1 | | 155 | 160 | 5 | 15 | 63 |
| | | | | 185 | 210 | 25 | | |
| | | 0.05 | 90 | 150 | 175 | 25 | 20 | 47 |
| | | | | 180 | 195 | 15 | | |
| | | 0.1 | | 155 | 175 | 20 | 20 | 50 |
| | | | | 190 | 210 | 20 | | |
| SPONTANEOUSLY HYPERTENSIVE RATS n = 2 Body weight(s): 390, 360 grams ||||||||| |
| | | 0.05 | 120 | 175 | 190 | 15 | 17.5 | 57 |
| | | | | 200 | 220 | 20 | | |
| | | 0.1 | | 165 | 195 | 30 | 37.5 | 17 |
| | | | | 185 | 230 | 45 | | |
| | | 0.05 | 180 | 165 | 207 | 42 | 36 | 11 |
| | | | | 190 | 220 | 30 | | |
| | | 0.1 | | 175 | 218 | 43 | 44 | 2 |
| | | | | 185 | 230 | 45 | | |
| CONTROL | | 0.05 | 0 | 240 | 275 | 35 | 38.5 | |
| | | | | 215 | 257 | 42 | | |
| | | 0.1 | | 225 | 270 | 45 | 45 | |
| | | | | 215 | 260 | 45 | | |
| Ex. No. 58 | 3 I.V. | 0.05 | 30 | 210 | 210 | 0 | 0 | 100 |
| | | | | 185 | 185 | 0 | | |
| | | 0.,1 | | 200 | 210 | 10 | 10 | 78 |
| | | | | 175 | 185 | 10 | | |
| | | 0.05 | 60 | 210 | 220 | 10 | 5 | 87 |
| | | | | 185 | 185 | 0 | | |
| | | 0.1 | | 207 | 215 | 8 | 4 | 91 |
| | | | | 190 | 190 | 0 | | |
| | | 0.05 | 90 | 210 | 215 | 5 | 2.5 | 94 |
| | | | | 185 | 185 | 0 | | |
| | | 0.1 | | 200 | 200 | 0 | 2.5 | 94 |
| | | | | 185 | 190 | 5 | | |

-continued

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| SPONTANEOUSLY HYPERTENSIVE RATS n = 2 Body weight(s): 330, 310 grams | | | | | | | | |
| | | 0.05 | 120 | 195 | 200 | 5 | 5 | 87 |
| | | | | 190 | 195 | 5 | | |
| | | 0.1 | | 195 | 200 | 5 | 10 | 78 |
| | | | | 185 | 200 | 15 | | |
| | | 0.05 | 180 | 185 | 195 | 10 | 6.5 | 83 |
| | | | | 190 | 193 | 3 | | |
| | | 0.1 | | 190 | 198 | 8 | 6.5 | 86 |
| | | | | 195 | 200 | 5 | | |
| | | 0.05 | 240 | 190 | 200 | 10 | 7.5 | 81 |
| | | | | 190 | 195 | 5 | | |
| | | 0.1 | | 193 | 200 | 7 | 4 | 91 |
| | | | | 185 | 186 | 1 | | |
| CONTROL | | 0.05 | 0 | 175 | 210 | 35 | 40.5 | |
| | | | | 205 | 251 | 46 | | |
| | | 0.1 | | 180 | 225 | 45 | 47.5 | |
| | | | | 205 | 255 | 50 | | |
| Ex. No. 58 | 5 P.O. | 0.05 | 30 | 175 | 175 | 0 | 4 | 90 |
| | | | | 200 | 208 | 8 | | |
| | | 0.1 | | 170 | 175 | 5 | 2.5 | 95 |
| | | | | 200 | 200 | 0 | | |
| | | 0.05 | 60 | 175 | 175 | 0 | 2.5 | 94 |
| | | | | 210 | 215 | 5 | | |
| | | 0.1 | | 175 | 175 | 0 | 0 | 100 |
| | | | | 210 | 210 | 0 | | |
| SPONTANEOUSLY HYPERTENSIVE RATS n = 2 Body weight(s): 340, 340 grams | | | | | | | | |
| | | 0.05 | 90 | 175 | 180 | 5 | 5 | 88 |
| | | | | 230 | 235 | 5 | | |
| | | 0.1 | | 170 | 170 | 0 | 7.5 | 84 |
| | | | | 220 | 235 | 15 | | |
| | | 0.05 | 120 | 175 | 185 | 10 | 5 | 88 |
| | | | | 210 | 210 | 0 | | |
| | | 0.1 | | 185 | 185 | 0 | 2.5 | 95 |
| | | | | 210 | 215 | 5 | | |
| | | 0.05 | 180 | 180 | 195 | 15 | 10 | 75 |
| | | | | 220 | 225 | 5 | | |
| | | 0.1 | | 180 | 185 | 5 | 5 | 89 |
| | | | | 210 | 215 | 5 | | |
| | | 0.05 | 240 | 170 | 175 | 5 | 3 | 93 |
| | | | | 206 | 207 | 1 | | |
| | | 0.1 | | 175 | 180 | 5 | 2.5 | 95 |
| | | | | 225 | 225 | 0 | | |
| | | 0.05 | 300 | 170 | 172 | 2 | 1 | 98 |
| | | | | 220 | 220 | 0 | | |
| | | 0.1 | | 175 | 185 | 10 | 7.5 | 84 |
| | | | | 203 | 208 | 5 | | |
| CONTROL | | 0.05 | 0 | 195 | 235 | 40 | 40 | |
| | | | | 195 | 235 | 40 | | |
| | | 0.1 | | 205 | 245 | 40 | 45 | |
| | | | | 200 | 250 | 50 | | |
| SPONTANEOUSLY HYPERTENSIVE RATS n = 2 Body weight(s): 340, 340 grams | | | | | | | | |
| Ex. No. 58 | 5 P.O. | 0.05 | 30 | 188 | 195 | 7 | 6 | 85 |
| | | | | 190 | 195 | 5 | | |
| | | 0.1 | | 188 | 195 | 7 | 6 | 87 |
| | | | | 185 | 190 | 5 | | |
| | | 0.05 | 60 | 175 | 180 | 5 | 2.5 | 94 |
| | | | | 190 | 190 | 0 | | |
| | | 0.1 | | 185 | 185 | 0 | 0 | 100 |
| | | | | 185 | 185 | 0 | | |
| | | 0.05 | 90 | 185 | 190 | 5 | 5.5 | 86 |
| | | | | 184 | 190 | 6 | | |
| | | 0.1 | | 190 | 196 | 6 | 3 | 93 |
| | | | | 185 | 185 | 0 | | |
| | | 0.05 | 120 | 180 | 190 | 10 | 5 | 88 |
| | | | | 195 | 195 | 0 | | |
| | | 0.1 | | 185 | 195 | 10 | 7.5 | 83 |
| | | | | 190 | 195 | 5 | | |
| | | 0.05 | 180 | 180 | 185 | 5 | 3.5 | 91 |
| | | | | 183 | 185 | 2 | | |
| | | 0.1 | | 175 | 180 | 5 | 4 | 91 |
| | | | | 185 | 188 | 3 | | |
| | | 0.05 | 240 | 185 | 190 | 5 | 2.5 | 94 |
| | | | | 185 | 185 | 0 | | |
| | | 0.1 | | 190 | 200 | 10 | 5 | 89 |
| | | | | 225 | 225 | 0 | | |
| SPONTANEOUSLY HYPERTENSIVE RATS n = 2 Body weight(s): 325, 315 grams | | | | | | | | |
| | | 0.05 | 300 | 193 | 195 | 2 | 1 | 98 |

-continued

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| | | | | 185 | 185 | 0 | | |
| | | 0.1 | | 185 | 195 | 10 | 9.5 | 79 |
| | | | | 177 | 186 | 9 | | |
| CONTROL | | 0.05 | 0 | 220 | 255 | 35 | 30 | |
| | | | | 165 | 190 | 25 | | |
| | | 0.1 | | 200 | 248 | 48 | 39 | 100 |
| | | | | 170 | 200 | 30 | | |
| Ex. No. 58 | 3 P.O. | 0.05 | 30 | 210 | 225 | 15 | 7.5 | 75 |
| | | | | 150 | 150 | 0 | | |
| | | 0.1 | | 200 | 220 | 20 | 10 | 74 |
| | | | | 150 | 150 | 0 | | |
| | | 0.05 | 60 | 200 | 205 | 5 | 2.5 | 92 |
| | | | | 165 | 165 | 0 | | |
| | | 0.1 | | 195 | 211 | 16 | 13 | 67 |
| | | | | 165 | 175 | 10 | | |
| | | 0.05 | 90 | 200 | 210 | 10 | 7.5 | 75 |
| | | | | 155 | 160 | 5 | | |
| | | 0.1 | | 190 | 210 | 20 | 15 | 62 |
| | | | | 155 | 165 | 10 | | |
| | | 0.05 | 120 | 190 | 205 | 15 | 10 | 67 |
| | | | | 180 | 185 | 5 | | |
| | | 0.1 | | 183 | 185 | 2 | 3.5 | 91 |
| | | | | 170 | 175 | 5 | | |
| SPONTANEOUSLY HYPERTENSIVE RATS n = 2 Body weight(s): 310, 380 grams | | | | | | | | |
| | | 0.05 | 180 | 185 | 190 | 5 | 7.5 | 75 |
| | | | | 155 | 165 | 10 | | |
| | | 0.1 | | 185 | 195 | 10 | 10 | 74 |
| | | | | 155 | 165 | 10 | | |
| | | 0.05 | 240 | 190 | 220 | 30 | 17.5 | 42 |
| | | | | 150 | 155 | 5 | | |
| | | 0.1 | | 190 | 220 | 30 | 17.5 | 55 |
| | | | | 175 | 180 | 5 | | |
| | | 0.05 | 300 | 209 | 235 | 26 | 13 | 57 |
| | | | | 150 | 150 | 0 | | |
| | | 0.1 | | 210 | 240 | 30 | 17.5 | 55 |
| | | | | 155 | 160 | 5 | | |
| CONTROL | | 0.05 | 0 | 185 | 215 | 30 | 30 | |
| | | | | 220 | 250 | 30 | | |
| | | 0.1 | | 180 | 226 | 46 | 48 | |
| | | | | 210 | 260 | 50 | | |
| Ex. No. 58 | 3 P.O. | 0.05 | 30 | 175 | 180 | 5 | 5 | 83 |
| | | | | 210 | 215 | 5 | | |
| | | 0.1 | | 170 | 177 | 7 | 28.5 | 41 |
| | | | | 180 | 230 | 50 | | |
| | | 0.05 | 60 | 185 | 185 | 0 | 0 | 100 |
| | | | | 200 | 200 | 0 | | |
| | | 0.1 | | 185 | 200 | 15 | 10 | 79 |
| | | | | 200 | 205 | 5 | | |
| SPONTANEOUSLY HYPERTENSIVE RATS n = 2 Body weight(s): 340, 340 grams | | | | | | | | |
| | | 0.05 | 90 | 190 | 193 | 3 | 6 | 80 |
| | | | | 196 | 205 | 9 | | |
| | | 0.1 | | 195 | 200 | 5 | 2.5 | 95 |
| | | | | 205 | 205 | 0 | | |
| | | 0.05 | 120 | 188 | 200 | 12 | 6 | 80 |
| | | | | 190 | 190 | 0 | | |
| | | 0.1 | | 185 | 188 | 3 | 1.5 | 97 |
| | | | | 190 | 190 | 0 | | |
| | | 0.05 | 180 | 193 | 193 | 0 | 3.5 | 88 |
| | | | | 198 | 205 | 7 | | |
| | | 0.1 | | 190 | 200 | 10 | 8 | 83 |
| | | | | 200 | 206 | 6 | | |
| | | 0.05 | 240 | 170 | 175 | 5 | 5 | 83 |
| | | | | 185 | 190 | 5 | | |
| | | 0.1 | | 165 | 180 | 15 | 11 | 77 |
| | | | | 183 | 190 | 7 | | |
| | | 0.05 | 300 | 190 | 200 | 10 | 7.5 | 75 |
| | | | | 190 | 195 | 5 | | |
| | | 0.1 | | 190 | 195 | 5 | 5 | 90 |
| | | | | 185 | 190 | 5 | | |
| CONTROL | | 0.05 | 0 | 190 | 240 | 50 | 42.5 | |
| | | | | 195 | 230 | 35 | | |
| | | 0.1 | | 185 | 240 | 55 | 47.5 | 79 |
| | | | | 195 | 235 | 40 | | |
| SPONTANEOUSLY HYPERTENSIVE RATS n = 2 Body weight(s): 340, 340 grams | | | | | | | | |
| Ex. No. 58 | 1 P.O. | 0.05 | 30 | 185 | 210 | 25 | 16 | 62 |
| | | | | 170 | 177 | 7 | | |
| | | 0.1 | | 188 | 220 | 32 | 26 | 45 |

-continued

| | | ANGIOTENSIN II (AII) VASOPRESSOR RESPONSE | | | | | |
|---|---|---|---|---|---|---|---|
| Example No. | Dose (mg/kg) | AII Dose mcg/kg IV | Min Post Dose | Control Before AII | Response After AII | Change | Average Change | % Inhibition |
| | | | | 170 | 190 | 20 | | |
| | | 0.05 | 60 | 185 | 207 | 22 | 16 | 62 |
| | | | | 185 | 195 | 10 | | |
| | | 0.1 | | 175 | 215 | 40 | 30 | 37 |
| | | | | 170 | 190 | 20 | | |
| | | 0.05 | 90 | 170 | 192 | 22 | 13.5 | 68 |
| | | | | 185 | 190 | 5 | | |
| | | 0.1 | | 175 | 210 | 35 | 26.5 | 44 |
| | | | | 177 | 195 | 18 | | |
| | | 0.05 | 120 | 190 | 213 | 23 | 14 | 67 |
| | | | | 195 | 200 | 5 | | |
| | | 0.1 | | 200 | 225 | 25 | 22.5 | 53 |
| | | | | 190 | 210 | 20 | | |
| | | 0.05 | 180 | 190 | 200 | 10 | 7.5 | 82 |
| | | | | 200 | 205 | 5 | | |
| | | 0.1 | | 188 | 215 | 27 | 21 | 56 |
| | | | | 210 | 225 | 15 | | |
| | | 0.05 | 240 | 175 | 185 | 10 | 7.5 | 82 |
| | | | | 175 | 180 | 5 | | |
| | | 0.1 | | 175 | 200 | 25 | 15 | 68 |
| | | | | 175 | 180 | 5 | | |
| SPONTANEOUSLY HYPERTENSIVE RATS n = 2 Body weight(s): 320, 305 grams | | | | | | | | |
| Ex. No. 58 | 1 P.O. | 0.05 | 30 | 185 | 210 | 25 | 16 | 62 |
| | | | | 170 | 177 | 7 | | |
| | | 0.1 | | 188 | 220 | 32 | 26 | 45 |
| | | | | 170 | 190 | 20 | | |
| | | 0.05 | 60 | 185 | 207 | 22 | 16 | 62 |
| | | | | 185 | 195 | 10 | | |
| | | 0.1 | | 175 | 215 | 40 | 30 | 37 |
| | | | | 170 | 190 | 20 | | |
| | | 0.05 | 90 | 170 | 192 | 22 | 13.5 | 68 |
| | | | | 185 | 190 | 5 | | |
| | | 0.1 | | 175 | 210 | 35 | 26.5 | 44 |
| | | | | 177 | 195 | 18 | | |
| | | 0.05 | 120 | 190 | 213 | 23 | 14 | 67 |
| | | | | 195 | 200 | 5 | | |
| | | 0.1 | | 200 | 225 | 25 | 22.5 | 53 |
| | | | | 190 | 210 | 20 | | |
| | | 0.05 | 180 | 190 | 200 | 10 | 7.5 | 82 |
| | | | | 200 | 205 | 5 | | |
| | | 0.1 | | 188 | 215 | 27 | 21 | 56 |
| | | | | 210 | 225 | 15 | | |
| | | 0.05 | 240 | 175 | 185 | 10 | 7.5 | 82 |
| | | | | 175 | 180 | 5 | | |
| | | 0.1 | | 175 | 200 | 25 | 15 | 68 |
| | | | | 175 | 180 | 5 | | |
| SPONTANEOUSLY HYPERTENSIVE RATS n = 2 Body weight(s): 320, 305 grams | | | | | | | | |
| | | 0.05 | 30 | 173 | 190 | 17 | 11 | 74 |
| | | | | 190 | 195 | 5 | | |
| | | 0.1 | | 180 | 210 | 30 | 18.5 | 61 |
| | | | | 188 | 195 | 7 | | |
| CONTROL | | 0.05 | 0 | 180 | 233 | 53 | 34 | |
| | | | | 225 | 240 | 15 | | |
| | | 0.1 | | 185 | 235 | 50 | 41 | |
| | | | | 210 | 242 | 32 | | |
| Ex. No. 59 | 3 I.V. | 0.05 | 30 | 190 | 210 | 20 | 17.5 | 49 |
| | | | | 200 | 215 | 15 | | |
| | | 0.1 | | 180 | 207 | 27 | 21 | 49 |
| | | | | 200 | 215 | 15 | | |
| | | 0.05 | 60 | 195 | 198 | 3 | 9 | 74 |
| | | | | 200 | 215 | 15 | | |
| | | 0.1 | | 188 | 215 | 27 | 23.5 | 43 |
| | | | | 200 | 220 | 20 | | |
| | | 0.05 | 90 | 190 | 215 | 25 | 18.5 | 46 |
| | | | | 208 | 220 | 12 | | |
| | | 0.1 | | 185 | 210 | 25 | 17.5 | 57 |
| | | | | 200 | 210 | 10 | | |
| | | 0.05 | 120 | 190 | 202 | 12 | 9.5 | 72 |
| | | | | 208 | 215 | 7 | | |
| | | 0.1 | | 185 | 200 | 15 | 12.5 | 70 |
| | | | | 200 | 210 | 10 | | |
| SPONTANEOUSLY HYPERTENSIVE RATS n = 2 Body weight(s): 340, 315 grams | | | | | | | | |
| | | 0.05 | 180 | 175 | 200 | 25 | 20 | 41 |
| | | | | 190 | 205 | 15 | | |
| | | 0.1 | | 185 | 210 | 25 | 22.5 | 45 |
| | | | | 200 | 220 | 20 | | |
| | | 0.05 | 240 | 170 | 190 | 20 | 18.5 | 46 |

-continued

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| | | | | 190 | 207 | 17 | | |
| | | 0.1 | | 175 | 205 | 30 | 27.5 | 33 |
| | | | | 190 | 215 | 25 | | |
| | | 0.05 | 0 | 225 | 267 | 42 | 37.5 | |
| | | | | 220 | 253 | 33 | | |
| | | 0.1 | | 225 | 270 | 45 | 44 | |
| | | | | 210 | 253 | 43 | | |
| Ex. No. 59 | 5 P.O. | 0.05 | 30 | 210 | 225 | 15 | 19 | 49 |
| | | | | 200 | 223 | 23 | | |
| | | 0.1 | | 210 | 235 | 25 | 22.5 | 49 |
| | | | | 190 | 210 | 20 | | |
| | | 0.05 | 60 | 250 | 270 | 20 | 12.5 | 67 |
| | | | | 210 | 215 | 5 | | |
| | | 0.1 | | 220 | 235 | 15 | 12.5 | 72 |
| | | | | 200 | 210 | 10 | | |
| | | 0.05 | 90 | 215 | 235 | 20 | 17.5 | 53 |
| | | | | 215 | 230 | 15 | | |
| | | 0.1 | | 210 | 235 | 25 | 17.5 | 60 |
| | | | | 200 | 210 | 10 | | |
| SPONTANEOUSLY HYPERTENSIVE RATS n = 2 Body weight(s): 330, 320 grams | | | | | | | | |
| | | 0.05 | 120 | 207 | 235 | 28 | 24 | 36 |
| | | | | 195 | 215 | 20 | | |
| | | 0.1 | | 210 | 235 | 25 | 17.5 | 60 |
| | | | | 200 | 210 | 10 | | |
| | | 0.05 | 180 | 173 | 195 | 22 | 18.5 | 51 |
| | | | | 195 | 210 | 15 | | |
| | | 0.1 | | 190 | 200 | 10 | 14 | 68 |
| | | | | 200 | 218 | 18 | | |
| | | 0.05 | 240 | 165 | 185 | 20 | 12.5 | 67 |
| | | | | 205 | 210 | 5 | | |
| | | 0.1 | | 185 | 195 | 10 | 10 | 77 |
| | | | | 210 | 220 | 10 | | |
| | | 0.05 | 300 | 170 | 185 | 15 | 12.5 | 67 |
| | | | | 200 | 210 | 10 | | |
| | | 0.1 | | 170 | 185 | 15 | 10 | 77 |
| | | | | 195 | 200 | 5 | | |
| CONTROL | | 0.05 | 0 | 205 | 250 | 45 | 41 | |
| | | | | 195 | 232 | 37 | | |
| | | 0.1 | | 200 | 250 | 50 | 49 | |
| | | | | 192 | 240 | 48 | | |
| Ex. No. 60 | 10 I.V. | 0.05 | 30 | 185 | 185 | 0 | 0 | 100 |
| | | | | 180 | 180 | 0 | | |
| | | 0.1 | | 175 | 175 | 0 | 0 | 100 |
| | | | | 182 | 182 | 0 | | |
| SPONTANEOUSLY HYPERTENSIVE RATS n = 2 Body weight(s): 325, 305 grams | | | | | | | | |
| | | 0.05 | 60 | 190 | 200 | 10 | 7.5 | 82 |
| | | | | 175 | 180 | 5 | | |
| | | 0.1 | | 200 | 205 | 5 | 7.5 | 85 |
| | | | | 170 | 180 | 10 | | |
| | | 0.05 | 90 | 170 | 178 | 8 | 14 | 66 |
| | | | | 165 | 185 | 20 | | |
| | | 0.1 | | 175 | 185 | 10 | 15 | 69 |
| | | | | 165 | 185 | 20 | | |
| | | 0.05 | 120 | 175 | 190 | 15 | 9.5 | 77 |
| | | | | 166 | 170 | 4 | | |
| | | 0.1 | | 180 | 195 | 15 | 12.5 | 74 |
| | | | | 185 | 195 | 10 | | |
| | | 0.05 | 180 | 180 | 190 | 10 | 12.5 | 70 |
| | | | | 180 | 195 | 15 | | |
| | | 0.1 | | 177 | 195 | 18 | 21.5 | 56 |
| | | | | 175 | 200 | 25 | | |
| | | 0.05 | 240 | 170 | 185 | 15 | 17 | 59 |
| | | | | 171 | 190 | 19 | | |
| | | 0.1 | | 175 | 185 | 10 | 12.5 | 74 |
| | | | | 175 | 190 | 15 | | |
| | | 0.05 | 300 | 164 | 170 | 6 | 12.5 | 70 |
| | | | | 177 | 196 | 19 | | |
| | | 0.1 | | 170 | 190 | 20 | 22.5 | 54 |
| | | | | 175 | 200 | 25 | | |
| SPONTANEOUSLY HYPERTENSIVE RATS n = 2 Body weight(s): 325, 305 grams | | | | | | | | |
| CONTROL | | 0.05 | 0 | 170 | 200 | 30 | 37.5 | |
| | | | | 185 | 230 | 45 | | |
| | | 0.1 | | 160 | 200 | 40 | 40 | |
| | | | | 180 | 220 | 40 | | |
| Ex. No. 60 | 3 I.V. | 0.05 | 30 | 135 | 140 | 5 | 7.5 | 80 |
| | | | | 155 | 165 | 10 | | |
| | | 0.1 | | 135 | 145 | 10 | 12.5 | 69 |

-continued

ANGIOTENSIN II (AII) VASOPRESSOR RESPONSE

| Example No. | Dose (mg/kg) | AII Dose mcg/kg IV | Min Post Dose | Control Before AII | Response After AII | Change | Average Change | % Inhibition |
|---|---|---|---|---|---|---|---|---|
| | | | | 150 | 165 | 15 | | |
| | | 0.05 | 60 | 135 | 145 | 10 | 10 | 73 |
| | | | | 155 | 165 | 10 | | |
| | | 0.1 | | 140 | 142 | 2 | 8.5 | 79 |
| | | | | 145 | 160 | 15 | | |
| | | 0.05 | 90 | 150 | 165 | 15 | 10 | 73 |
| | | | | 145 | 150 | 5 | | |
| | | 0.1 | | 152 | 160 | 8 | 12.5 | 69 |
| | | | | 135 | 152 | 17 | | |
| | | 0.05 | 120 | 155 | 165 | 10 | 10 | 73 |
| | | | | 145 | 155 | 10 | | |
| | | 0.1 | | 150 | 165 | 15 | 17.5 | 56 |
| | | | | 145 | 165 | 20 | | |
| | | 0.05 | 180 | 150 | 185 | 35 | 30 | 20 |
| | | | | 150 | 175 | 25 | | |
| | | 0.1 | | 170 | 185 | 15 | 22.5 | 44 |
| | | | | 150 | 180 | 30 | | |
| SPONTANEOUSLY HYPERTENSIVE RATS n = 2 Body weight(s): 330, 320 grams | | | | | | | | |
| CONTROL | | 0.05 | 0 | 195 | 235 | 40 | 36.5 | |
| | | | | 200 | 233 | 33 | | |
| | | 0.1 | | 200 | 236 | 36 | 36.5 | |
| | | | | 200 | 237 | 37 | | |
| Ex. No. 60 | 3 I.V. | 0.05 | 30 | 195 | 200 | 5 | 2.5 | 93 |
| | | | | 190 | 190 | 0 | | |
| | | 0.1 | | 185 | 195 | 10 | 5 | 86 |
| | | | | 185 | 185 | 0 | | |
| | | 0.05 | 60 | 190 | 195 | 5 | 5 | 86 |
| | | | | 180 | 185 | 5 | | |
| | | 0.1 | | 190 | 200 | 10 | 6.5 | 82 |
| | | | | 182 | 185 | 3 | | |
| | | 0.05 | 90 | 195 | 200 | 5 | 2.5 | 93 |
| | | | | 183 | 183 | 0 | | |
| | | 0.1 | | 200 | 205 | 5 | 2.5 | 93 |
| | | | | 185 | 185 | 0 | | |
| | | 0.05 | 120 | 170 | 185 | 15 | 15 | 59 |
| | | | | 185 | 200 | 15 | | |
| | | 0.1 | | 170 | 185 | 15 | 12.5 | 66 |
| | | | | 185 | 195 | 10 | | |
| | | 0.05 | 180 | 180 | 190 | 10 | 14 | 62 |
| | | | | 185 | 203 | 18 | | |
| | | 0.1 | | 180 | 207 | 27 | 23.5 | 36 |
| | | | | 190 | 210 | 20 | | |
| SPONTANEOUSLY HYPERTENSIVE RATS n = 2 Body weight(s): 320, 280 grams | | | | | | | | |
| | | 0.05 | 240 | 170 | 185 | 15 | 15 | 59 |
| | | | | 200 | 215 | 15 | | |
| | | 0.1 | | 175 | 200 | 25 | 18.5 | 49 |
| | | | | 198 | 210 | 12 | | |
| | | 0.05 | 300 | 180 | 190 | 10 | 15 | 59 |
| | | | | 190 | 210 | 20 | | |
| | | 0.1 | | 185 | 210 | 25 | 30 | 18 |
| | | | | 190 | 225 | 35 | | |
| CONTROL | | 0.05 | 0 | 140 | 190 | 50 | 45 | |
| | | | | 200 | 240 | 40 | | |
| | | 0.1 | | 140 | 195 | 55 | 46 | |
| | | | | 205 | 242 | 37 | | |
| Ex. No. 61 | 3 I.V. | 0.05 | 30 | 140 | 145 | 5 | 7.5 | 83 |
| | | | | 200 | 210 | 10 | | |
| | | 0.1 | | 135 | 145 | 10 | 7.5 | 84 |
| | | | | 195 | 200 | 5 | | |
| | | 0.05 | 60 | 145 | 160 | 15 | 10 | 78 |
| | | | | 195 | 200 | 5 | | |
| | | 0.1 | | 145 | 170 | 25 | 12.5 | 73 |
| | | | | 200 | 200 | 0 | | |
| | | 0.05 | 90 | 160 | 172 | 12 | 6 | 87 |
| | | | | 195 | 195 | 0 | | |
| | | 0.1 | | 165 | 172 | 7 | 3.5 | 92 |
| | | | | 200 | 200 | 0 | | |
| SPONTANEOUSLY HYPERTENSIVE RATS n = 2 Body weight(s): 325, 270 grams | | | | | | | | |
| | | 0.05 | 120 | 155 | 180 | 25 | 13.5 | 70 |
| | | | | 190 | 192 | 2 | | |
| | | 0.1 | | 160 | 185 | 25 | 15 | 67 |
| | | | | 190 | 195 | 5 | | |
| | | 0.05 | 180 | 150 | 175 | 25 | 15 | 67 |
| | | | | 185 | 190 | 5 | | |
| | | 0.1 | | 150 | 175 | 25 | 16 | 65 |
| | | | | 183 | 190 | 7 | | |
| CONTROL | | 0.05 | 0 | 180 | 235 | 55 | 46 | |

-continued

| | | ANGIOTENSIN II (AII) VASOPRESSOR RESPONSE | | | | | |
|---|---|---|---|---|---|---|---|
| Example No. | Dose (mg/kg) | AII Dose mcg/kg IV | Min Post Dose | Control Before AII | Response After AII | Change | Average Change | % Inhibition |
| | | | | 193 | 230 | 37 | | |
| | | 0.1 | | 180 | 230 | 50 | 47 | |
| | | | | 193 | 237 | 44 | | |
| Ex. No. 61 | 5 P.O. | 0.05 | 30 | 185 | 215 | 30 | 27.5 | 40 |
| | | | | 190 | 215 | 25 | | |
| | | 0.1 | | 175 | 210 | 35 | 32.5 | 31 |
| | | | | 195 | 225 | 30 | | |
| | | 0.05 | 60 | 180 | 195 | 15 | 29 | 37 |
| | | | | 190 | 233 | 43 | | |
| | | 0.1 | | 175 | 215 | 40 | 35 | 26 |
| | | | | 195 | 225 | 30 | | |
| | | 0.05 | 90 | 190 | 210 | 20 | 30 | 35 |
| | | | | 190 | 230 | 40 | | |
| | | 0.1 | | 185 | 203 | 18 | 29 | 38 |
| | | | | 180 | 220 | 40 | | |
| SPONTANEOUSLY HYPERTENSIVE RATS n = 2 Body weight(s): 350, 315 grams | | | | | | | | |
| | | 0.05 | 120 | 175 | 195 | 20 | 22.5 | 51 |
| | | | | 190 | 215 | 25 | | |
| | | 0.1 | | 175 | 205 | 30 | 30 | 36 |
| | | | | 185 | 215 | 30 | | |
| | | 0.05 | 180 | 165 | 190 | 25 | 35 | 24 |
| | | | | 185 | 230 | 45 | | |
| | | 0.1 | | 170 | 205 | 35 | 35 | 26 |
| | | | | 190 | 225 | 35 | | |
| CONTROL | | 0.05 | 0 | 225 | 270 | 45 | 40 | |
| | | | | 230 | 265 | 35 | | |
| | | 0.1 | | 225 | 273 | 48 | 41.5 | |
| | | | | 225 | 260 | 35 | | |
| Ex. No. 62 | 5 P.O. | 0.05 | 30 | 225 | 250 | 25 | 22.5 | 44 |
| | | | | 225 | 245 | 20 | | |
| | | 0.1 | | 210 | 257 | 47 | 43.5 | −5 |
| | | | | 215 | 255 | 40 | | |
| | | 0.05 | 60 | 235 | 275 | 40 | 37.5 | 6 |
| | | | | 225 | 260 | 35 | | |
| | | 0.1 | | 220 | 270 | 50 | 43.5 | −5 |
| | | | | 220 | 257 | 37 | | |
| | | 0.05 | 90 | 210 | 255 | 45 | 323.5 | 19 |
| | | | | 235 | 255 | 20 | | |
| | | 0.1 | | 207 | 257 | 50 | 45 | −8 |
| | | | | 220 | 260 | 40 | | |
| SPONTANEOUSLY HYPERTENSIVE RATS n = 2 Body weight(s): 315, 340 grams | | | | | | | | |
| | | 0.05 | 120 | 225 | 265 | 40 | 40 | 0 |
| | | | | 215 | 255 | 40 | | |
| | | 0.1 | | 220 | 260 | 40 | 45 | −8 |
| | | | | 210 | 260 | 50 | | |
| | | 0.05 | 180 | 220 | 250 | 30 | 25 | 38 |
| | | | | 220 | 240 | 20 | | |
| | | 0.1 | | 210 | 260 | 50 | 47.5 | −14 |
| | | | | 210 | 255 | 45 | | |
| | | 0.05 | 240 | 225 | 260 | 35 | 40 | 0 |
| | | | | 215 | 260 | 45 | | |
| | | 0.1 | | 210 | 260 | 50 | 50 | −20 |
| | | | | 215 | 265 | 50 | | |
| | | 0.05 | 0 | 180 | 210 | 30 | 35.5 | |
| | | | | 192 | 233 | 41 | | |
| | | 0.1 | | 170 | 235 | 65 | 56 | |
| | | | | 190 | 237 | 47 | | |
| Ex. No. 62 | 3 I.V. | 0.05 | 30 | 195 | 210 | 15 | 14 | 61 |
| | | | | 182 | 195 | 13 | | |
| | | 0.1 | | 200 | 205 | 5 | 10 | 82 |
| | | | | 200 | 215 | 15 | | |
| | | 0.05 | 60 | 177 | 193 | 16 | 18 | 49 |
| | | | | 200 | 220 | 20 | | |
| | | 0.1 | | 175 | 210 | 35 | 36 | 36 |
| | | | | 188 | 225 | 37 | | |
| SPONTANEOUSLY HYPERTENSIVE RATS n = 2 Body weight(s): 315, 320 grams | | | | | | | | |
| | | 0.05 | 90 | 185 | 220 | 35 | 30 | 15 |
| | | | | 190 | 215 | 25 | | |
| | | 0.1 | | 180 | 220 | 40 | 40 | 29 |
| | | | | 190 | 230 | 40 | | |
| | | 0.05 | 120 | 170 | 205 | 35 | 25 | 30 |
| | | | | 200 | 215 | 15 | | |
| | | 0.1 | | 180 | 225 | 45 | 35 | 38 |
| | | | | 185 | 210 | 25 | | |
| | | 0.05 | 180 | 160 | 205 | 45 | 33.5 | 6 |
| | | | | 170 | 192 | 22 | | |
| | | 0.1 | | 175 | 210 | 35 | 35 | 38 |

-continued

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| CONTROL | | 0.05 | 0 | 165 | 200 | 35 | 35 | |
| | | | | 205 | 240 | 35 | | |
| | | | | 220 | 255 | 35 | | |
| | | 0.1 | | 200 | 245 | 45 | 37.5 | |
| | | | | 220 | 250 | 30 | | |
| Ex. No. 63 | 3 I.V. | 0.05 | 30 | 200 | 218 | 18 | 10.5 | 70 |
| | | | | 212 | 215 | 3 | | |
| | | 0.1 | | 200 | 215 | 15 | 10 | 73 |
| | | | | 205 | 210 | 5 | | |
| | | 0.5 | 60 | 200 | 210 | 10 | 10 | 71 |
| | | | | 205 | 215 | 10 | | |
| | | 0.1 | | 195 | 210 | 15 | 15 | 60 |
| | | | | 200 | 215 | 15 | | |
| SPONTANEOUSLY HYPERTENSIVE RATS n = 2 Body weight(s): 315, 320 grams | | | | | | | | |
| | | 0.05 | 90 | 190 | 205 | 15 | 10 | 71 |
| | | | | 195 | 200 | 5 | | |
| | | 0.1 | | 190 | 200 | 10 | 17.5 | 53 |
| | | | | 200 | 225 | 25 | | |
| | | 0.05 | 120 | 195 | 205 | 10 | 10 | 71 |
| | | | | 195 | 205 | 10 | | |
| | | 0.1 | | 185 | 203 | 18 | 17.5 | 53 |
| | | | | 190 | 207 | 17 | | |
| | | 0.05 | 180 | 185 | 200 | 15 | 17.5 | 50 |
| | | | | 185 | 205 | 20 | | |
| | | 0.1 | | 185 | 210 | 25 | 22.5 | 40 |
| | | | | 195 | 215 | 20 | | |
| | | 0.05 | 240 | 190 | 205 | 15 | 12.5 | 64 |
| | | | | 190 | 200 | 10 | | |
| | | 0.1 | | 190 | 217 | 27 | 23 | 39 |
| | | | | 193 | 212 | 19 | | |
| | | 0.05 | 300 | 183 | 205 | 22 | 23.5 | 33 |
| | | | | 175 | 200 | 25 | | |
| | | 0.1 | | 185 | 210 | 25 | 25 | 33 |
| | | | | 180 | 205 | 25 | | |
| CONTROL | | 0.05 | 0 | 215 | 260 | 45 | 44 | |
| | | | | 242 | 285 | 43 | | |
| | | 0.1 | | 220 | 260 | 40 | 42.5 | |
| | | | | 230 | 275 | 45 | | |
| SPONTANEOUSLY HYPERTENSIVE RATS n = 2 Body weight(s): 360, 320 grams | | | | | | | | |
| Ex. No. 63 | 5 P.O. | 0.05 | 30 | 220 | 235 | 15 | 22.5 | 49 |
| | | | | 235 | 265 | 30 | | |
| | | 0.1 | | 225 | 245 | 20 | 35 | 18 |
| | | | | 220 | 270 | 50 | | |
| | | 0.05 | 60 | 215 | 235 | 20 | 30 | 32 |
| | | | | 220 | 260 | 40 | | |
| | | 0.1 | | 220 | 255 | 35 | 42.5 | 0 |
| | | | | 210 | 260 | 50 | | |
| | | 0.05 | 90 | 205 | 225 | 20 | 20 | 55 |
| | | | | 220 | 240 | 20 | | |
| | | 0.1 | | 207 | 255 | 48 | 34 | 20 |
| | | | | 230 | 250 | 20 | | |
| | | 0.05 | 120 | 210 | 228 | 18 | 16.5 | 63 |
| | | | | 220 | 235 | 15 | | |
| | | 0.1 | | 200 | 235 | 35 | 32.5 | 24 |
| | | | | 235 | 265 | 30 | | |
| | | 0.05 | 180 | 200 | 215 | 15 | 20 | 55 |
| | | | | 225 | 250 | 25 | | |
| | | 0.1 | | 195 | 218 | 23 | 24 | 44 |
| | | | | 235 | 260 | 25 | | |
| CONTROL | | 0.05 | 0 | 195 | 235 | 40 | 36.5 | |
| | | | | 200 | 233 | 33 | | |
| | | 0.1 | | 200 | 260 | 60 | 54 | |
| | | | | 195 | 243 | 48 | | |
| SPONTANEOUSLY HYPERTENSIVE RATS n = 2 Body weight(s): 360, 280 grams | | | | | | | | |
| Ex. No. 64 | 3 I.V. | 0.05 | 30 | 175 | 175 | 0 | 2.5 | 93 |
| | | | | 190 | 195 | 5 | | |
| | | 0.1 | | 175 | 175 | 0 | 5 | 91 |
| | | | | 185 | 195 | 10 | | |
| | | 0.05 | 60 | 195 | 200 | 5 | 2.5 | 93 |
| | | | | 210 | 210 | 0 | | |
| | | 0.1 | | 190 | 195 | 5 | 5 | 91 |
| | | | | 195 | 200 | 5 | | |
| | | 0.05 | 90 | 190 | 200 | 10 | 7.5 | 79 |
| | | | | 190 | 195 | 5 | | |
| | | 0.1 | | 190 | 200 | 10 | 7.5 | 86 |
| | | | | 190 | 195 | 5 | | |
| | | 0.5 | 120 | 175 | 185 | 10 | 5 | 86 |

-continued

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| | | | | 185 | 185 | 0 | | |
| | | 0.1 | | 175 | 190 | 15 | 10 | 81 |
| | | | | 185 | 190 | 5 | | |
| | | 0.05 | 180 | 175 | 185 | 10 | 7.5 | 79 |
| | | | | 185 | 190 | 5 | | |
| | | 0.1 | | 195 | 200 | 5 | 11 | 80 |
| | | | | 190 | 207 | 17 | | |
| | | 0.05 | 240 | 170 | 188 | 18 | 18 | 51 |
| | | | | 177 | 195 | 18 | | |
| | | 0.1 | | 185 | 200 | 15 | 12.5 | 77 |
| | | | | 200 | 210 | 10 | | |
| SPONTANEOUSLY HYPERTENSIVE RATS n = 2 Body weight(s): 335, 350 grams | | | | | | | | |
| | | 0.05 | 300 | 165 | 175 | 10 | 7.5 | 79 |
| | | | | 200 | 205 | 5 | | |
| | | 0.1 | | 160 | 180 | 20 | 18.5 | 66 |
| | | | | 190 | 207 | 17 | | |
| CONTROL | | 0.05 | 0 | 195 | 216 | 21 | 32.5 | |
| | | | | 180 | 224 | 44 | | |
| | | 0.1 | | 195 | 218 | 23 | 36.5 | |
| | | | | 180 | 230 | 50 | | |
| Ex. No. 64 | 5 P.O. | 0.05 | 30 | 195 | 205 | 10 | 15 | 54 |
| | | | | 195 | 215 | 20 | | |
| | | 0.1 | | 195 | 215 | 20 | 27.5 | 25 |
| | | | | 190 | 225 | 35 | | |
| | | 0.05 | 60 | 195 | 207 | 12 | 18.5 | 43 |
| | | | | 185 | 210 | 25 | | |
| | | 0.1 | | 198 | 210 | 12 | 23.5 | 36 |
| | | | | 185 | 220 | 35 | | |
| | | 0.5 | 90 | 190 | 208 | 18 | 20 | 38 |
| | | | | 178 | 200 | 22 | | |
| | | 0.1 | | 195 | 210 | 15 | 22 | 40 |
| | | | | 178 | 207 | 29 | | |
| | | 0.05 | 120 | 190 | 210 | 20 | 20 | 38 |
| | | | | 175 | 195 | 20 | | |
| | | 0.1 | | 195 | 210 | 15 | 20 | 45 |
| | | | | 185 | 210 | 25 | | |
| SPONTANEOUSLY HYPERTENSIVE RATS n = 2 Body weight(s): 310, 360 grams | | | | | | | | |
| | | 0.05 | 180 | 185 | 200 | 15 | 17.5 | 46 |
| | | | | 180 | 200 | 20 | | |
| | | 0.1 | | 185 | 213 | 28 | 24 | 34 |
| | | | | 180 | 200 | 20 | | |
| CONTROL | | 0.05 | 0 | 205 | 256 | 51 | 45.5 | |
| | | | | 215 | 255 | 40 | | |
| | | 0.1 | | 210 | 255 | 45 | 48.5 | |
| | | | | 210 | 262 | 52 | | |
| Ex. No. 65 | 3 I.V. | 0.05 | 30 | 185 | 185 | 0 | 2.5 | 95 |
| | | | | 195 | 200 | 5 | | |
| | | 0.1 | | 185 | 190 | 5 | 2.5 | 95 |
| | | | | 195 | 195 | 0 | | |
| | | 0.05 | 60 | 185 | 200 | 15 | 15.5 | 66 |
| | | | | 194 | 210 | 16 | | |
| | | 0.1 | | 183 | 190 | 7 | 11 | 77 |
| | | | | 195 | 210 | 15 | | |
| | | 0.05 | 90 | 180 | 187 | 7 | 11 | 76 |
| | | | | 195 | 210 | 15 | | |
| | | 0.1 | | 182 | 195 | 13 | 16.5 | 66 |
| | | | | 185 | 205 | 20 | | |
| | | 0.05 | 120 | 182 | 198 | 16 | 8 | 82 |
| | | | | 210 | 210 | 0 | | |
| | | 0.1 | | 185 | 195 | 10 | 12.5 | 74 |
| | | | | 215 | 230 | 15 | | |
| SPONTANEOUSLY HYPERTENSIVE RATS n = 2 Body weight(s): 340, 300 grams | | | | | | | | |
| | | 0.05 | 180 | 180 | 190 | 10 | 25 | 45 |
| | | | | 195 | 235 | 40 | | |
| | | 0.1 | | 185 | 200 | 15 | 17.5 | 64 |
| | | | | 210 | 230 | 20 | | |
| CONTROL | | 0.05 | 0 | 160 | 207 | 47 | 43.5 | |
| | | | | 210 | 250 | 40 | | |
| | | 0.1 | | 170 | 220 | 50 | 44 | |
| | | | | 210 | 248 | 38 | | |
| Ex. No. 66 | 5 P.O. | 0.05 | 30 | 170 | 175 | 5 | 10 | 77 |
| | | | | 210 | 225 | 15 | | |
| | | 0.1 | | 160 | 175 | 15 | 21 | 52 |
| | | | | 200 | 227 | 27 | | |
| | | 0.05 | 60 | 175 | 175 | 0 | 7.5 | 83 |
| | | | | 210 | 225 | 15 | | |
| | | 0.1 | | 170 | 180 | 10 | 17.5 | 60 |

-continued

| Example No. | Dose (mg/kg) | AII Dose mcg/kg IV | Min Post Dose | Control Before AII | Response After AII | Change | Average Change | % Inhibition |
|---|---|---|---|---|---|---|---|---|
| | | | | 200 | 225 | 25 | | |
| | | 0.05 | 90 | 150 | 150 | 0 | 3 | 93 |
| | | | | 207 | 213 | 6 | | |
| | | 0.1 | | 165 | 165 | 0 | 2.5 | 94 |
| | | | | 200 | 205 | 5 | | |
| | | 0.05 | 120 | 150 | 155 | 5 | 7.5 | 83 |
| | | | | 200 | 210 | 10 | | |
| | | 0.1 | | 165 | 175 | 10 | 7.5 | 83 |
| | | | | 195 | 200 | 5 | | |

SPONTANEOUSLY HYPERTENSIVE RATS n = 2 Body weight(s): 300, 300 grams

| Example No. | Dose (mg/kg) | AII Dose mcg/kg IV | Min Post Dose | Control Before AII | Response After AII | Change | Average Change | % Inhibition |
|---|---|---|---|---|---|---|---|---|
| | | 0.05 | 180 | 155 | 160 | 5 | 5 | 89 |
| | | | | 200 | 205 | 5 | | |
| | | 0.1 | | 155 | 165 | 10 | 12.5 | 72 |
| | | | | 185 | 200 | 15 | | |
| | | 0.05 | 240 | 150 | 155 | 5 | 5 | 89 |
| | | | | 185 | 190 | 5 | | |
| | | 0.1 | | 150 | 155 | 5 | 10 | 77 |
| | | | | 180 | 195 | 15 | | |
| | | 0.05 | 300 | 150 | 160 | 10 | 10 | 77 |
| | | | | 195 | 205 | 10 | | |
| | | 0.1 | | 150 | 160 | 10 | 10 | 77 |
| | | | | 185 | 195 | 10 | | |
| CONTROL | | 0.05 | 0 | 195 | 225 | 30 | 37.5 | |
| | | | | 200 | 245 | 45 | | |
| | | 0.1 | | 185 | 227 | 42 | 43.5 | |
| | | | | 200 | 245 | 45 | | |
| Ex. No. 66 | 1 I.V. | 0.05 | 30 | 180 | 185 | 5 | 2.5 | 93 |
| | | | | 185 | 185 | 0 | | |
| | | 0.1 | | 175 | 185 | 10 | 5 | 89 |
| | | | | 185 | 185 | 0 | | |
| | | 0.05 | 60 | 185 | 185 | 0 | 0 | 100 |
| | | | | 175 | 175 | 0 | | |
| | | 0.1 | | 170 | 175 | 5 | 2.5 | 94 |
| | | | | 170 | 170 | 0 | | |

SPONTANEOUSLY HYPERTENSIVE RATS n = 2 Body weight(s): 300, 270 grams

| Example No. | Dose (mg/kg) | AII Dose mcg/kg IV | Min Post Dose | Control Before AII | Response After AII | Change | Average Change | % Inhibition |
|---|---|---|---|---|---|---|---|---|
| | | 0.05 | 90 | 160 | 175 | 15 | 9 | 76 |
| | | | | 165 | 168 | 3 | | |
| | | 0.1 | | 160 | 175 | 15 | 7.5 | 83 |
| | | | | 170 | 170 | 0 | | |
| | | 0.05 | 120 | 175 | 188 | 13 | 11.5 | 69 |
| | | | | 175 | 185 | 10 | | |
| | | 0.1 | | 175 | 185 | 10 | 7.5 | 83 |
| | | | | 175 | 180 | 5 | | |
| | | 0.05 | 180 | 180 | 205 | 25 | 15 | 60 |
| | | | | 180 | 185 | 5 | | |
| | | 0.1 | | 185 | 203 | 18 | 14 | 68 |
| | | | | 175 | 185 | 10 | | |
| | | 0.05 | 240 | 190 | 200 | 10 | 12.5 | 67 |
| | | | | 200 | 215 | 15 | | |
| | | 0.1 | | 182 | 200 | 18 | 14 | 68 |
| | | | | 180 | 190 | 10 | | |
| | | 0.05 | 300 | 185 | 205 | 20 | 20 | 47 |
| | | | | 175 | 195 | 20 | | |
| | | 0.1 | | 185 | 200 | 15 | 17.5 | 60 |
| | | | | 175 | 195 | 20 | | |
| CONTROL | | 0.05 | 0 | 210 | 273 | 63 | 51.5 | |
| | | | | 200 | 240 | 40 | | |
| | | 0.1 | | 210 | 285 | 75 | 60 | |
| | | | | 200 | 245 | 45 | | |

SPONTANEOUSLY HYPERTENSIVE RATS n = 2 Body weight(s): 300, 270 grams

| Example No. | Dose (mg/kg) | AII Dose mcg/kg IV | Min Post Dose | Control Before AII | Response After AII | Change | Average Change | % Inhibition |
|---|---|---|---|---|---|---|---|---|
| Ex. No. 67 | 3 I.V. | 0.05 | 30 | 185 | 210 | 25 | 20 | 61 |
| | | | | 175 | 190 | 15 | | |
| | | 0.1 | | 177 | 200 | 23 | 14 | 77 |
| | | | | 175 | 180 | 5 | | |
| | | 0.05 | 60 | 185 | 185 | 0 | 7.5 | 85 |
| | | | | 175 | 190 | 15 | | |
| | | 0.1 | | 170 | 190 | 20 | 15 | 75 |
| | | | | 175 | 185 | 10 | | |
| | | 0.05 | 90 | 185 | 190 | 5 | 7.5 | 85 |
| | | | | 175 | 185 | 10 | | |
| | | 0.1 | | 185 | 195 | 10 | 12.5 | 79 |
| | | | | 170 | 185 | 15 | | |
| | | 0.05 | 120 | 170 | 180 | 10 | 12.5 | 76 |
| | | | | 165 | 180 | 15 | | |
| | | 0.1 | | 165 | 175 | 10 | 10 | 83 |
| | | | | 170 | 180 | 10 | | |
| | | 0.05 | 180 | 185 | 200 | 15 | 15 | 71 |

-continued

| | | ANGIOTENSIN II (AII) VASOPRESSOR RESPONSE | | | | | |
|---|---|---|---|---|---|---|---|
| Example No. | Dose (mg/kg) | AII Dose mcg/kg IV | Min Post Dose | Control Before AII | Response After AII | Change | Average Change | % Inhibition |
| | | | | 170 | 185 | 15 | | |
| | | 0.1 | | 175 | 188 | 13 | 11.5 | 81 |
| | | | | 175 | 185 | 10 | | |
| | | 0.05 | 240 | 165 | 180 | 15 | 7.5 | 85 |
| | | | | 170 | 170 | 0 | | |
| | | 0.1 | | 170 | 177 | 7 | 11 | 82 |
| | | | | 170 | 185 | 15 | | |
| SPONTANEOUSLY HYPERTENSIVE RATS n = 2 Body weight(s): 300, 280 grams | | | | | | | | |
| | | 0.05 | 300 | 175 | 188 | 13 | 14 | 73 |
| | | | | 175 | 190 | 15 | | |
| | | 0.1 | | 170 | 190 | 20 | 17.5 | 71 |
| | | | | 185 | 200 | 15 | | |
| CONTROL | | 0.05 | 0 | 170 | 218 | 48 | 51.5 | |
| | | | | 170 | 225 | 55 | | |
| | | 0.1 | | 170 | 225 | 55 | 56 | |
| | | | | 170 | 227 | 57 | | |
| Ex. No. 68 | 3 I.V. | 0.05 | 30 | 170 | 175 | 5 | 2.5 | 95 |
| | | | | 165 | 165 | 0 | | |
| | | 0.1 | | 165 | 175 | 10 | 5 | 91 |
| | | | | 165 | 165 | 0 | | |
| | | 0.05 | 60 | 165 | 170 | 5 | 2.5 | 95 |
| | | | | 165 | 165 | 0 | | |
| | | 0.1 | | 162 | 170 | 8 | 9 | 84 |
| | | | | 155 | 165 | 10 | | |
| | | 0.05 | 90 | 165 | 175 | 10 | 7.5 | 85 |
| | | | | 165 | 170 | 5 | | |
| | | 0.1 | | 167 | 180 | 13 | 9 | 84 |
| | | | | 165 | 170 | 5 | | |
| | | 0.05 | 120 | 165 | 182 | 17 | 11 | 79 |
| | | | | 175 | 180 | 5 | | |
| | | 0.1 | | 165 | 180 | 15 | 10 | 82 |
| | | | | 170 | 175 | 5 | | |
| SPONTANEOUSLY HYPERTENSIVE RATS n = 2 Body weight(s): 360, 330 grams | | | | | | | | |
| | | 0.05 | 180 | 175 | 190 | 15 | 10 | 81 |
| | | | | 165 | 170 | 5 | | |
| | | 0.1 | | 175 | 200 | 25 | 20 | 64 |
| | | | | 170 | 185 | 15 | | |
| | | 0.05 | 240 | 175 | 195 | 20 | 20 | 61 |
| | | | | 155 | 175 | 20 | | |
| | | 0.1 | | 180 | 205 | 25 | 17.5 | 69 |
| | | | | 175 | 185 | 10 | | |
| | | 0.05 | 300 | 165 | 175 | 10 | 10 | 81 |
| | | | | 175 | 185 | 10 | | |
| | | 0.1 | | 165 | 190 | 25 | 22.5 | 60 |
| | | | | 170 | 190 | 20 | | |
| CONTROL | | 0.05 | 0 | 200 | 230 | 30 | 30 | |
| | | | | 200 | 230 | 30 | | |
| | | 0.1 | | 200 | 238 | 38 | 40 | |
| | | | | 195 | 237 | 42 | | |
| Ex. No. 69 | 3 I.V. | 0.05 | 30 | 165 | 165 | 0 | 0 | 100 |
| | | | | 175 | 175 | 0 | | |
| | | 0.1 | | 170 | 170 | 0 | 0 | 100 |
| | | | | 170 | 170 | 0 | | |
| | | 0.05 | 60 | 175 | 180 | 5 | 2.5 | 92 |
| | | | | 185 | 185 | 0 | | |
| | | 0.1 | | 175 | 175 | 0 | 0 | 100 |
| | | | | 180 | 180 | 0 | | |
| SPONTANEOUSLY HYPERTENSIVE RATS n = 2 Body weight(s): 280, 305 grams | | | | | | | | |
| | | 0.05 | 90 | 175 | 180 | 5 | 2.5 | 92 |
| | | | | 180 | 180 | 0 | | |
| | | 0.1 | | 175 | 180 | 5 | 25 | 94 |
| | | | | 180 | 180 | 0 | | |
| | | 0.05 | 120 | 180 | 190 | 10 | 5 | 83 |
| | | | | 185 | 185 | 0 | | |
| | | 0.1 | | 185 | 190 | 5 | 2.5 | 94 |
| | | | | 185 | 185 | 0 | | |
| | | 0.05 | 180 | 185 | 190 | 5 | 2.5 | 92 |
| | | | | 185 | 185 | 0 | | |
| | | 0.1 | | 185 | 185 | 0 | 0 | 100 |
| | | | | 185 | 185 | 0 | | |
| | | 0.05 | 240 | 185 | 185 | 0 | 5 | 83 |
| | | | | 190 | 200 | 10 | | |
| | | 0.1 | | 180 | 185 | 5 | 7.5 | 81 |
| | | | | 185 | 195 | 10 | | |
| | | 0.05 | 300 | 175 | 185 | 10 | 10 | 67 |
| | | | | 190 | 200 | 10 | | |
| | | 0.1 | | 175 | 190 | 15 | 12.5 | 69 |

-continued

| | | ANGIOTENSIN II (AII) VASOPRESSOR RESPONSE | | | | | |
|---|---|---|---|---|---|---|---|
| Example No. | Dose (mg/kg) | AII Dose mcg/kg IV | Min Post Dose | Control Before AII | Response After AII | Change | Average Change | % Inhibition |
| CONTROL | | 0.05 | 0 | 185 | 195 | 10 | | |
| | | | | 250 | 290 | 40 | 45 | |
| | | | | 240 | 290 | 50 | | |
| | | 0.1 | | 255 | 295 | 40 | 47.5 | |
| | | | | 240 | 295 | 55 | | |

SPONTANEOUSLY HYPERTENSIVE RATS n = 2 Body weight(s): 280, 305 grams

| Ex. No. 70 | 1 I.V. | 0.05 | 30 | 255 | 267 | 12 | 23.5 | 48 |
| | | | | 235 | 270 | 35 | | |
| | | 0.1 | | 260 | 275 | 15 | 30 | 37 |
| | | | | 235 | 280 | 45 | | |
| | | 0.05 | 60 | 250 | 260 | 10 | 12.5 | 72 |
| | | | | 270 | 285 | 15 | | |
| | | 0.1 | | 250 | 270 | 20 | 17.5 | 63 |
| | | | | 270 | 285 | 15 | | |
| | | 0.05 | 90 | 240 | 250 | 10 | 12.5 | 72 |
| | | | | 250 | 265 | 15 | | |
| | | 0.1 | | 250 | 266 | 16 | 30.5 | 36 |
| | | | | 235 | 280 | 45 | | |
| | | 0.05 | 120 | 235 | 250 | 15 | 20 | 56 |
| | | | | 230 | 255 | 25 | | |
| | | 0.1 | | 235 | 255 | 20 | 26 | 45 |
| | | | | 220 | 252 | 32 | | |
| | | 0.05 | 180 | 235 | 260 | 25 | 20 | 56 |
| | | | | 235 | 250 | 15 | | |
| | | 0.1 | | 235 | 260 | 25 | 30 | 37 |
| | | | | 235 | 270 | 35 | | |
| | | 0.05 | 240 | 230 | 250 | 20 | 27.5 | 39 |
| | | | | 225 | 260 | 35 | | |
| | | 0.1 | | 230 | 255 | 25 | 30 | 37 |
| | | | | 225 | 260 | 35 | | |

SPONTANEOUSLY HYPERTENSIVE RATS n = 2 Body weight(s): 360, 360 grams

| | | 0.05 | 300 | 235 | 255 | 20 | 30 | 33 |
| | | | | 230 | 270 | 40 | | |
| | | 0.1 | | 230 | 255 | 25 | 37.5 | 21 |
| | | | | 230 | 280 | 50 | | |
| CONTROL | | 0.05 | 0 | 240 | 280 | 40 | 42.5 | |
| | | | | 230 | 275 | 45 | | |
| | | 0.1 | | 250 | 285 | 35 | 37.5 | |
| | | | | 235 | 275 | 40 | | |
| Ex. No. 71 | 1 I.V. | 0.05 | 30 | 245 | 245 | 0 | 20 | 53 |
| | | | | 210 | 250 | 40 | | |
| | | 0.1 | | 225 | 240 | 15 | 15 | 60 |
| | | | | 220 | 235 | 15 | | |
| | | 0.05 | 60 | 240 | 240 | 0 | 5 | 88 |
| | | | | 215 | 225 | 10 | | |
| | | 0.1 | | 220 | 235 | 15 | 15 | 60 |
| | | | | 210 | 225 | 15 | | |
| | | 0.05 | 90 | 225 | 260 | 35 | 30 | 29 |
| | | | | 210 | 235 | 25 | | |
| | | 0.1 | | 210 | 220 | 10 | 20 | 47 |
| | | | | 210 | 240 | 30 | | |
| | | 0.05 | 120 | 205 | 215 | 10 | 15 | 65 |
| | | | | 200 | 220 | 20 | | |
| | | 0.1 | | 210 | 220 | 10 | 10 | 73 |
| | | | | 205 | 215 | 10 | | |

SPONTANEOUSLY HYPERTENSIVE RATS n = 2 Body weight(s): 355, 365 grams

| | | 0.05 | 180 | 205 | 210 | 5 | 15 | 65 |
| | | | | 200 | 225 | 25 | | |
| | | 0.1 | | 200 | 220 | 20 | 15 | 60 |
| | | | | 210 | 220 | 10 | | |
| | | 0.05 | 240 | 210 | 210 | 0 | 15 | 65 |
| | | | | 195 | 225 | 30 | | |
| | | 0.1 | | 210 | 215 | 5 | 22.5 | 40 |
| | | | | 200 | 240 | 40 | | |
| | | 0.05 | 300 | 210 | 215 | 5 | 20 | 53 |
| | | | | 195 | 230 | 35 | | |
| | | 0.1 | | 210 | 215 | 5 | 23.5 | 37 |
| | | | | 200 | 242 | 42 | | |
| CONTROL | | 0.05 | 0 | 185 | 240 | 55 | 50 | |
| | | | | 235 | 280 | 45 | | |
| | | 0.1 | | 190 | 250 | 60 | 60 | |
| | | | | 235 | 295 | 60 | | |
| Ex. No. 72 | 1 I.V. | 0.05 | 30 | 180 | 195 | 15 | 20 | 60 |
| | | | | 220 | 245 | 25 | | |
| | | 0.1 | | 174 | 210 | 36 | 25.5 | 58 |
| | | | | 230 | 245 | 15 | | |
| | | 0.05 | 60 | 195 | 210 | 15 | 15 | 70 |

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| | | | | 225 | 240 | 15 | | |
| | | 0.1 | | 195 | 215 | 20 | 17.5 | 71 |
| | | | | 225 | 240 | 15 | | |
| SPONTANEOUSLY HYPERTENSIVE RATS n = 2 Body weight(s): 370, 350 grams | | | | | | | | |
| | | 0.05 | 90 | 185 | 205 | 20 | 17.5 | 65 |
| | | | | 210 | 225 | 15 | | |
| | | 0.1 | | 185 | 230 | 45 | 32.5 | 46 |
| | | | | 205 | 225 | 20 | | |
| | | 0.05 | 120 | 160 | 190 | 30 | 22.5 | 55 |
| | | | | 235 | 250 | 15 | | |
| | | 0.1 | | 190 | 215 | 25 | 25 | 58 |
| | | | | 215 | 240 | 25 | | |
| | | 0.05 | 180 | 175 | 225 | 50 | 36.5 | 27 |
| | | | | 205 | 228 | 23 | | |
| | | 0.1 | | 175 | 225 | 50 | 35 | 42 |
| | | | | 210 | 230 | 20 | | |
| | | 0.05 | 240 | 180 | 200 | 20 | 30 | 40 |
| | | | | 200 | 240 | 40 | | |
| | | 0.1 | | 195 | 240 | 45 | 40 | |
| | | | | 210 | 245 | 35 | | |
| | | 0.05 | 300 | 180 | 205 | 25 | 37.5 | 35 |
| | | | | 200 | 250 | 50 | | |
| | | 0.1 | | 180 | 210 | 30 | 42.5 | 29 |
| | | | | 205 | 260 | 55 | | |
| SPONTANEOUSLY HYPERTENSIVE RATS n = 2 Body weight(s): 370, 350 grams | | | | | | | | |
| CONTROL | | 0.05 | 0 | 250 | 285 | 35 | 37.5 | |
| | | | | 230 | 270 | 40 | | |
| | | 0.1 | | 250 | 295 | 45 | 45 | |
| | | | | 245 | 290 | 45 | | |
| 73 | 0.5 i.v. | 0.05 | 30 | 225 | 240 | 15 | 10 | 73 |
| | | | | 225 | 230 | 5 | | |
| | | 0.1 | | 235 | 250 | 15 | 15 | 67 |
| | | | | 225 | 240 | 15 | | |
| | | 0.05 | 60 | 225 | 240 | 15 | 11 | 71 |
| | | | | 220 | 227 | 7 | | |
| | | 0.1 | | 225 | 255 | 30 | 27.5 | 39 |
| | | | | 225 | 250 | 25 | | |
| | | 0.05 | 90 | 245 | 255 | 10 | 7.5 | 80 |
| | | | | 240 | 245 | 5 | | |
| | | 0.1 | | 240 | 270 | 30 | 22.5 | 50 |
| | | | | 235 | 250 | 15 | | |
| | | 0.05 | 120 | 240 | 260 | 20 | 17.5 | 53 |
| | | | | 235 | 250 | 15 | | |
| | | 0.1 | | 240 | 275 | 35 | 30 | 33 |
| | | | | 235 | 260 | 25 | | |
| | | 0.05 | 180 | 245 | 265 | 20 | 20 | 47 |
| | | | | 235 | 255 | 20 | | |
| | | 0.1 | | 235 | 268 | 33 | 30.5 | 32 |
| | | | | 237 | 265 | 28 | | |
| | | 0.05 | 240 | 235 | 265 | 30 | 32.5 | 13 |
| | | | | 230 | 265 | 35 | | |
| | | 0.1 | | 240 | 260 | 20 | 27.5 | 39 |
| | | | | 230 | 265 | 35 | | |
| | | 0.05 | 300 | 235 | 255 | 20 | 32.5 | 13 |
| | | | | 225 | 270 | 45 | | |
| | | 0.1 | | 255 | 270 | 15 | 25 | 44 |
| | | | | 230 | 265 | 35 | | |
| SPONTANEOUSLY HYPERTENSIVE RATS n = 2 Body weight(s): 420, 410 grams | | | | | | | | |
| CONTROL | | 0.05 | 0 | 245 | 290 | 45 | 42.5 | |
| | | | | 255 | 295 | 40 | | |
| | | 0.1 | | 245 | 290 | 45 | 44 | |
| | | | | 255 | 298 | 43 | | |
| Ex No. 73 | 0.5 i.v. | 0.05 | 30 | 225 | 240 | 15 | 10 | 76 |
| | | | | 250 | 255 | 5 | | |
| | | 0.1 | | 225 | 240 | 15 | 17.5 | 60 |
| | | | | 235 | 255 | 20 | | |
| | | 0.05 | 60 | 230 | 240 | 10 | 11 | 74 |
| | | | | 245 | 257 | 12 | | |
| | | 0.1 | | 235 | 250 | 15 | 17.5 | 60 |
| | | | | 240 | 260 | 20 | | |
| | | 0.05 | 90 | 245 | 245 | 0 | 2.5 | 94 |
| | | | | 250 | 255 | 5 | | |
| | | | | 250 | 255 | 5 | | |
| | | 0.1 | | 235 | 245 | 10 | 15 | 66 |
| | | | | 235 | 255 | 20 | | |
| | | 0.05 | 120 | 25 | 245 | 10 | 10 | 76 |
| | | | | 235 | 245 | 10 | | |

-continued

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| | | 0.1 | | 245 | 260 | 15 | 17.5 | 60 |
| | | | | 235 | 255 | 20 | | |
| | | 0.05 | 180 | 225 | 235 | 10 | 10 | 76 |
| | | | | 240 | 250 | 10 | | |
| | | 0.1 | | 230 | 250 | 20 | 25 | 43 |
| | | | | 25 | 265 | 30 | | |
| | | 0.05 | 240 | 240 | 247 | 7 | 21 | 51 |
| | | | | 240 | 275 | 35 | | |
| | | 0.1 | | 240 | 260 | 20 | 22.5 | 49 |
| | | | | 250 | 275 | 25 | | |
| | | 0.05 | 300 | 240 | 245 | 5 | 5 | 88 |
| | | | | 240 | 245 | 5 | | |
| | | 0.1 | | 235 | 245 | 10 | 12.5 | 72 |
| | | | | 245 | 260 | 15 | | |
| SPONTANEOUSLY HYPERTENSIVE RATS n = 2 Body weight(s): 400, 400 grams | | | | | | | | |
| CONTROL | | 0.05 | 0 | 220 | 260 | 40 | 40 | |
| | | | | 210 | 250 | 40 | | |
| | | 0.1 | | 225 | 270 | 45 | 45 | |
| | | | | 210 | 225 | 45 | | |
| EX. NO. 73 | 0.5 i.v. | 0.05 | 30 | 210 | 220 | 10 | 10 | 75 |
| | | | | 180 | 190 | 10 | | |
| | | 0.1 | | 205 | 225 | 20 | 17 | 62 |
| | | | | 183 | 197 | 14 | | |
| | | 0.05 | 60 | 205 | 215 | 10 | 12.5 | 69 |
| | | | | 210 | 225 | 15 | | |
| | | 0.1 | | 200 | 225 | 25 | 17.5 | 61 |
| | | | | 215 | 225 | 10 | | |
| | | 0.05 | 90 | 210 | 220 | 10 | 10 | 75 |
| | | | | 190 | 200 | 10 | | |
| | | 0.1 | | 210 | 230 | 20 | 17.5 | 61 |
| | | | | 195 | 210 | 15 | | |
| | | 0.05 | 120 | 230 | 240 | 10 | 12.5 | 69 |
| | | | | 190 | 205 | 15 | | |
| | | 0.1 | | 225 | 245 | 20 | 22.5 | 50 |
| | | | | 190 | 215 | 25 | | |
| | | 0.05 | 180 | 215 | 230 | 15 | 15 | 63 |
| | | | | 190 | 205 | 15 | | |
| | | 0.1 | | 220 | 245 | 25 | 25 | 44 |
| | | | | 190 | 215 | 25 | | |
| | | 0.05 | 240 | 210 | 240 | 30 | 30 | 25 |
| | | | | 185 | 215 | 30 | | |
| | | 0.1 | | 220 | 235 | 15 | 25 | 44 |
| | | | | 185 | 220 | 35 | | |
| | | 0.05 | 300 | 215 | 240 | 25 | 22 | 45 |
| | | | | 188 | 207 | 19 | | |
| | | 0.1 | | 225 | 255 | 30 | 30 | 33 |
| | | | | 190 | 220 | 30 | | |
| SPONTANEOUSLY HYPERTENSIVE RATS n = 2 Body weight(s): 390, 370 grams | | | | | | | | |
| CONTROL | | 0.05 | 0 | 230 | 270 | 40 | 35 | |
| | | | | 225 | 255 | 30 | | |
| | | 0.1 | | 235 | 285 | 50 | 37.5 | |
| | | | | 225 | 250 | 25 | | |
| EX. NO. 73 | 0.5 i.v. | 0.05 | 30 | 205 | 210 | 5 | 7.5 | 79 |
| | | | | 195 | 205 | 10 | | |
| | | 0.1 | | 215 | 220 | 5 | 10 | 73 |
| | | | | 195 | 210 | 15 | | |
| | | 0.05 | 60 | 210 | 220 | 10 | 10 | 71 |
| | | | | 205 | 215 | 10 | | |
| | | 0.1 | | 220 | 230 | 10 | 10 | 73 |
| | | | | 210 | 220 | 10 | | |
| | | 0.05 | 90 | 220 | 230 | 10 | 10 | 71 |
| | | | | 210 | 220 | 10 | | |
| | | 0.1 | | 230 | 245 | 15 | 15 | 60 |
| | | | | 210 | 225 | 15 | | |
| | | 0.05 | 120 | 225 | 240 | 15 | 25 | 29 |
| | | | | 205 | 250 | 35 | | |
| | | 0.1 | | 220 | 240 | 20 | 27.5 | 27 |
| | | | | 210 | 245 | 35 | | |
| | | 0.05 | 180 | 225 | 240 | 15 | 22.5 | 36 |
| | | | | 215 | 245 | 30 | | |
| | | 0.1 | | 215 | 235 | 20 | 17.5 | 53 |
| | | | | 220 | 235 | 15 | | |
| | | 0.05 | 240 | 215 | 235 | 20 | 15 | 57 |
| | | | | 215 | 225 | 10 | | |
| | | 0.1 | | 230 | 245 | 15 | 25 | 33 |
| | | | | 200 | 235 | 35 | | |
| | | 0.05 | 300 | 205 | 220 | 15 | 17.5 | 50 |
| | | | | 220 | 240 | 20 | | |

-continued

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| | | 0.1 | | 210 | 235 | 25 | 25 | 33 |
| | | | | 220 | 245 | 25 | | |
| SPONTANEOUSLY HYPERTENSIVE RATS n = 2 Body weight(s): 350, 370 grams | | | | | | | | |
| CONTROL | | 0.05 | 0 | 250 | 275 | 25 | 32.5 | |
| | | | | 225 | 265 | 40 | | |
| | | 0.1 | | 250 | 275 | 25 | 37.5 | |
| | | | | 225 | 275 | 50 | | |
| EX. NO. 73 | 1 p.o. | 0.05 | 30 | 250 | 265 | 15 | 22.5 | 31 |
| | | | | 225 | 255 | 30 | | |
| | | 0.1 | | 245 | 265 | 20 | 27.5 | 27 |
| | | | | 225 | 260 | 35 | | |
| | | 0.05 | 60 | 260 | 270 | 10 | 12.5 | 62 |
| | | | | 230 | 245 | 15 | | |
| | | 0.1 | | 255 | 265 | 10 | 20 | 47 |
| | | | | 230 | 260 | 30 | | |
| | | 0.05 | 90 | 245 | 260 | 15 | 20 | 38 |
| | | | | 215 | 240 | 25 | | |
| | | 0.1 | | 245 | 265 | 20 | 22.5 | 40 |
| | | | | 220 | 245 | 25 | | |
| | | 0.05 | 120 | 250 | 260 | 10 | 12.5 | 62 |
| | | | | 215 | 230 | 15 | | |
| | | 0.1 | | 245 | 270 | 25 | 22.5 | 40 |
| | | | | 225 | 245 | 20 | | |
| | | 0.05 | 180 | 245 | 275 | 30 | 25 | 23 |
| | | | | 220 | 240 | 20 | | |
| | | 0.1 | | 250 | 265 | 15 | 22.5 | 40 |
| | | | | 225 | 255 | 30 | | |
| | | 0.05 | 240 | 240 | 270 | 30 | 27.5 | 15 |
| | | | | 225 | 250 | 25 | | |
| | | 0.1 | | 240 | 265 | 25 | 25 | 33 |
| | | | | 235 | 260 | 25 | | |
| | | 0.05 | 300 | 240 | 260 | 20 | 25 | 23 |
| | | | | 210 | 240 | 30 | | |
| | | 0.1 | | 245 | 260 | 15 | 22.5 | 40 |
| | | | | 215 | 245 | 30 | | |
| SPONTANEOUSLY HYPERTENSIVE RATS n = 2 Body weight(s): 380, 370 grams | | | | | | | | |
| CONTROL | | 0.05 | 0 | 205 | 250 | 45 | 33.3 | |
| | | | | 230 | 255 | 25 | | |
| | | 0.1 | | 220 | 255 | 30 | 33.3 | |
| | | | | 230 | 260 | 10 | | |
| EX. NO. 73 | 0.1 i.v. | 0.05 | 30 | 210 | 230 | 20 | 13.3 | 60 |
| | | | | 220 | 230 | 10 | | |
| | | | | 225 | 235 | 10 | | |
| | | 0.1 | | 210 | 240 | 30 | 21.7 | 35 |
| | | | | 220 | 235 | 15 | | |
| | | | | 230 | 250 | 20 | | |
| | | 0.05 | 60 | 210 | 235 | 25 | 20.0 | 40 |
| | | | | 220 | 25 | 15 | | |
| | | | | 230 | 250 | 20 | | |
| | | 0.1 | | 210 | 240 | 30 | 25 | 25 |
| | | | | 225 | 245 | 20 | | |
| | | | | 235 | 260 | 25 | | |
| | | 0.05 | 90 | 210 | 235 | 25 | 20.0 | 40 |
| | | | | 230 | 245 | 15 | | |
| | | | | 235 | 255 | 20 | | |
| | | 0.1 | | 205 | 240 | 35 | 30.0 | 60 |
| | | | | 220 | 245 | 25 | | |
| | | | | 235 | 265 | 30 | | |
| | | 0.05 | 120 | 195 | 235 | 40 | 28.3 | 15 |
| | | | | 215 | 240 | 25 | | |
| | | | | 240 | 260 | 20 | | |
| | | 0.1 | | 198 | 240 | 42 | 32.3 | 3 |
| | | | | 230 | 250 | 20 | | |
| | | | | 235 | 270 | 35 | | |
| SPONTANEOUSLY HYPERTENSIVE RATS n = 3 Body weight(s): 360, 390, 360 grams | | | | | | | | |
| | | 0.05 | 180 | 200 | 240 | 40 | 36.7 | −10 |
| | | | | 220 | 245 | 25 | | |
| | | | | 230 | 275 | 45 | | |
| | | 0.1 | | 200 | 240 | 40 | 33.5 | 0 |
| | | | | 235 | 260 | 25 | | |
| | | | | 235 | 270 | 35 | | |
| CONTROL | | 0.05 | 0 | 245 | 275 | 30 | 40 | |
| | | | | 220 | 270 | 50 | | |
| | | | | 215 | 255 | 40 | | |
| | | 0.1 | | 240 | 280 | 40 | 41.7 | |
| | | | | 225 | 270 | 45 | | |
| | | | | 220 | 260 | 40 | | |

-continued

| Example No. | Dose (mg/kg) | ANGIOTENSIN II (AII) VASOPRESSOR RESPONSE | | | | | Average Change | % Inhibition |
|---|---|---|---|---|---|---|---|---|
| | | AII Dose mcg/kg IV | Min Post Dose | Control Before AII | Response After AII | Change | | |
| EX. NO. 73 | 0.1 i.v | 0.05 | 240 | 195 | 235 | 40 | 36.7 | 8 |
| | | | | 225 | 255 | 30 | | |
| | | | | 230 | 270 | 40 | | |
| | | 0.1 | | 185 | 245 | 60 | 41.7 | 0 |
| | | | | 225 | 255 | 30 | | |
| | | | | 240 | 275 | 35 | | |
| | | 0.05 | 300 | 220 | 250 | 30 | 30 | 25 |
| | | | | 220 | 250 | 30 | | |
| | | | | 230 | 260 | 30 | | |
| | | 0.1 | | 210 | 255 | 45 | 40 | 4 |
| | | | | 220 | 255 | 35 | | |
| | | | | 230 | 270 | 40 | | |
| SPONTANEOUSLY HYPERTENSIVE RATS n = 3 Body weight(s): 360, 390, 360 grams | | | | | | | | |
| CONTROL | | 0.05 | 0 | 245 | 285 | 40 | 36.7 | |
| | | | | 250 | 285 | 35 | | |
| | | | | 235 | 270 | 35 | | |
| | | 0.1 | | 245 | 280 | 35 | 40.0 | |
| | | | | 245 | 290 | 45 | | |
| | | | | 240 | 280 | 40 | | |
| EX. NO. 73 | 0.3 i.v. | 0.05 | 30 | 225 | 255 | 30 | 28.3 | 23 |
| | | | | 225 | 245 | 20 | | |
| | | | | 215 | 250 | 35 | | |
| | | 0.1 | | 225 | 250 | 25 | 23.3 | 42 |
| | | | | 225 | 245 | 20 | | |
| | | | | 210 | 235 | 25 | | |
| | | 0.05 | 60 | 230 | 255 | 25 | 26.7 | 27 |
| | | | | 225 | 250 | 25 | | |
| | | | | 230 | 260 | 30 | | |
| | | 0.1 | | 225 | 255 | 30 | 30 | 25 |
| | | | | 230 | 260 | 30 | | |
| | | | | 230 | 260 | 30 | | |
| | | 0.05 | 90 | 230 | 245 | 15 | 19.0 | 48 |
| | | | | 230 | 252 | 22 | | |
| | | | | 240 | 260 | 20 | | |
| | | 0.1 | | 230 | 255 | 25 | 21.7 | 29 |
| | | | | 240 | 260 | 20 | | |
| | | | | 240 | 260 | 20 | | |
| | | 0.05 | 120 | 220 | 240 | 20 | 21.7 | 41 |
| | | | | 230 | 250 | 20 | | |
| | | | | 230 | 255 | 25 | | |
| | | 0.1 | | 220 | 245 | 25 | 25.0 | 38 |
| | | | | 240 | 265 | 25 | | |
| | | | | 235 | 260 | 25 | | |
| | | 0.05 | 180 | 215 | 245 | 30 | 23.3 | 36 |
| | | | | 230 | 245 | 15 | | |
| | | | | 230 | 255 | 25 | | |
| | | 0.1 | | 225 | 265 | 40 | 26.7 | 33 |
| | | | | 230 | 265 | 15 | | |
| | | | | 230 | 260 | 25 | | |
| SPONTANEOUSLY HYPERTENSIVE RATS n = 3 Body weight(s): 350, 380, 380 grams | | | | | | | | |
| CONTROL | | 0.05 | 0 | 245 | 285 | 40 | 36.7 | |
| | | | | 250 | 285 | 35 | | |
| | | | | 35 | 270 | 35 | | |
| | | 0.1 | | 245 | 280 | 35 | 40.0 | |
| | | | | 245 | 290 | 45 | | |
| | | | | 240 | 280 | 40 | | |
| EX. NO. 73 | 0.3 i.v. | 0.05 | 240 | 225 | 240 | 15 | 28.3 | 23 |
| | | | | 225 | 260 | 35 | | |
| | | | | 225 | 260 | 35 | | |
| | | 0.1 | | 210 | 250 | 40 | 38.3 | 4 |
| | | | | 225 | 275 | 50 | | |
| | | | | 235 | 260 | 25 | | |
| | | 0.05 | 300 | 210 | 235 | 25 | 28.3 | 23 |
| | | | | 215 | 240 | 25 | | |
| | | | | 24t | 280 | 35 | | |
| | | 0.1 | | 210 | 260 | 50 | 40 | 0 |
| | | | | 220 | 265 | 45 | | |
| | | | | 260 | 285 | 256 | | |
| SPONTANEOUSLY HYPERTENSIVE RATS n = 3 Body weight(s): 350, 380, 380 grams | | | | | | | | |
| CONTROL | | 0.05 | 0 | 195 | 225 | 30 | 37.5 | |
| | | | | 215 | 260 | 45 | | |
| | | 0.1 | | 210 | 240 | 30 | 35 | |
| | | | | 245 | 285 | 40 | | |
| EX. NO. 73 | 0.1 i.v. | 0.05 | 30 | 215 | 235 | 20 | 17.5 | 53 |
| | | | | 240 | 255 | 15 | | |
| | | 0.1 | | 215 | 240 | 25 | 30 | 14 |
| | | | | 225 | 260 | 35 | | |

-continued

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| | | 0.05 | 60 | 230 | 250 | 20 | 17.5 | 53 |
| | | | | 225 | 240 | 15 | | |
| | | 0.1 | | 215 | 255 | 40 | 35 | 0 |
| | | | | 225 | 255 | 30 | | |
| | | 0.05 | 90 | 245 | 270 | 25 | 30 | 20 |
| | | | | 215 | 250 | 35 | | |
| | | 0.1 | | 230 | 270 | 40 | 37.5 | −7 |
| | | | | 225 | 260 | 35 | | |
| | | 0.05 | 120 | 235 | 270 | 35 | 35 | 7 |
| | | | | 230 | 265 | 35 | | |
| | | 0.1 | | 245 | 275 | 30 | 40 | −14 |
| | | | | 225 | 275 | 50 | | |
| | | 0.05 | 180 | 235 | 250 | 15 | 25 | 33 |
| | | | | 230 | 265 | 35 | | |
| | | 0.1 | | 230 | 265 | 35 | 40 | −14 |
| | | | | 225 | 270 | 45 | | |
| | | 0.05 | 240 | 205 | 235 | 30 | 25 | 33 |
| | | | | 250 | 270 | 20 | | |
| | | 0.1 | | 205 | 240 | 35 | 32.5 | 7 |
| | | | | 235 | 265 | 30 | | |
| | | 0.05 | 300 | 210 | 245 | 35 | 42.5 | −13 |
| | | | | 230 | 280 | 50 | | |
| | | 0.1 | | 210 | 245 | 35 | 32.5 | 7 |
| | | | | 225 | 255 | 30 | | |
| SPONTANEOUSLY HYPERTENSIVE RATS n = 2 Body weight(s): 380, 350 grams | | | | | | | | |
| CONTROL | | 0.05 | 0 | 250 | 280 | 30 | 37.5 | |
| | | | | 245 | 290 | 45 | | |
| | | 0.1 | | 245 | 285 | 40 | 50 | |
| | | | | 245 | 305 | 60 | | |
| EX. NO. 73 | 0.1 i.v. | 0.05 | 30 | 240 | 245 | 5 | 7.5 | 80 |
| | | | | 230 | 240 | 10 | | |
| | | 0.1 | | 230 | 255 | 25 | 20 | 60 |
| | | | | 230 | 245 | 15 | | |
| | | 0.05 | 60 | 245 | 270 | 25 | 25 | 33 |
| | | | | 235 | 260 | 25 | | |
| | | 0.1 | | 245 | 270 | 25 | 22.5 | 55 |
| | | | | 235 | 255 | 20 | | |
| | | 0.05 | 90 | 245 | 265 | 20 | 15 | 60 |
| | | | | 235 | 245 | 10 | | |
| | | 0.1 | | 240 | 265 | 25 | 22.5 | 55 |
| | | | | 240 | 260 | 20 | | |
| | | 0.05 | 120 | 235 | 255 | 20 | 22.5 | 40 |
| | | | | 230 | 255 | 25 | | |
| | | 0.1 | | 235 | 270 | 35 | 30 | 40 |
| | | | | 240 | 265 | 25 | | |
| | | 0.05 | 180 | 235 | 260 | 25 | 27.5 | 27 |
| | | | | 235 | 265 | 30 | | |
| | | 0.1 | | 240 | 265 | 25 | 32.5 | 35 |
| | | | | 235 | 275 | 40 | | |
| | | 0.05 | 240 | 235 | 255 | 20 | 22.5 | 40 |
| | | | | 225 | 250 | 25 | | |
| | | 0.1 | | 240 | 255 | 15 | 17.5 | 65 |
| | | | | 225 | 245 | 20 | | |
| | | 0.05 | 300 | 215 | 245 | 30 | 25 | 33 |
| | | | | 230 | 250 | 20 | | |
| | | 0.1 | | 220 | 245 | 25 | 25 | 50 |
| | | | | 230 | 255 | 25 | | |
| SPONTANEOUSLY HYPERTENSIVE RATS n = 2 Body weight(s): 350, 350 grams | | | | | | | | |
| CONTROL | | 0.05 | 0 | 260 | 300 | 40 | 32.5 | |
| | | | | 255 | 280 | 25 | | |
| | | 0.1 | | 260 | 307 | 47 | 36 | |
| | | | | 255 | 280 | 25 | | |
| EX. NO. 73 | 0.3 i.v. | 0.05 | 30 | 245 | 265 | 20 | 15 | 54 |
| | | | | 235 | 245 | 10 | | |
| | | 0.1 | | 245 | 265 | 20 | 16.5 | 54 |
| | | | | 235 | 248 | 13 | | |
| | | 0.05 | 60 | 255 | 270 | 15 | 12.5 | 62 |
| | | | | 235 | 245 | 10 | | |
| | | 0.1 | | 240 | 270 | 30 | 27.5 | 24 |
| | | | | 230 | 255 | 25 | | |
| | | 0.05 | 90 | 260 | 280 | 20 | 17.5 | 46 |
| | | | | 240 | 255 | 15 | | |
| | | 0.1 | | 260 | 280 | 20 | 20 | 44 |
| | | | | 240 | 260 | 20 | | |
| | | 0.05 | 120 | 260 | 280 | 20 | 17.5 | 46 |
| | | | | 225 | 240 | 15 | | |
| | | 0.1 | | 240 | 265 | 25 | 22.5 | 38 |
| | | | | 225 | 245 | 20 | | |

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| | | 0.05 | 180 | 240 | 270 | 30 | 22.5 | 31 |
| | | | | 215 | 230 | 15 | | |
| | | 0.1 | | 255 | 290 | 35 | 30 | 17 |
| | | | | 220 | 245 | 25 | | |
| | | 0.05 | 240 | 245 | 275 | 30 | 22.5 | 31 |
| | | | | 220 | 235 | 15 | | |
| | | 0.1 | | 250 | 280 | 30 | 27.5 | 24 |
| | | | | 220 | 245 | 25 | | |
| | | 0.05 | 300 | 250 | 260 | 10 | 15 | 54 |
| | | | | 220 | 240 | 20 | | |
| | | 0.1 | | 250 | 260 | 10 | 12.5 | 65 |
| | | | | 220 | 235 | 15 | | |
| SPONTANEOUSLY HYPERTENSIVE RATS n = 2 Body weight(s): 350, 350 grams | | | | | | | | |
| CONTROL | | 0.05 | 0 | 265 | 300 | 35 | 40 | |
| | | | | 240 | 285 | 45 | | |
| | | 0.1 | | 265 | 300 | 35 | 40 | |
| | | | | 245 | 290 | 45 | | |
| EX. NO. 73 | 0.3 i.v. | 0.05 | 30 | 255 | 265 | 10 | 12.5 | 69 |
| | | | | 240 | 255 | 15 | | |
| | | 0.1 | | 255 | 275 | 20 | 15 | 63 |
| | | | | 240 | 250 | 10 | | |
| | | 0.05 | 60 | 265 | 290 | 25 | 20 | 50 |
| | | | | 235 | 250 | 15 | | |
| | | 0.1 | | 260 | 290 | 30 | 27.5 | 31 |
| | | | | 240 | 265 | 25 | | |
| | | 0.05 | 90 | 260 | 285 | 25 | 20 | 50 |
| | | | | 235 | 250 | 15 | | |
| | | 0.1 | | 260 | 290 | 30 | 25 | 38 |
| | | | | 235 | 255 | 20 | | |
| | | 0.05 | 120 | 255 | 275 | 20 | 20 | 50 |
| | | | | 255 | 275 | 20 | | |
| | | 0.1 | | 255 | 295 | 40 | 30 | 25 |
| | | | | 250 | 277 | 20 | | |
| | | 0.05 | 180 | 255 | 290 | 35 | 29 | 28 |
| | | | | 242 | 265 | 23 | | |
| | | 0.1 | | 260 | 300 | 40 | 35 | 13 |
| | | | | 240 | 270 | 30 | | |
| | | 0.05 | 240 | 255 | 290 | 35 | 27.5 | 31 |
| | | | | 235 | 255 | 20 | | |
| | | 0.1 | | 250 | 270 | 20 | 19 | 53 |
| | | | | 237 | 255 | 18 | | |
| | | 0.05 | 300 | 260 | 285 | 25 | 20 | 50 |
| | | | | 235 | 250 | 15 | | |
| | | 0.1 | | 255 | 275 | 20 | 17.5 | 56 |
| | | | | 225 | 240 | 15 | | |
| SPONTANEOUSLY HYPERTENSIVE RATS n = 2 Body weight(s): 360, 385 grams | | | | | | | | |
| CONTROL | | 0.05 | 0 | 210 | 260 | 50 | 45 | |
| | | | | 195 | 235 | 40 | | |
| | | 0.1 | | 210 | 260 | 50 | 47.5 | |
| | | | | 210 | 255 | 45 | | |
| EX. NO. 73 | 1 i.v. | 0.05 | 30 | 190 | 200 | 10 | 7.5 | 83 |
| | | | | 190 | 195 | 5 | | |
| | | 0.1 | | 185 | 200 | 15 | 12.5 | 74 |
| | | | | 185 | 195 | 10 | | |
| | | 0.05 | 60 | 190 | 195 | 5 | 7.5 | 83 |
| | | | | 200 | 210 | 10 | | |
| | | 0.1 | | 200 | 215 | 15 | 16.5 | 65 |
| | | | | 190 | 208 | 18 | | |
| | | 0.05 | 90 | 190 | 195 | 5 | 7.5 | 83 |
| | | | | 180 | 190 | 10 | | |
| | | 0.1 | | 195 | 205 | 10 | 10 | 79 |
| | | | | 180 | 190 | 10 | | |
| | | 0.05 | 120 | 195 | 205 | 10 | 7.5 | 83 |
| | | | | 175 | 180 | 5 | | |
| | | 0.1 | | 195 | 198 | 3 | 6.5 | 86 |
| | | | | 175 | 185 | 10 | | |
| | | 0.05 | 180 | 210 | 220 | 10 | 12.5 | 72 |
| | | | | 200 | 215 | 15 | | |
| | | 0.1 | | 215 | 230 | 15 | 27.5 | 42 |
| | | | | 165 | 205 | 40 | | |
| | | 0.05 | 240 | 210 | 225 | 15 | 27.5 | 39 |
| | | | | 190 | 230 | 40 | | |
| | | 0.1 | | 205 | 220 | 15 | 12.5 | 74 |
| | | | | 205 | 215 | 10 | | |
| | | 0.05 | 300 | 195 | 210 | 15 | 22.5 | 50 |
| | | | | 195 | 225 | 30 | | |
| | | 0.1 | | 190 | 215 | 25 | 19 | 60 |
| | | | | 210 | 223 | 13 | | |

-continued

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| SPONTANEOUSLY HYPERTENSIVE RATS n = 2 Body weight(s): 360, 350 grams | | | | | | | | |
| CONTROL | | 0.05 | 0 | 245 | 275 | 30 | 40 | |
| | | | | 220 | 270 | 50 | | |
| | | | | 215 | 255 | 40 | | |
| | | 0.1 | | 240 | 280 | 40 | 41.7 | |
| | | | | 225 | 270 | 45 | | |
| | | | | 220 | 260 | 40 | | |
| EX. NO. 73 | 1 i.v. | 0.05 | 30 | 230 | 235 | 5 | 10 | 75 |
| | | | | 200 | 215 | 15 | | |
| | | | | 200 | 210 | 10 | | |
| | | 0.1 | | 235 | 245 | 10 | 133 | 68 |
| | | | | 200 | 210 | 10 | | |
| | | | | 185 | 205 | 20 | | |
| | | 0.05 | 60 | 230 | 235 | 5 | 6.7 | 83 |
| | | | | 215 | 220 | 5 | | |
| | | | | 205 | 215 | 10 | | |
| | | 0.1 | | 230 | 240 | 10 | 10 | 76 |
| | | | | 210 | 220 | 10 | | |
| | | | | 205 | 215 | 10 | | |
| | | 0.05 | 90 | 230 | 235 | 5 | 14.3 | 64 |
| | | | | 210 | 225 | 15 | | |
| | | | | 210 | 233 | 23 | | |
| | | 0.1 | | 230 | 242 | 12 | 12.3 | 76 |
| | | | | 220 | 230 | 10 | | |
| | | | | 205 | 220 | 15 | | |
| | | 0.05 | 120 | 240 | 255 | 15 | 9.3 | 77 |
| | | | | 210 | 215 | 5 | | |
| | | | | 190 | 198 | 8 | | |
| | | 0.1 | | 2340 | 235 | 5 | 13.3 | 68 |
| | | | | 210 | 225 | 15 | | |
| | | | | 200 | 220 | 20 | | |
| | | 0.05 | 180 | 225 | 230 | 5 | 16.7 | 58 |
| | | | | 210 | 225 | 15 | | |
| | | | | 190 | 220 | 30 | | |
| | | 0.1 | | 220 | 240 | 20 | 20.0 | 52 |
| SPONTANEOUSLY HYPERTENSIVE RATS n = 3 Body weight(s): 360, 355, 350 grams | | | | | | | | |
| | | | | 215 | 230 | 15 | | |
| | | | | 185 | 210 | 25 | | |
| CONTROL | | 0.05 | 0 | 245 | 275 | 30 | 40 | |
| | | | | 220 | 270 | 50 | | |
| | | | | 215 | 255 | 40 | | |
| | | 0.1 | | 240 | 280 | 40 | 41.7 | |
| | | | | 225 | 270 | 45 | | |
| | | | | 220 | 260 | 40 | | |
| EX. NO. 73 | 1 i.v. | 0.05 | 240 | 220 | 230 | 10 | 15.7 | 61 |
| | | | | 210 | 225 | 15 | | |
| | | | | 185 | 207 | 22 | | |
| | | 0.1 | | 225 | 240 | 15 | 16.7 | 60 |
| | | | | 220 | 240 | 20 | | |
| | | | | 195 | 210 | 15 | | |
| | | 0.05 | 300 | 230 | 240 | 10 | 25 | 38 |
| | | | | 210 | 240 | 30 | | |
| | | | | 175 | 210 | 35 | | |
| | | 0.1 | | 230 | 245 | 15 | 20 | 52 |
| | | | | 210 | 230 | 20 | | |
| | | | | 185 | 210 | 25 | | |
| SPONTANEOUSLY HYPERTENSIVE RATS n = 3 Body weight(s): 360, 355, 350 grams | | | | | | | | |
| CONTROL | | 0.05 | 0 | 235 | 255 | 20 | 25 | |
| | | | | 220 | 250 | 30 | | |
| | | 0.1 | | 240 | 260 | 20 | 27.5 | |
| | | | | 225 | 260 | 35 | | |
| 78 | 1 i.v. | 0.05 | 30 | 225 | 225 | 0 | 5 | 80 |
| | | | | 225 | 235 | 10 | | |
| | | 0.1 | | 230 | 240 | 10 | 15 | 45 |
| | | | | 215 | 235 | 20 | | |
| | | 0.05 | 60 | 220 | 230 | 10 | 12.5 | 50 |
| | | | | 210 | 225 | 15 | | |
| | | 0.1 | | 225 | 235 | 10 | 12.5 | 55 |
| | | | | 220 | 235 | 15 | | |
| | | 0.05 | 90 | 225 | 230 | 5 | 7.5 | 70 |
| | | | | 215 | 225 | 10 | | |
| | | 0.1 | | 225 | 240 | 15 | 15 | 45 |
| | | | | 220 | 235 | 15 | | |
| | | 0.05 | 120 | 215 | 225 | 10 | 10 | 60 |
| | | | | 220 | 230 | 10 | | |
| | | 0.1 | | 215 | 230 | 15 | 17.5 | 36 |
| | | | | 210 | 230 | 20 | | |

-continued

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| | | 0.05 | 180 | 215 | 225 | 10 | 11 | 56 |
| | | | | 218 | 230 | 12 | | |
| | | 0.1 | | 210 | 225 | 15 | 12.5 | 55 |
| | | | | 220 | 230 | 10 | | |
| | | 0.05 | 240 | 225 | 230 | 5 | 12.5 | 50 |
| | | | | 200 | 220 | 20 | | |
| | | 0.1 | | 220 | 20 | 10 | 12.5 | 55 |
| | | | | 210 | 225 | 15 | | |
| | | 0.05 | 300 | 220 | 225 | 5 | 5 | 80 |
| | | | | 210 | 215 | 5 | | |
| | | 0.1 | | 220 | 230 | 10 | 17.5 | 36 |
| | | | | 205 | 230 | 25 | | |
| SPONTANEOUSLY HYPERTENSIVE RATS n = 2 Body weight(s): 380, 400 grams | | | | | | | | |
| CONTROL | | 0.05 | 0 | 225 | 250 | 25 | 27.5 | |
| | | | | 225 | 255 | 30 | | |
| | | 0.1 | | 225 | 255 | 30 | 30 | |
| | | | | 225 | 255 | 30 | | |
| 78 | 3. p.o. | 0.05 | 30 | 210 | 240 | 30 | 27.5 | 0 |
| | | | | 215 | 240 | 25 | | |
| | | 0.1 | | 210 | 245 | 35 | 35 | −17 |
| | | | | 210 | 245 | 35 | | |
| | | 0.05 | 60 | 210 | 235 | 25 | 22.5 | 18 |
| | | | | 220 | 240 | 20 | | |
| | | 0.1 | | 220 | 240 | 30 | 25 | 17 |
| | | | | 220 | 240 | 20 | | |
| | | 0.05 | 90 | 210 | 235 | 25 | 22.5 | 18 |
| | | | | 220 | 240 | 20 | | |
| | | 0.1 | | 210 | 230 | 20 | 17.5 | 42 |
| | | | | 220 | 235 | 15 | | |
| | | 0.05 | 120 | 210 | 230 | 20 | 17.5 | 36 |
| | | | | 215 | 230 | 15 | | |
| | | 0.1 | | 195 | 215 | 20 | 15 | 50 |
| | | | | 225 | 235 | 10 | | |
| | | 0.05 | 180 | 210 | 233 | 23 | 19 | 31 |
| | | | | 215 | 23 | 15 | | |
| | | 0.1 | | 220 | 235 | 15 | 17.5 | 42 |
| | | | | 215 | 235 | 20 | | |
| | | 0.05 | 240 | 210 | 228 | 18 | 19 | 31 |
| | | | | 220 | 240 | 20 | | |
| | | 0.1 | | 220 | 235 | 15 | 17.5 | 42 |
| | | | | 220 | 240 | 20 | | |
| | | 0.05 | 300 | 220 | 240 | 20 | 27.5 | 0 |
| | | | | 205 | 240 | 35 | | |
| | | 0.1 | | 210 | 240 | 30 | 25 | 17 |
| | | | | 220 | 240 | 20 | | |
| SPONTANEOUSLY HYPERTENSIVE RATS n = 2 Body weight(s): 400, 390 grams | | | | | | | | |
| CONTROL | | 0.05 | 0 | 240 | 275 | 35 | 40 | |
| | | | | 230 | 275 | 45 | | |
| | | 0.1 | | 240 | 270 | 30 | 40 | |
| | | | | 230 | 280 | 50 | | |
| 80 | 1 p.o. | 0.05 | 30 | 240 | 265 | 25 | 30 | 25 |
| | | | | 225 | 260 | 35a | | |
| | | 0.1 | | 235 | 270 | 35 | 37.5 | 6 |
| | | | | 230 | 270 | 40 | | |
| | | 0.05 | 60 | 250 | 260 | 10 | 15 | 63 |
| | | | | 230 | 250 | 20 | | |
| | | 0.1 | | 240 | 270 | 30 | 32.5 | 19 |
| | | | | 225 | 260 | 35 | | |
| | | 0.05 | 90 | 235 | 260 | 25 | 22.5 | 44 |
| | | | | 230 | 250 | 20 | | |
| | | 0.1 | | 240 | 275 | 35 | 27.5 | 31 |
| | | | | 225 | 245 | 20 | | |
| | | 0.05 | 120 | 240 | 255 | 15 | 10 | 75 |
| | | | | 215 | 220 | 5 | | |
| | | 0.1 | | 245 | 270 | 25 | 22.5 | 44 |
| | | | | 215 | 235 | 20 | | |
| | | 0.05 | 180 | 235 | 260 | 25 | 19 | 53 |
| | | | | 210 | 223 | 13 | | |
| | | 0.1 | | 240 | 270 | 30 | 25 | 38 |
| | | | | 210 | 230 | 20 | | |
| | | 0.05 | 240 | 230 | 250 | 20 | 17.5 | 56 |
| | | | | 210 | 225 | 15 | | |
| | | 0.1 | | 235 | 270 | 35 | 25 | 38 |
| | | | | 220 | 235 | 15 | | |
| | | 0.05 | 300 | 200 | 245 | 45 | 30 | 25 |
| | | | | 205 | 220 | 15 | | |
| | | 0.1 | | 240 | 270 | 30 | 27.5 | 31 |
| | | | | 210 | 235 | 25 | | |

-continued

| | | ANGIOTENSIN II (AII) VASOPRESSOR RESPONSE | | | | | | |
|---|---|---|---|---|---|---|---|---|
| Example No. | Dose (mg/kg) | AII Dose mcg/kg IV | Min Post Dose | Control Before AII | Response After AII | Change | Average Change | % Inhibition |
| SPONTANEOUSLY HYPERTENSIVE RATS n = 2 Body weight(s): 390, 370 grams | | | | | | | | |
| CONTROL | | 0.05 | 0 | 240 | 290 | 50 | 52.5 | |
| | | | | 235 | 290 | 55 | | |
| | | 0.1 | | 245 | 290 | 45 | 50 | |
| | | | | 240 | 295 | 55 | | |
| 80 | 1 i.v. | 0.05 | 30 | 250 | 255 | 5 | 5 | 90 |
| | | | | 240 | 245 | 5 | | |
| | | 0.1 | | 245 | 252 | 7 | 8.5 | 83 |
| | | | | 240 | 250 | 10 | | |
| | | 0.05 | 60 | 250 | 255 | 5 | 5 | 90 |
| | | | | 230 | 235 | 5 | | |
| | | 0.1 | | 250 | 265 | 15 | 10 | 80 |
| | | | | 235 | 240 | 5 | | |
| | | 0.05 | 90 | 242 | 250 | 8 | 9 | 83 |
| | | | | 235 | 245 | 10 | | |
| | | 0.1 | | 235 | 255 | 20 | 22.5 | 55 |
| | | | | 235 | 260 | 25 | | |
| | | 0.05 | 120 | 230 | 250 | 20 | 12.5 | 76 |
| | | | | 230 | 235 | 5 | | |
| | | 0.1 | | 235 | 255 | 20 | 17.5 | 65 |
| | | | | 230 | 245 | 15 | | |
| | | 0.05 | 180 | 225 | 245 | 20 | 12.5 | 76 |
| | | | | 235 | 240 | 5 | | |
| | | 0.1 | | 225 | 250 | 25 | 17.5 | 65 |
| | | | | 235 | 245 | 10 | | |
| | | 0.05 | 240 | 235 | 250 | 15 | 20 | 62 |
| | | | | 210 | 235 | 25 | | |
| | | 0.1 | | 230 | 255 | 25 | 22.5 | 55 |
| | | | | 220 | 240 | 20 | | |
| | | 0.05 | 300 | 225 | 240 | 15 | 16.5 | 69 |
| | | | | 210 | 228 | 18 | | |
| | | 0.1 | | 225 | 260 | 35 | 30 | 40 |
| | | | | 215 | 240 | 25 | | |
| SPONTANEOUSLY HYPERTENSIVE RATS n = 2 Body weight(s): 400, 400 grams | | | | | | | | |

Figure 2:
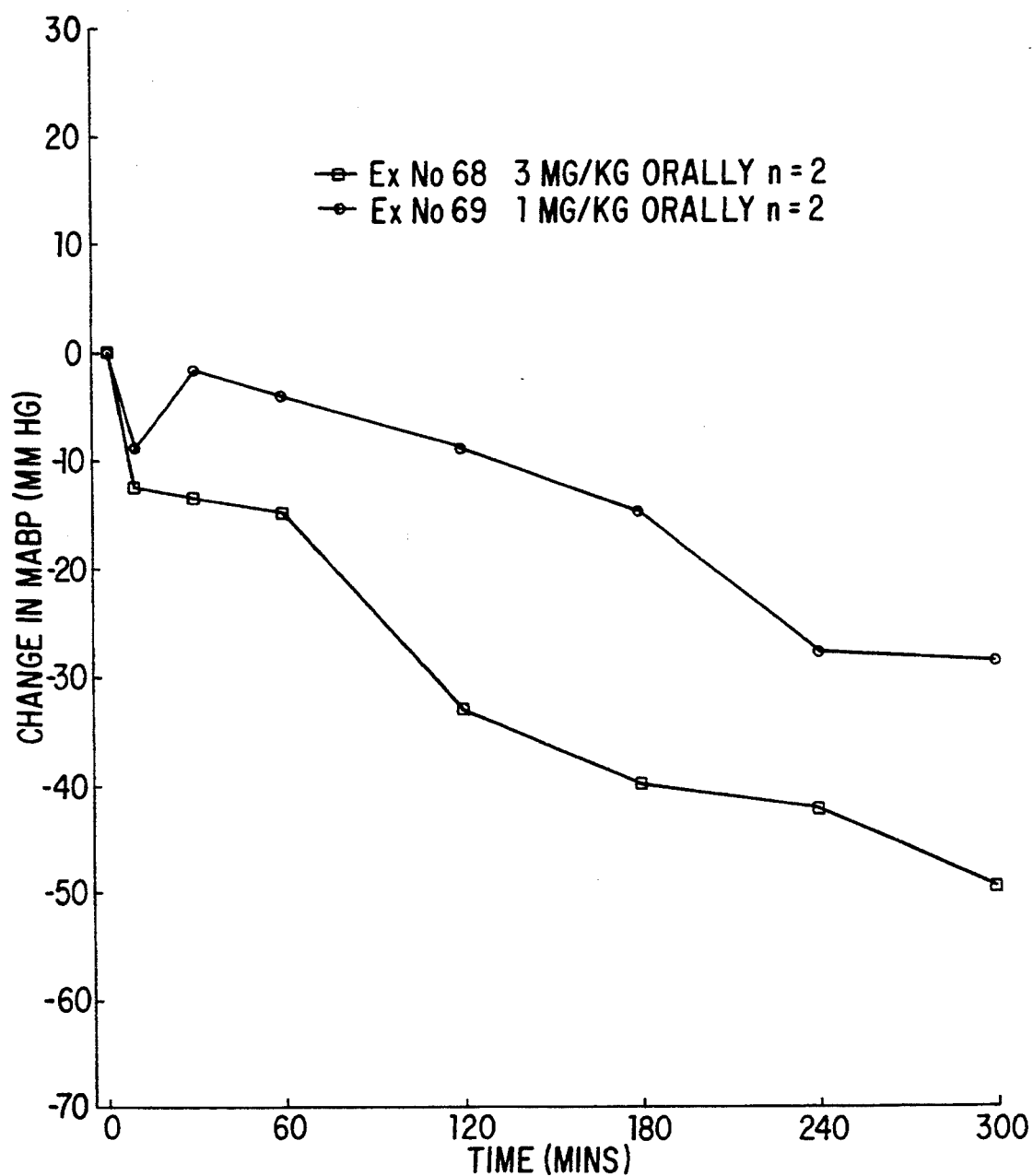
Figure 3:
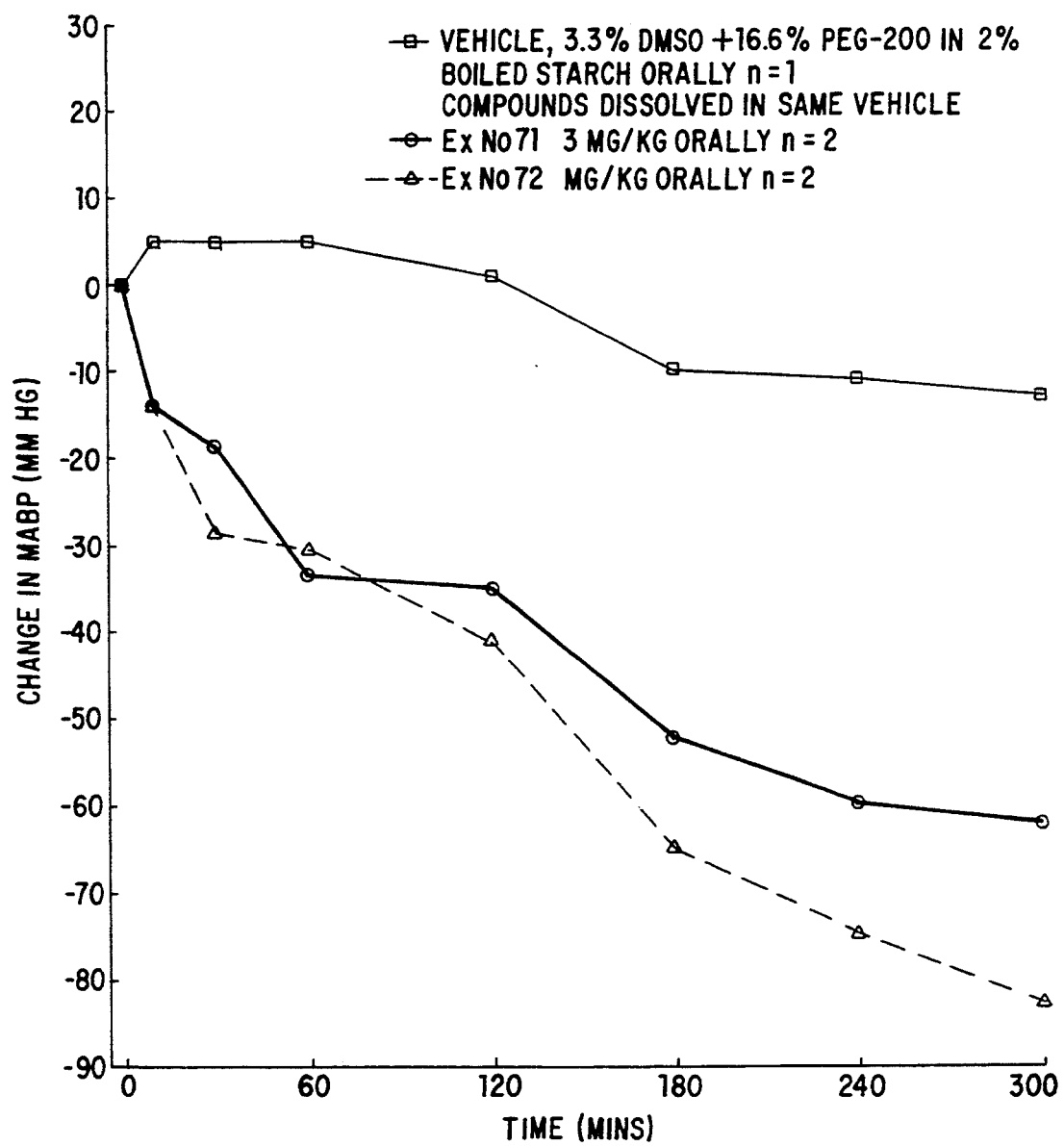
Figure 4:
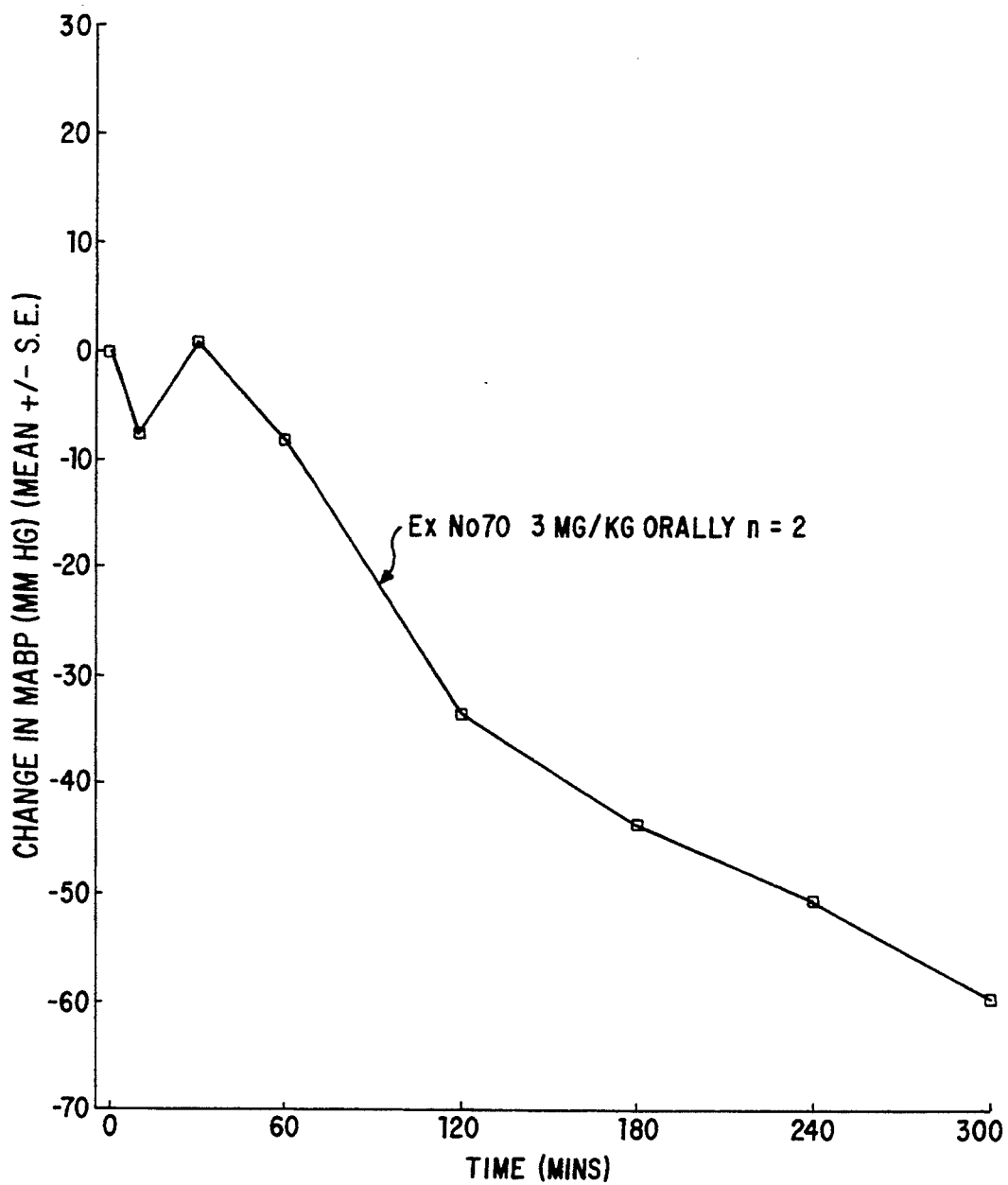
Figure 5:
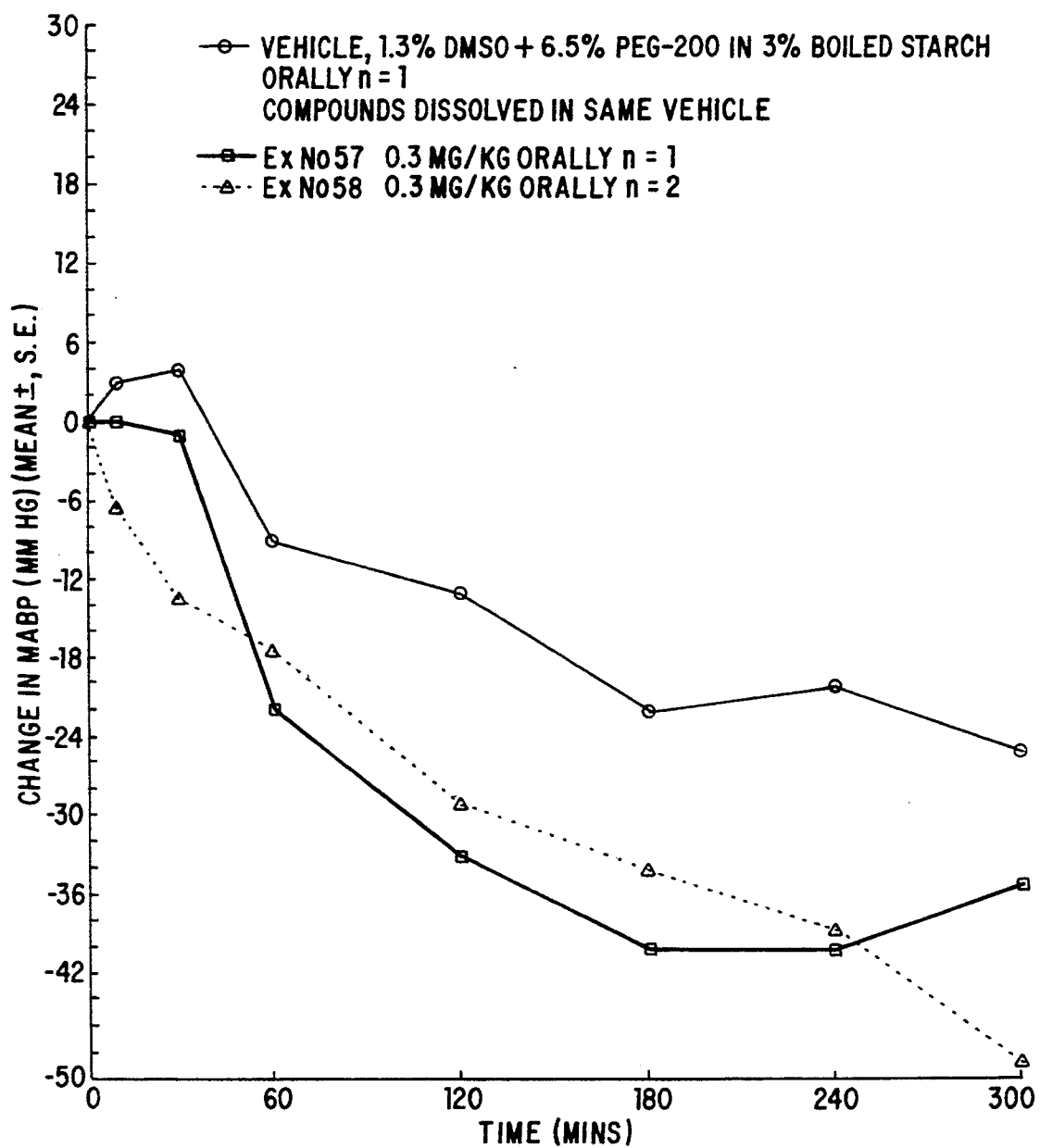
Figure 6:
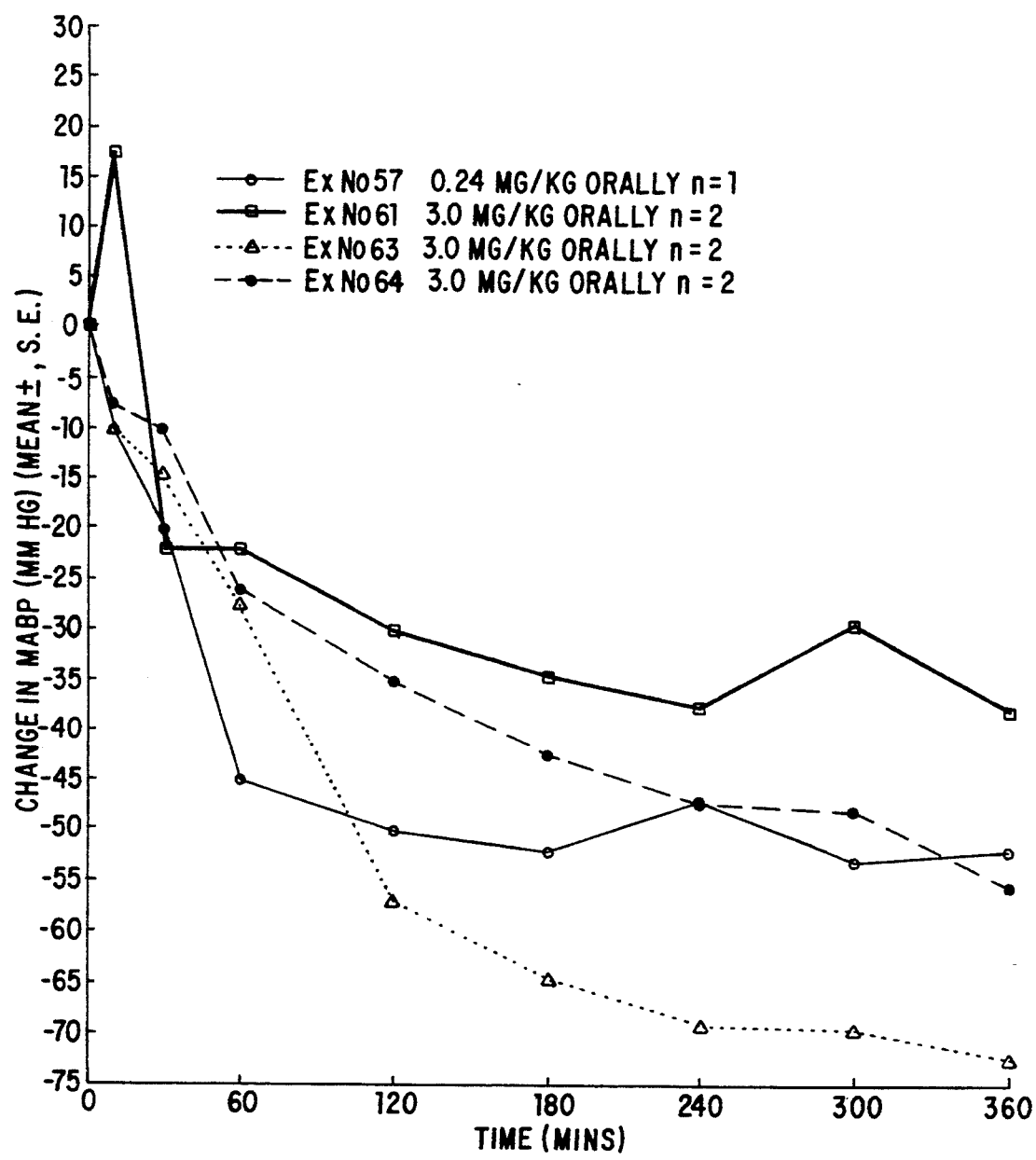
Figure 7:
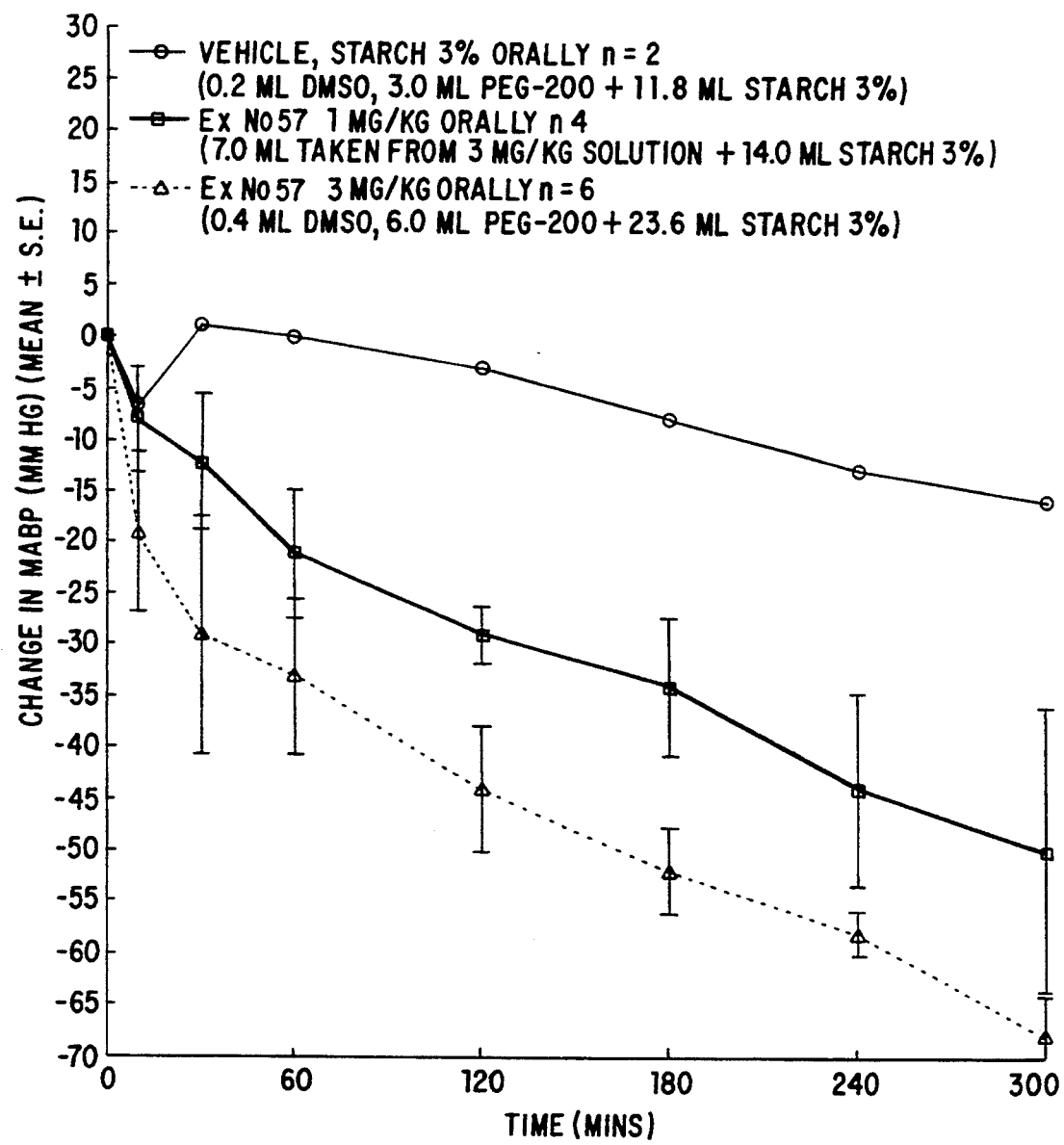
Figure 8:
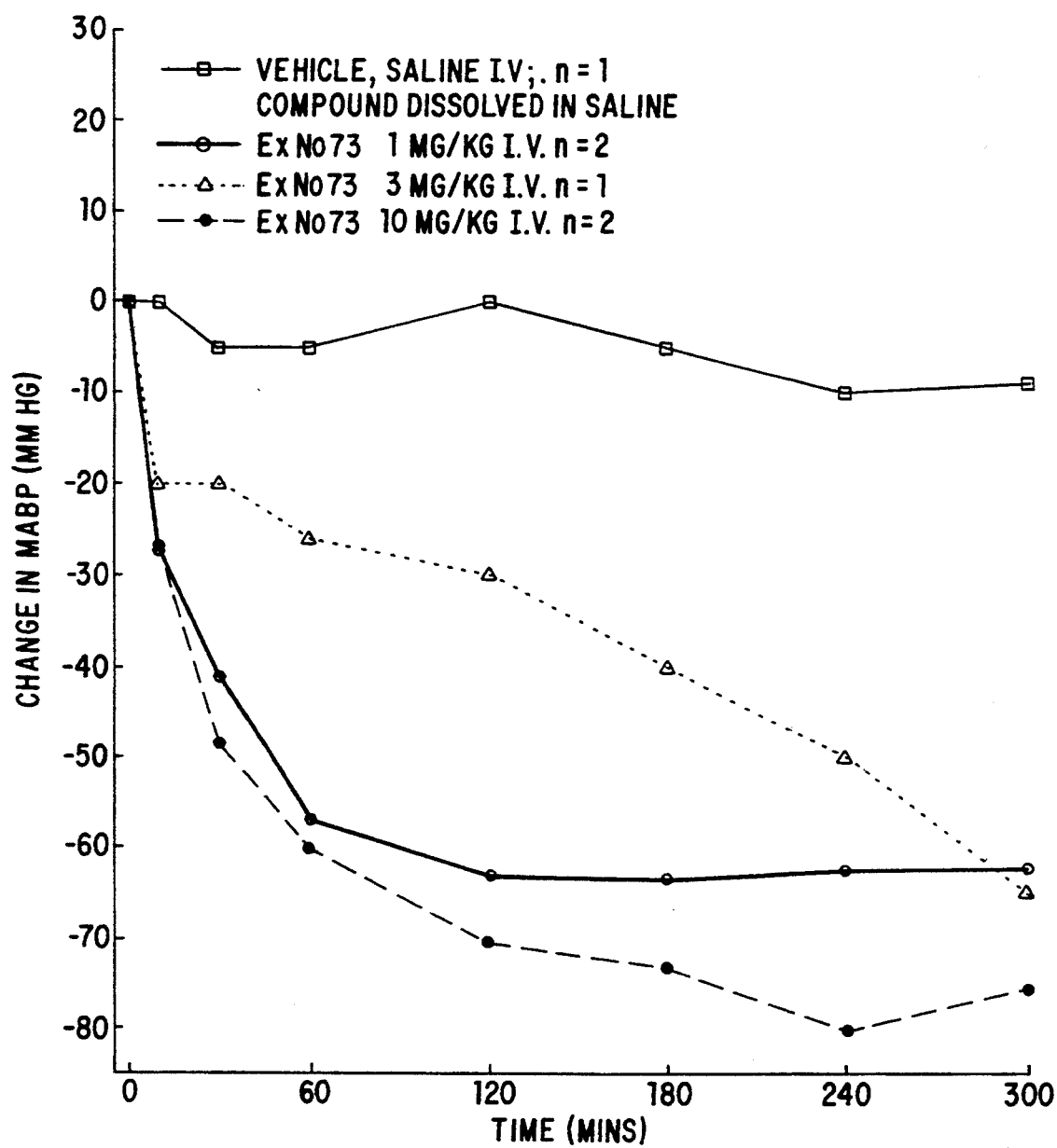
Figure 9:
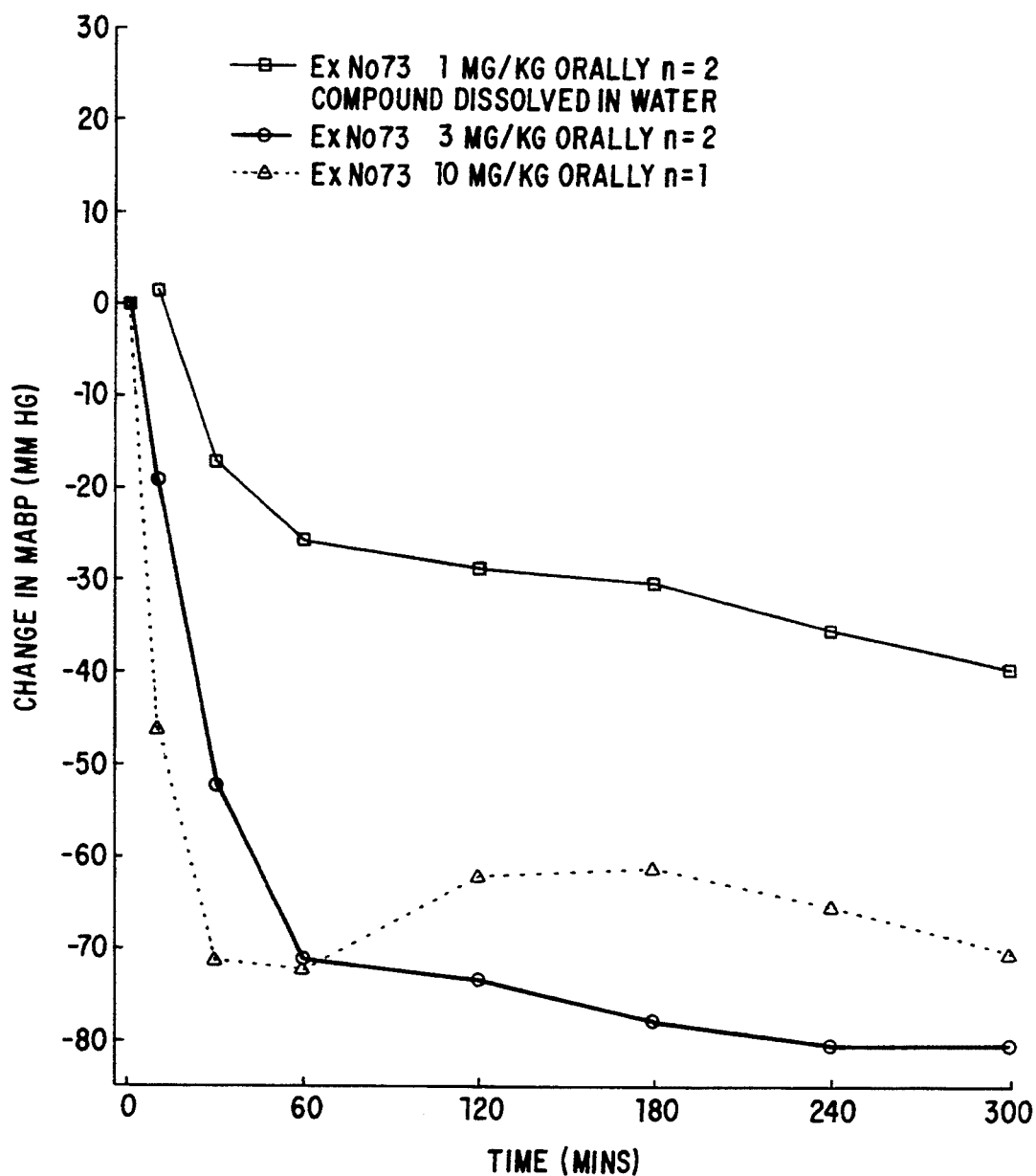

Antiphypertenesive Effects in Conscious Aorta-Coarcted Renin/Angiotensin II-Dependent Renal Hypertensive Rats Following the method reported by Chan et al., Drug Development Res. 18: 75-94, 1989, hypertension is induced by complete ligation of the aorta between the origin of the renal arteries according to the method of Rojo-Ortega and Genest (Can. J. Physio Pharmacol 46: 883-885, 1968.) and Fernandes et al., (J. Lab. Clin. Med. 87: 561-567, 1976) with modifications of the surgery procedures. Male Sprague-Dawley rats (Charles River Labs., Inc., Wilmington, Mass.) of 350 to 400 gm body weight are anesthetized with methohexital sodium (Brevital sodium, Eli Lilly and Co.) 60 mg/kg i.p. An incision is made in the left flank parallel to the rib cage. Using No. 3-0 silk suture (Davis & Geck, Pearl River, N.Y.), the aorta is completely ligated between the origins of the renal arteries. The wound is closed, and the animals returned to their individual cages. On the 7th day after aortic coarctation, the rats are used. The rats are restrained in a supine position with elastic tape, and the heads are immobilized by gentel restraining. The ventral portion of the neck is locally anesthetized by subcutaneous infiltration with 2% lidocaine. The left carotid artery is isolated and cannulated with a length of PE50 tubing, which is in turn, connected to a Statham $P_{23}Db$ pressure transducer-Beckman Dynagraph recording system. In some studies, the cannular is exteriorized through the back of the neck for long period of blood pressure monitoring. Recordings are taken over a 15-20 minutes period, and the rats are dosed with the test compounds or vehicle (saline). After dosing, the blood pressure is monitored continuously. The results are shown in FIG. 1 to 9.

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

What is claimed is:

1. A quinazolinone compound having the formula:

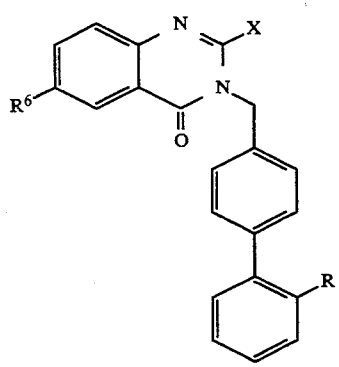

FORMULA I wherein:
R is

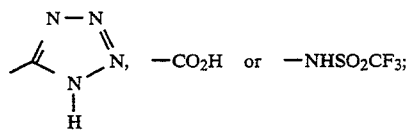

X is lower alkyl of 3 to 5 carbon atoms;
$R^6$ is:

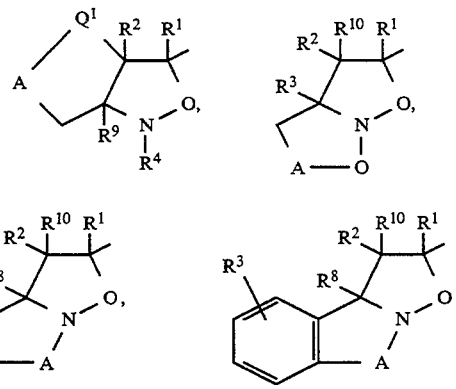

$R^1$ is H, lower alkyl of 1 to 4 carbon atoms (optionally substituted with —$OR^7$, —$CO_2R^7$, —CN, —$N(R^7)(R^{13})$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —$OR^7$, —$CO_2R^7$, —CN, —$CON(R^7)(R^{13})$, —$CF_3$, —SPh, —$N(R^7)(R^{13})$ or

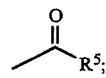

$R^2$ is H, lower alkyl of 1 to 4 carbon atoms (optionally substituted with —$OR^7$, —$CO_2R^7$, —CN, —$N(R^7)(R^{13})$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —$CO_2R^7$, —CN, —$CON(R^7)(R^{13})$, or

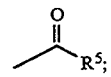

$R^3$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene or furan, —$CO_2R^7$, —$CON(R^7)(R^{13})$, —CN, —$NO_2$, or

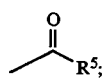

$R^4$ is H, —CO$_2$R$^7$, —SO$_2$R$^{12}$, lower alkyl of 1 to 4 carbon atoms, benzyl, substituted benzyl (substitution selected from mono-lower alkyl of 1 to 3 carbon atoms, trifluoromethyl, nitro, O-alkyl of 1 to 3 carbon atoms, F, Cl, or Br) phenyl, substituted phenyl (substitution selected from mono-lower alkyl of 1 to 3 carbon atoms, trifluoromethyl, nitro, O-alkyl of 1 to 3 carbon atoms, F, Cl, or Br), —CON(R$^7$)(R$^{13}$), or

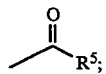

$R^{12}$ is phenyl, substituted phenyl (substitution selected from mono-lower alkyl of 1 to 3 carbon atoms, trifluoromethyl, nitro, O-alkyl of 1 to 3 carbon atoms, F, Cl, or Br);
$R^5$ is H, lower alkyl of 1 to 4 carbon atoms;
$R^7$ is H, lower alkyl of 1 to 4 carbon atoms;
$R^8$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), —CO$_2$R$^7$, —CH$_2$OH, —CN, —CON(R$^7$)(R$^{13}$), or

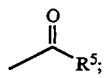

$R^9$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br);
$R^{10}$ is H, lower alkyl of 1 to 4 carbon atoms (optionally substituted with —OR$^7$, —CO$_2$R$^7$, —CN, —N(R$^7$)(R$^{13}$), phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —OR$^7$, —CO$_2$R$^7$, —CN, —CON(R$^7$)(R$^{13}$), —CF$_3$, or

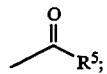

$R^{13}$ is H, lower alkyl of 1 to 4 carbon atoms;
Q is —O—, —(CR$^{11}$R$^{14}$)$_n$— or a single bond;
Q$^1$ is —O—, —(CR$^{11}$R$^{14}$)$_n$—,

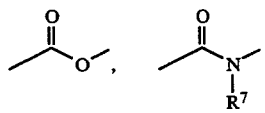

or a single bond;

n is 1 to 5;
A is —(CR$^{11}$R$^{14}$)$_m$—;
m is 2 to 5, provided that n+m is not greater than 6;
$R^{11}$ is H, lower alkyl of 1 to 4 carbon atoms (optionally substituted with —OR$^7$, —CO$_2$R$^7$, —CN, —N(R$^7$)(R$^{13}$), phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —OR$^7$, —CO$_2$R$^7$, —CN, —CON(R$^7$)(R$^{13}$), —CF$_3$, or

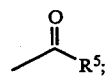

$R^{14}$ is H, lower alkyl of 1 to 4 carbon atoms (optionally substituted with —OR$^7$, —CO$_2$R$^7$, —CN, —N(R$^7$)(R$^{13}$), phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —OR$^7$, —CO$_2$R$^7$, —CN, —CON(R$^7$)(R$^{13}$), —CF$_3$, or

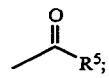

and pharmaceutically acceptable salts thereof.

2. The compound according to claim 1 wherein said salts are selected from potassium, sodium, calcium, magnesium or ammonium.

3. The compound according to claim 1 wherein R is

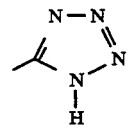

X is straight chain alkyl of 4 carbon atoms;
$R^6$ is:

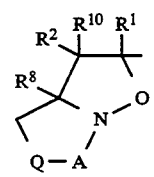

Q is a single bond and m is 2 or 3.

4. The compound according to claim 1 wherein:
R is

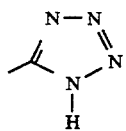

X is straight chain alkyl of 4 carbon atoms
R⁶ is

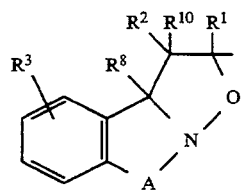

m is 2.
5. The compound according to claim 1 wherein:
R is

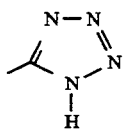

X is straight chain alkyl of 4 carbon atoms
R⁶ is

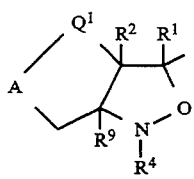

Q¹ is a single bond and
m is 2or 3.
6. The compound according to claim 1 wherein:
R is

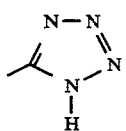

X is straight chain alkyl of 4 carbon atoms
R⁶ is:

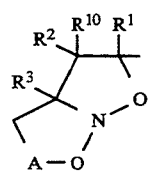

and m is 2.
7. The compound according to claim 1 wherein
X is a straight chain alkyl of 3 or 4 carbon atoms;
R⁶ is

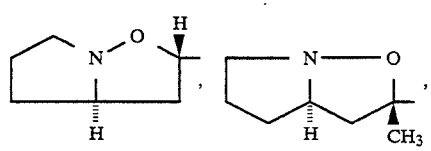

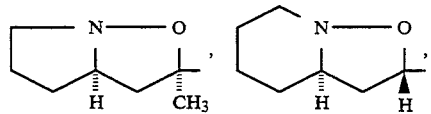

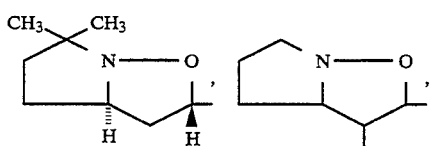

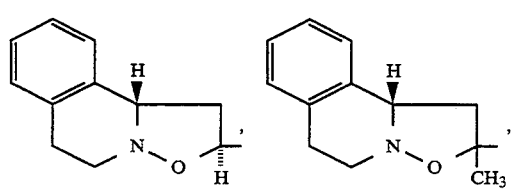

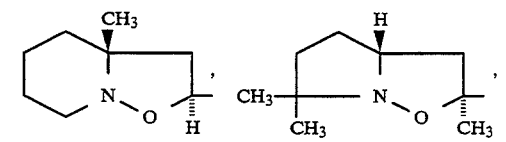

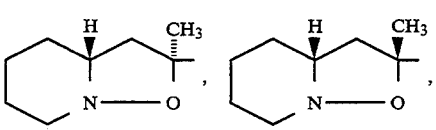

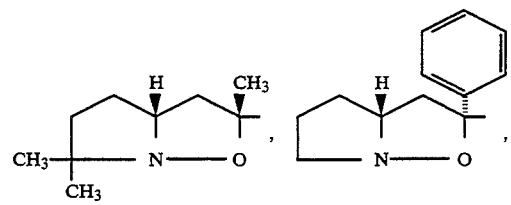

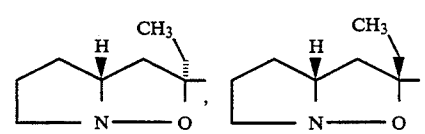

8. A quinazolinone compound having the formula:

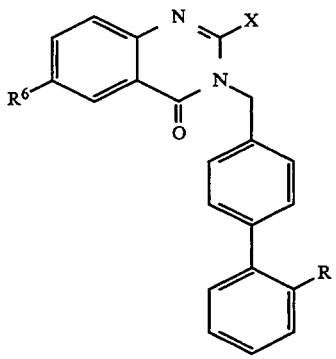

wherein:
R is

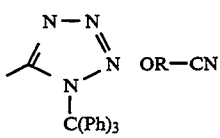 OR—CN

X is lower alkyl of 3 to 5 carbon atoms;
R⁶ is:

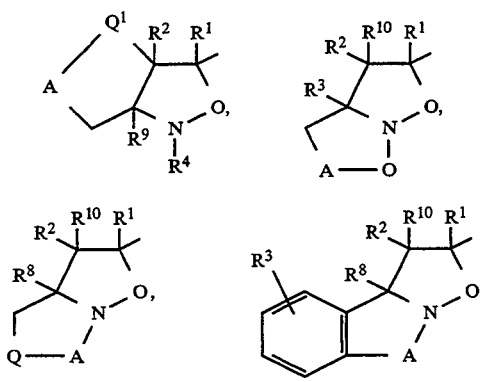

R¹, is H, lower alkyl of 1 to 4 carbon atoms (optionally substituted with —OR⁷, —CO₂R⁷, —CN, —N(R⁷)(R¹³), phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —OR⁷, —CO₂R⁷, —CN, —CON(R⁷)(R¹³), —CF₃, —SPh —N(R⁷)(R¹³), or

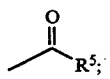

R², is H, lower alkyl of 1 to 4 carbon atoms (optionally substituted with —OR⁷, —CO₂R⁷, —CN, —N(R⁷)(R¹³), phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —CO₂R⁷, —CN, —CON(R⁷)(R¹³), or

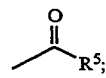

R³ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br) pyridine, thiophene or furan, —CO₂R⁷, —CON(R⁷)(R¹³), —CN, —NO₂, or

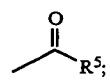

R⁴ is H, —CO₂R⁷, —SO₂R¹², lower alkyl of 1 to 4 carbon atoms, benzyl, substituted benzyl (substitution selected from mono-lower alkyl of 1 to 3 carbon atoms, trifluoromethyl, nitro, O-alkyl of 1 to 3 carbon atoms, F, Cl, or Br) phenyl, substituted phenyl (substitution selected from mono-lower alkyl of 1 to 3 carbon atoms, trifluoromethyl, nitro, O-alkyl of 1 to 3 carbon atoms, F, Cl, or Br), —CON(R⁷)(R¹³), or

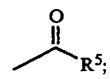

R¹² is phenyl, substituted phenyl (substitution selected from mono-lower alkyl of 1 to 3 carbon atoms, trifluoromethyl, nitro, O-alkyl of 1 to 3 carbon atoms, F, Cl, or Br);
R⁵ is H, lower alkyl of 1 to 4 carbon atoms;
R⁷, is H, lower alkyl of 1 to 4 carbon atoms;
R⁸ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), —CO₂R⁷, —CH₂OH, —CN, —CON(R⁷)(R¹³), or

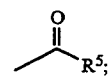

R⁹ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br);
R¹⁰ is H, lower alkyl of 1 to 4 carbon atoms (optionally substituted with —OR⁷, —CO₂R⁷, —CN, —N(R⁷)(R¹³), phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —OR⁷, —CO₂R⁷, —CN, —CON(R⁷)(R¹³), —CF₃, or

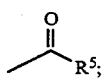

$R^{13}$ is H, lower alkyl of 1 to 4 carbon atoms;
Q is —O—, —(CR$^{11}$R$^{14}$)$_n$— or a single bond;
Q$^1$ is—O—, —(CR$^{11}$R$^{14}$)$_n$—,

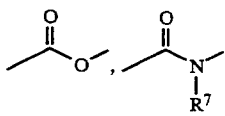

or a single bond;
n is 1 to 5;
A is —(CR$^{11}$R$^{14}$)$_m$—;
m is 2 to 5, provided that n+m is not greater than 6;
R$^{11}$ is H, lower alkyl of 1 to 4 carbon atoms (optionally substituted with —OR$^7$, —CO$_2$R$^7$, —CN, —N(R$^7$)(R$^{13}$), phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —OR$^7$, —CO$_2$R$^7$, —CN, —CON(R$^7$)(R$^{13}$), —CF$_3$, or

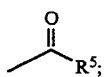

R$^{14}$ is H, lower alkyl of 1 to 4 carbon atoms (optionally substituted with —OR$^7$, —CO$_2$R$^7$, —CN, —N(R$^7$) (R$_{13}$), phenyl, substituted phenyl (substitution selected from mono-lower alkyl of 1 to 3 carbon atoms, trifluoromethyl, nitro, O-alkyl of 1 to 3 carbon atoms, F, Cl, or Br)), phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, —OR$^7$, —CO$_2$R$^7$, —CN, —CON(R$^7$)(R$^{13}$), —CF$_3$, or

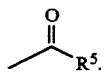

9. The compound according to claim 8 wherein X is a straight chain alkyl of 3 or 4 carbon atoms; R$^6$ is

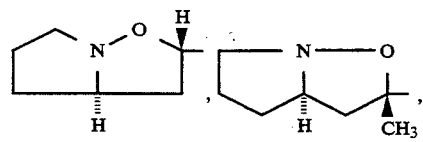

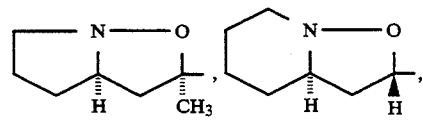

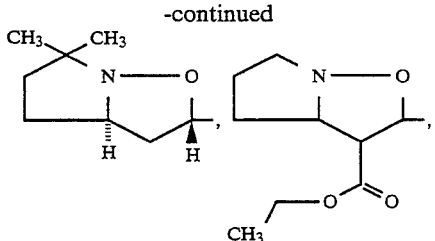

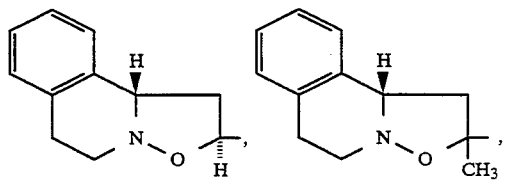

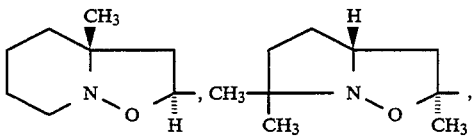

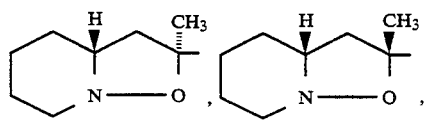

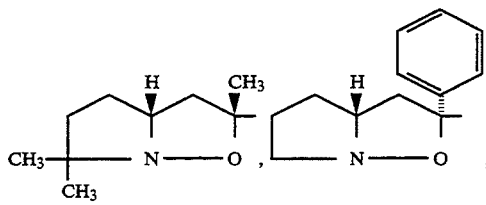

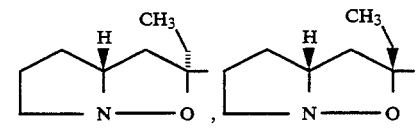

10. A method of antagonizing the effects of Angiotensin II in a mammal comprising administering a compound of claim 1 to said mammal in an amount effective to treat the effects of Angiotensin II.

11. The compound according to claim 1 Cis-(+/—)-2-Butyl-6-(hexahydropyrrolo[1,2-b]isoxazol-2-yl)-3-[[2''-(1H-tetrazol-5-yl)[1,1'-biphenyl]-4-yl]methyl]-4(3H)-quinazolinone.

12. The compound according to claim 1 Cis-(+/—)-2-Butyl-6-(hexahydro-2-methylpyrrolo[1,2-b]isoxazol-2-yl)-3-[[2'-(1H-tetrazol-5-yl)[1,1'-biphenyl]-4-yl]methyl]-4(3H)-quinazolinone.

13. The compound according to claim 1, (2S-CIS)-2-Butyl-6-(hexahydro-2-methylpyrrolo[1,2-b]isoxazol-2-yl)-3-[[2'-(1H-tetrazol-5-yl)[1,1'-biphenyl]-4-yl]methyl]-4(3H)-quinazolinone.

14. The compound according to claim 1, (2R-CIS)-2-Butyl-6-(hexahydro-2-methylpyrrolo[1,2b]isoxazol2-yl)-3-[[2'-(1H-tetrazol-5-yl)[1,1'-biphenyl]-4-yl]methyl]-4(3H)-quinazolinone.

15. The compound according to claim 1 (Trans)-2-Butyl-6-(hexahydro-2-methylpyrrolo[1,2-b]isoxazol-2-yl)-3-[[2'-(1H-tetrazol-5-yl)[1,1'-biphenyl]-4-yl]methyl]-4(3H)-quinazolinone.

16. The compound according to claim 1 (Cis)-2-Butyl-6-(hexahydro-2H-isoxazolo[2,3-a]pyridin-2-yl)-3-[[2'-(1H-tetrazol-5-yl)-[1,1'-biphenyl]-4-yl]methyl]-4(3H)-quinazolinone.

17. The compound according to claim 1 (Cis)-2-Butyl-6-(hexahydro-6,6-dimethylpyrrolo-[1,2-b]isoxazol-2-yl)-3-[[2'-(1H-tetrazol-5-yl)[1,1'-biphenyl]-4-yl]methyl]-4(3H)-quinazolinone.

18. The compound according to claim 1 Ethyl 2-[2-butyl-3,4-dihydro-4-oxo-3-[[2'-(1H-tetrazol-5-yl)[1,1'-biphenyl]-4-yl]methyl]-6-quinazolinyl]hexahydro-pyrrolo[1,2-b]isoxazole-3-carboxylate.

19. The compound according to claim 1 (Cis)-2-Butyl-6-(1,5,6,10b-tetrahydro-2H-isoxazolo-[3,2-a]isoquinolin-2-yl)-3-[[2'-(1H-tetrazol-5-yl)[1,1'-biphenyl]-4-yl]methyl]-4(3H)-quinazolinone.

20. The compound according to claim 1 (Cis)-2-Butyl-6-(1,5,6,10b-tetrahydro-2-methyl-2H-isoxazolo[3,2-a]isoquinolin-2-yl)-3-[[2'-(1H-tetrazol-5-yl)[1,1'-biphenyl]-4-yl]methyl]-4(3H)-quinazolinone.

21. The compound according to claim 1 (trans)-2-Butyl-6-(1,5,6,10b-tetrahydro-2-methyl-2H-isoxazolo[3,2-a]isoquinolin-2-yl)-3-[[2'-(1H-tetrazol-5-yl)[1,1'-biphenyl]-4-yl]methyl]-4(3H)-quinazolinone.

22. The compound according to claim 1 2-Butyl-6-(hexahydro-3a-methyl)-2H-isoxazolo[2,3-a]pyridin-3-yl)-3-[[2'-(1H-tetrazol-5-yl)[1,1'-biphenyl]-4-yl]methyl]-4(3H)-quinazolinone.

23. The compound according to claim 1 (Cis)-2-Butyl-6-(hexahydro-2,6,6-trimethylpyrrolo[1,2-b]isoxazol-2-yl)-3-[[2'-(1H-tetrazol-5-yl)[1,1'-biphenyl]-4-yl]methyl]-4(3H)-quinazolinone.

24. The compound according to claim 1 (Cis)-2-Butyl-6-(hexahydro-2-methyl-2H-isoxazolo[2,3-a]pyridin-2-yl)-3-[[2'-(1H-tetrazol-5-yl)[1,1'-biphenyl]-4-yl]methyl]-4(3H)-quinazolinone.

25. The compound according to claim 1 (Trans)-2-Butyl-6-(hexahydro-2-methyl-2H-isoxazolo[2,3-a]pyridin-2-yl)-3-[[2'-(1H-tetrazol-5-yl)[1,1'-biphenyl]-4-yl]methyl]-4(3H)-quinazolinone.

26. The compound according to claim 1 (Trans)-2-Butyl-6-(hexahydro-2,6,6-trimethylpyrrolo[1,2-b]isoxazol-2-yl)-3-[[2'-(1H-tetrazol-5-yl)[1,1'-biphenyl]-4-yl]methyl]-4(3H)-quinazolinone.

27. The compound according to claim 1 (Cis)-2-butyl-6-(hexahydro-2-phenylpyrrolo[1,2-b]isoxazol-2-yl)-3-[[2'-(1H-tetrazol-5-yl)[1,1'-biphenyl]-4-yl]methyl]-4(3H)-quinazolinone.

28. The compound according to claim 1 (Cis)-2-butyl-6-(2-ethylhexahydropyrrolo[1,2-b]isoxazol-2-yl)-3-[[2'-[1-(triphenylmethyl)-1H-tetrazol-5yl][1,1'-biphenyl]-4-yl]methyl]-4(3H)-quinazolinone.

29. The compound according to claim 1 (Trans)-2-butyl-6-(2-ethylhexahydropyrrolo[1,2-b]isoxazol-2-yl)-3-[[2'-(1H-tetrazol-5-yl)[1,1'-biphenyl]-4-yl]methyl]-4(3H)-quinazolinone.

30. The compound according to claim 1, (Cis)-2-butyl-6-(hexahydro-2-methylpyrrolo[1,2-b]isoxazol-2-yl)-3-[[2'-(1H-tetrazol-5-yl)[1,1'-biphenyl]-4-yl]methyl]-4(3H)-quinazolinone, sodium salt.

31. The compound according to claim 1, (2S-cis)-2-butyl-6-(hexahydro-2-methylpyrrolo[1,2-b]isoxazol-2-yl)-3-[[2'-(1H-tetrazol-5-yl)[1,1'-biphenyl]-4-yl]methyl]-4(3H)-quinazolinone, sodium salt.

32. The compound according to claim 1, (2R-cis)-2-butyl-6-(hexahydro-2-methylpyrrolo[1,2-b]isoxazol-2-yl)-3-[[2'-(1H-tetrazol-5-yl)[1,1'-biphenyl]-4-yl]methyl]-4(3H)-quinazolinone, sodium salt.

33. The compound according to claim 1, (Trans)-2-butyl-6-(hexahydro-2-methylpyrrolo[1,2-b]isoxazol2-yl)-3-[[2'-(1H-tetrazol-5-yl)[1,1'-biphenyl]-4-yl]methyl]-4(3H)-quinazolinone, sodium salt.

34. The compound according to claim 8 Cis-(+/−)-2-Butyl-6-(hexahydropyrrolo[1,2-b]isoxazol-2-2-yl)-3-[[2'-[1-(triphenylmethyl)-1H-tetrazol-5-yl][1,1'biphenyl]-4-yl]methyl]-4(3H)-quinazolinone.

35. The compound according to claim 8 Cis-(+/−)-2-Butyl-6-(hexahydro-2-methylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone.

36. The compound according to claim 8 (2S-cis)-2-Butyl-6-(hexahydro-2-methylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone.

37. The compound according to claim 8 (2R-cis)-2-Butyl-6-(hexahydro-2-methylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone.

38. The compound according to claim 8 trans-2-butyl-6-(hexahydro-2-methylpyrrolo[1,2-b]isoxazol-2-yl)3-[[2'-[1-(triphenylmethyl)-1H-tetrazol-5-yl][1,1'-biphenyl]-4-yl]-methyl]-4-(3H)-quinazolinone.

39. The compound according to claim 8 (cis)-2-Butyl-6-(hexahydro-2H-isoxazolo[2,3-a]-pyridin-2-yl)-3-[[2'-[1-(triphenylmethyl)-1H-tetrazol-5-yl][1,1'-biphenyl]-4-yl]methyl]-4(3H)-quinazolinone.

40. The compound according to claim 8 trans2-Butyl-6-(hexahydro-2H-isoxazolo[2,3-a]-pyridin-2-yl)-3-[[2'-[1-(triphenylmethyl)-1H-tetrazol-5-yl][1,1'-biphenyl]-4-yl]methyl]-4(3H)-quinazolinone.

41. The compound according to claim 8 cis-2-Butyl-6-(hexahydro-6,6-dimethylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone.

42. The compound according to claim 8 Ethyl 2-[2-butyl-3,4-dihydro-4-oxo-3-[[2'-[1-(triphenylmethyl)-1H-tetrazol-5-yl][1,1'-biphenyl]-4-yl]methyl]-6-quinazolinyl]hexahydro-pyrrolo[1,2-b]isoxazole-3-carboxylate.

43. The compound according to claim 8 Cis-2-Butyl-6-(1,5,6,10b-tetrahydro-2H-isoxazolo[3,2-a]isoquinolin-2-yl)-3-[[2'-[1-(triphenylmethyl)-1H-tetrazol-5-yl][1,1'-biphenyl]-4-yl]methyl]-4(3H)-quinazolinone.

44. The compound according to claim 8 Cis-2-Butyl-6-(1,5,6,10b-tetrahydro-2-methyl-2H-isoxazolo[3,2-a]isoquinolin-2-yl)-3-[[2'-[1-(triphenylmethyl)-1H-tetrazol-5-yl][1,1'-biphenyl]-4-yl]methyl]-4(3H-quinazolinone.

45. The compound according to claim 8 trans -2-Butyl-6-(1,5,6,10b-tetrahydro-2-methyl-2H-isoxazolo[3,2-a]isoquinolin-2-yl)-3-[[2'-[1-(triphenylmethyl)-1-H-tetrazol-5-yl][1,1'-biphenyl]-4-yl]methyl]-4(3H-quinazolinone.

46. The compound according to claim 8 Cis -2-butyl-6-(hexahydro-3a-methyl-2H-isoxazolo[2,3-a]pyridin-2-yl)-3-[[2'-[1-(triphenylmethyl)-1H-tetrazol-s-yl][1,1'-biphenyl]-4-yl]methyl-4-(3H)-quinazolinone.

47. The compound according to claim 8 Cis(+/−)-2-Butyl-6-(hexahydro-2,6,6-trimethylpyrrolo[1,2-b]isoxazol-2-yl)-3-[[2'-[1-(triphenylmethyl)-1H-tetrazol-5-yl][1,1'-biphenyl]-4-yl]methyl]-4(3H)quinazolinone.

48. The compound according to claim 8 Trans(+/−)-2-Butyl-6-(hexahydro-2,6,6-trimethylpyrrolo[1,2-b]isoxazol-2-yl)-3-[[2'-[1-(triphenylmethyl)-1H- tetrazol-5-yl][1,1'-biphenyl]-4-yl]methyl]-4(3H)-quinazolinone.

49. The compound according to claim 8 Cis-2-Butyl-6-(hexahydro-2-methyl-2H-isoxazolo[2,3-a]pyridin-2-yl)-3-[[2'-[1-(triphenylmethyl)-1H-tetrazol-5-yl][1,1'-biphenyl]-4-yl]methyl]-4(3H)-quinazolinone.

50. The compound according to claim 8 Trans-2-Butyl-6-(hexahydro-2-methyl-2H-isoxazolo[2,3-a]pyridin-2-yl)-3-[[2'-[1-(triphenylmethyl)-1H-tetrazol-5-yl][1,1'-biphenyl]-4-yl]methyl]-4(3H)-quinazolinone.

51. The compound according to claim 8 Cis-2-butyl-6-(hexahydro-2-phenylpyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone.

52. The compound according to claim 8 Cis-2-butyl-6-(2-ethylhexahydropyrrolo[1,2-b]isoxazol-2-yl)-3-[[2'-[1-(triphenylmethyl)-1H-tetrazol-5-yl][1,1'-biphenyl]-4-yl]methyl]-4(3H)-quinazolinone.

53. The compound according to claim 8 Trans-2-butyl-6-(2-ethylhexahydropyrrolo[1,2-b]isoxazol-2-yl)-3-[[2'-[1-triphenylmethyl)-1H-tetrazol-5-yl][1,1'-biphenyl]-4-yl]-methyl]-4(3H)-quinazolinone.

54. A pharmaceutical composition useful for treating angiotensin induced hypertension or congestive heart failure in a mammal comprising a suitable pharmaceutical carrier and an effective amount of a compound of claim 1.

55. A method of treating angiotensin induced hypertension in a mammal comprising administering a compound of claim 1 to said mammal an amount effective to lower angiotensin induced hypertension.

56. A method of treating congestive heart failure in a mammal comprising administering a compound of claim 1 to said mammal in an amount effective to treat congestive heart failure.

* * * * *